United States Patent
Wolkerstorfer et al.

(10) Patent No.: US 9,434,745 B2
(45) Date of Patent: Sep. 6, 2016

(54) 7-OXO-THIAZOLOPYRIDINE CARBONIC ACID DERIVATIVES AND THEIR USE IN THE TREATMENT, AMELIORATION OR PREVENTION OF A VIRAL DISEASE

(71) Applicants: Savira Pharmaceuticals GmbH, Vienna (AT); F. Hoffmann-La Roche AG, Basel (CH); European Molecular Biology Laboratory, Heidelberg (DE)

(72) Inventors: Andrea Wolkerstorfer, Vienna (AT); Oliver Szolar, Vienna (AT); Norbert Handler, Vienna (AT); Stephen Cusack, Seyssinet (FR); Thibault Sauvaitre, Frankfurt am Main (DE); Céline Simon, Illkirch (FR); Christophe Morice, Widensolen (FR); Bruno Giethlen, Altorf (FR); Thierry Langer, Oberschaeffolsheim (FR); Mark Smith, Jersey City, NJ (US); Sung-Sau So, Verona, NJ (US); Dirk Classen-Houben, Kramsach (AT); Helmut Buschmann, Aachen (DE)

(73) Assignees: Savira pharmaceuticals GmbH, Vienna (AT); F. Hoffmann-La Roche AG, Basel (CH); European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 13/900,964

(22) Filed: May 23, 2013

(65) Prior Publication Data

US 2013/0317022 A1     Nov. 28, 2013

Related U.S. Application Data

(60) Provisional application No. 61/650,713, filed on May 23, 2012.

(51) Int. Cl.
| | | |
|---|---|---|
| C07D 513/04 | (2006.01) | |
| A61K 31/437 | (2006.01) | |
| A61K 31/496 | (2006.01) | |
| A61K 31/519 | (2006.01) | |
| A61K 31/5377 | (2006.01) | |
| A61K 45/06 | (2006.01) | |
| C07D 487/04 | (2006.01) | |

(52) U.S. Cl.
CPC .......... *C07D 513/04* (2013.01); *A61K 31/437* (2013.01); *A61K 31/496* (2013.01); *A61K 31/519* (2013.01); *A61K 31/5377* (2013.01); *A61K 45/06* (2013.01); *C07D 487/04* (2013.01)

(58) Field of Classification Search
CPC .................................................... C07D 513/04
See application file for complete search history.

(56) References Cited

U.S. PATENT DOCUMENTS 6,559,145 B2 *   5/2003   Ciske et al.   ............... 514/232.5

FOREIGN PATENT DOCUMENTS

WO          02/04444 A2     1/2002

OTHER PUBLICATIONS

Muller and Kräusslich in "Antiviral Strategies" Handbook of Experimental Pharmacology vol. 189 Chapter 1, pp. 1-24.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Lau et. al. "Scope and Limitations of The Co-Drug Approach to Topical Drug Delivery" Current Pharmaceutical Design, 2008, 14, 794-802.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Leysen DC, et al. (1984) Thiazolopyridine analogs of naldixic acid. 1. Thiazolo[5,4-b]pyridines. Journal of Heterocyclic Chemistry, 21(2):401-406.

* cited by examiner

*Primary Examiner* — David K. O'Dell
(74) *Attorney, Agent, or Firm* — Mintz Levin Cohn Ferris Glovsky and Popeo, P.C.

(57) ABSTRACT

The present invention relates to a compound having the general formula (A), optionally in the form of a pharmaceutically acceptable salt, solvate, polymorph, codrug, cocrystal, prodrug, tautomer, racemate, enantiomer, or diastereomer or mixture thereof,

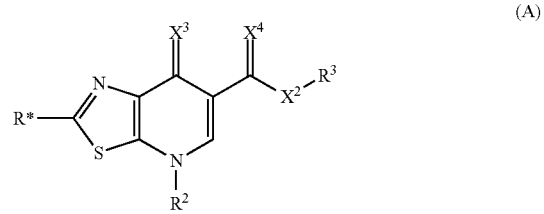

(A)

which are useful in treating, ameliorating or preventing a viral disease. Furthermore, specific combination therapies are disclosed.

14 Claims, No Drawings

7-OXO-THIAZOLOPYRIDINE CARBONIC ACID DERIVATIVES AND THEIR USE IN THE TREATMENT, AMELIORATION OR PREVENTION OF A VIRAL DISEASE

CROSS-REFERENCE TO RELATED APPLICATIONS

This application claims benefit to U.S. Provisional Application No. 61/650,713, filed May 23, 2012. The contents of the above application are incorporated by reference as if recited in full herein.

FIELD OF THE INVENTION

The present invention relates to a compound having the general formula (A), optionally in the form of a pharmaceutically acceptable salt, solvate, polymorph, codrug, cocrystal, prodrug, tautomer, racemate, enantiomer, or diastereomer or mixture thereof,

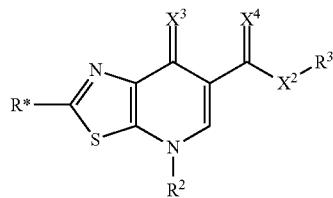

(A)

which is useful in treating, ameloriating or preventing a viral disease. Furthermore, specific combination therapies are disclosed.

BACKGROUND OF THE INVENTION

In recent years the serious threat posed by influenza virus to worldwide public health has been highlighted by, firstly, the ongoing low level transmission to humans of the highly pathogenic avian H5N1 strain (63% mortality in infected humans, http://www.who.int/csr/disease/avian_influenza/en/) and secondly, the unexpected emergence in 2009 of a novel pandemic strain A/H1N1 that has rapidly spread around the entire world (http://www.who.int/csr/disease/swineflu/en/). Whilst the new strain is highly contagious but currently only generally gives mild illness, the future evolution of this virus is unpredictable. In a much more serious, but highly plausible scenario, H5N1 could have been more easily transmissible between humans or the new A/H1N1 could have been more virulent and could have carried the single point mutation that confers Tamiflu resistance (Neumann et al., Nature, 2009 (18; 459(7249) 931-939)); as many seasonal H1N1 strains have recently done (Dharan et al., The Journal of the American Medical Association, 2009 Mar. 11; 301 (10), 1034-1041; Moscona et al., The New England Journal of Medicine, 2009 (March 5; 360(10) pp 953-956)). In this case, the delay in generating and deploying a vaccine (~6 months in the relatively favourable case of A/H1N1 and still not a solved problem for H5N1) could have been catastrophically costly in human lives and societal disruption.

It is widely acknowledged that to bridge the period before a new vaccine becomes available and to treat severe cases, as well as to counter the problem of viral resistance, a wider choice of anti-influenza drugs is required. Development of new anti-influenza drugs has therefore again become a high priority, having been largely abandoned by the major pharmaceutical companies once the anti-neuraminidase drugs became available.

An excellent starting point for the development of anti-viral medication is structural data of essential viral proteins. Thus, the crystal structure determination of e.g. the influenza virus surface antigen neuraminidase (Von ltzstein, M. et al., (1993), Nature, 363, pp. 418-423) led directly to the development of neuraminidase inhibitors with anti-viral activity preventing the release of virus from the cells, however, not the virus production. These and their derivatives have subsequently developed into the anti-influenza drugs, zanamivir (Glaxo) and oseltamivir (Roche), which are currently being stockpiled by many countries as a first line of defence against an eventual pandemic. However, these medicaments provide only a reduction in the duration of the clinical disease. Alternatively, other anti-influenza compounds such as amantadine and rimantadine target an ion channel protein, i.e., the M2 protein, in the viral membrane interfering with the uncoating of the virus inside the cell. However, they have not been extensively used due to their side effects and the rapid development of resistant virus mutants (Magden, J. et al., (2005), Appl. Microbiol. Biotechnol., 66, pp. 612-621). In addition, more unspecific viral drugs, such as ribavirin, have been shown to work for treatment of influenza and other virus infections (Eriksson, B. et al., (1977), Antimicrob. Agents Chemother., 11, pp. 946-951). However, ribavirin is only approved in a few countries, probably due to severe side effects (Furuta et al., ANTIMICROBIAL AGENTS AND CHEMOTHERAPY, 2005, p. 981-986). Clearly, new antiviral compounds are needed, preferably directed against different targets.

Influenza virus as well as Thogotovirus belong to the family of Orthomyxoviridae which, as well as the family of the Bunyaviridae, including the Hantavirus, Nairovirus, Orthobunyavirus, and Phlebovirus, are negative stranded RNA viruses. Their genome is segmented and comes in ribonucleoprotein particles that include the RNA dependent RNA polymerase which carries out (i) the initial copying of the single-stranded virion RNA (vRNA) into viral mRNAs and (ii) the vRNA replication. This enzyme, a trimeric complex composed of subunits PA, PB1 and PB2, is central to the life cycle of the virus since it is responsible for the replication and transcription of viral RNA. In previous work the atomic structure of two key domains of the polymerase, the mRNA cap-binding domain in the PB2 subunit (Guilligay et al., Nature Structural & Molecular Biology 2008; May; 15(5): 500-506) and the endonuclease-active site in the PA subunit (Dias et al., Nature 2009, 458, 914-918) have been identified and determined. These two sites are critical for the unique cap-snatching mode of transcription that is used by influenza virus to generate viral mRNAs. For the generation of viral mRNA the polymerase makes use of the so called "cap-snatching" mechanism (Plotch, S. J. et al., (1981), —Cell, 23, pp. 847-858; Kukkonen, S. K. et al (2005), Arch. Virol., 150, pp. 533-556; Leahy, M. B. et al, (2005), J. Virol., 71, pp. 8347-8351; Noah, D. L. et al., (2005), Adv. Virus Res., 65, pp. 121-145). A 5' cap (also termed an RNA cap, RNA 7-methylguanosine cap or an RNA m7G cap) is a modified guanine nucleotide that has been added to the 5' end of a messenger RNA. The 5' cap consists of a terminal 7-methylguanosine residue which is linked through a 5'-5'-triphosphate bond to the first transcribed nucleotide. The viral polymerase binds to the 5' RNA cap of cellular mRNA molecules and cleaves the RNA cap together with a stretch of 10 to 15 nucleotides. The capped RNA fragments then serve as primers for the synthesis of viral mRNA.

The polymerase complex seems to be an appropriate antiviral drug target since it is essential for synthesis of viral mRNA and viral replication and contains several functional active sites likely to be significantly different from those found in host cell proteins (Magden, J. et al., (2005), Appl. Microbiol. Biotechnol., 66, pp. 612-621). Thus, for example, there have been attempts to interfere with the assembly of polymerase subunits by a 25-amino-acid peptide resembling the PA-binding domain within PB1 (Ghanem, A. et al., (2007), J. Virol., 81, pp. 7801-7804). Furthermore, the endonuclease activity of the polymerase has been targeted and a series of 4-substituted 2,4-dioxobutanoic acid compounds has been identified as selective inhibitors of this activity in influenza viruses (Tomassini, J. et al., (1994), Antimicrob. Agents Chemother., 38, pp. 2827-2837). In addition, flutimide, a substituted 2,6-diketopiperazine, identified in extracts of Delitschia confertaspora, a fungal species, has been shown to inhibit the endonuclease of influenza virus (Tomassini, J. et al., (1996), Antimicrob. Agents Chemother., 40, pp. 1189-1193). Moreover, there have been attempts to interfere with viral transcription by nucleoside analogs, such as 2'-deoxy-2'-fluoroguanosine (Tisdale, M. et al., (1995), Antimicrob. Agents Chemother., 39, pp. 2454-2458).

Certain heterocyclic carboxamides which are stated to be useful in preventing or treating atherosclerosis or restenosis are disclosed in WO 2004/019933. The compounds are stated to be useful in these applications due to their activity against herpes viruses because atherosclerosis is related to a number of herpes virus infections.

WO 02/04444 discloses specific heterocyclic carboxamides as antiviral agents.

O. Tabarrini et al. investigated the naphthyridone scaffold and in particular identified a 1,6-naphthyridone derivative with anti-HIV activity in ChemMedChem, 2011, 6(7), 1249-1257.

It is an object of the present invention to identify further compounds which are effective against viral diseases and which have improved pharmacological properties.

SUMMARY OF THE INVENTION

Accordingly, in a first embodiment, the present invention provides a compound having the general formula (A).

It is understood that throughout the present specification the term "a compound having the general formula (A)" encompasses pharmaceutically acceptable salts, solvates, polymorphs, prodrugs, tautomers, racemates, enantiomers, or diastereomers or mixtures thereof unless mentioned otherwise.

A further embodiment of the present invention relates to a pharmaceutical composition comprising a compound having the general formula (A) and optionally one or more pharmaceutically acceptable excipient(s) and/or carrier(s).

The compounds having the general formula (A) are useful for treating, ameliorating or preventing viral diseases.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, —CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

The term "alkyl" refers to a saturated straight or branched carbon chain.

The term "cycloalkyl" represents a cyclic version of "alkyl". The term "cycloalkyl" is also meant to include bicyclic, tricyclic and polycyclic versions thereof. Unless specified otherwise, the cycloalkyl group can have 3 to 12 carbon atoms.

"Hal" or "halogen" represents F, Cl, Br and I.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl, preferably phenyl.

The term "heteroaryl" preferably refers to a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from O, N and S. Examples of the heteroaryl group include pyrrole, pyrrolidine, oxolane, furan, imidazolidine, imidazole, pyrazole, oxazolidine, oxazole, thiazole, piperidine, pyridine, morpholine, piperazine, and dioxolane.

The term "hydrocarbon group which contains from 5 to 20 carbon atoms and optionally 1 to 4 heteroatoms selected from O, N and S and which contains at least one ring" refers to any group having 5 to 20 carbon atoms and optionally 1 to 4 heteroatoms selected from O, N and 2 as long as the group contains at least one ring. The term is also meant to include bicyclic, tricyclic and polycyclic versions thereof. If more than one ring is present, they can be separate from each other or be annelated. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —(CH$_2$)$_p$— with p=1 to 6). Examples of these groups include (optionally substituted C$_{3-7}$ cycloalkyl), (optionally substituted aryl) wherein the aryl group can be, for example, phenyl, -(optionally substituted biphenyl), adamantyl, —(C$_{3-7}$ cycloalkyl)-aryl as well as the corresponding compounds with a linker.

The term "(optionally substituted mono- or polycyclic group containing 3 to 20 carbon atoms and optionally 1 to 4 heteroatoms selected from O, N and S)" refers to any mono- or polycyclic group containing 3 to 20 carbon atoms and optionally 1 to 4 heteroatoms selected from O, N and S. This term includes monocyclic, bicyclic, tricyclic and polycyclic versions thereof. If more than one ring is present, they can be separate from each other or be annelated. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —(CH$_2$)$_p$— with p=1 to 6). Examples of these groups include (optionally substituted C$_{3-7}$ cycloalkyl), and -(optionally substituted aryl) wherein the aryl group can be, for example, phenyl or anthracenyl as well as the corresponding compounds with a linker.

If a compound or moiety is referred to as being "optionally substituted", it can in each instance include 1 or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups. If $X^2$ is O or S, preferred examples of the prodrug include compounds in which $R^3$ is replaced by one of the following groups:

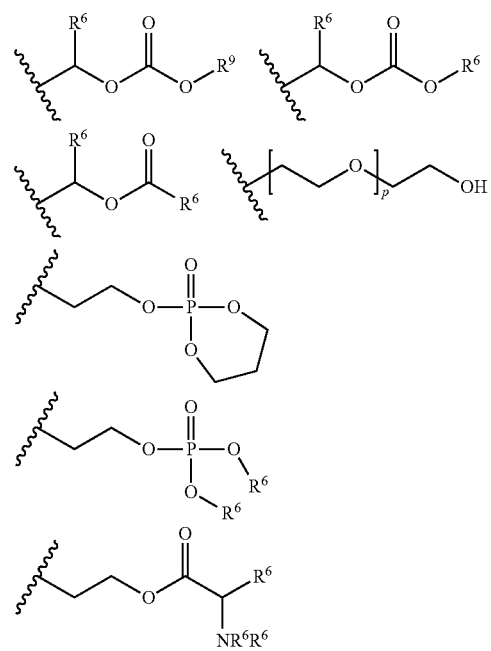

In these formulae, $R^6$ can be the same or different. $R^9$ is a cyclic group such as an aryl group or a C$_{3-7}$ cycloalkyl group. p is 2 to 8.

If $X^2$ is NR$^4$, preferred examples of the prodrug include compounds in which $R^3$ and $R^4$ are not both H.

Compounds Having the General Formula (A)

The present invention provides a compound having the general formula (A).

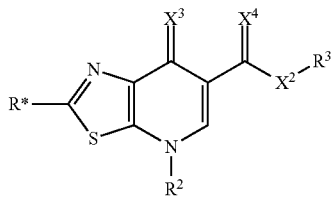

(A)

The present invention provides a compound having the general formula (A) in which the following definitions apply.

R* is —H, —Hal, (optionally substituted $C_{1-6}$ alkyl), (optionally substituted $C_{3-7}$ cycloalkyl), (optionally substituted aryl), —$C_{1-4}$ alkyl(optionally substituted $C_{3-7}$ cycloalkyl), —$C_{1-4}$ alkyl(optionally substituted aryl) or —$X^1$—$R^1$. In a preferred embodiment, R* is —Hal, (optionally substituted $C_{1-6}$ alkyl) (wherein the optional substituent of the alkyl group is preferably Hal, more preferably F); —$C_{1-4}$ alkyl(optionally substituted aryl) (wherein the optional substituent of the aryl group is preferably halogen) or —$X^1$—$R^1$. In a more preferred embodiment R* is $X^1$—$R^1$.

$X^1$ is O, C(O), C(O)O, OC(O); S, SO, $SO_2$, $NR^4$, $N(R^5)C(O)$, $C(O)NR^5$, preferably $X^1$ is O, or $NR^4$, more preferably $X^1$ is $NR^4$. In one preferred embodiment, $X^1$ is $NR^4$ and $R^1$ and $R^4$ are joined together to form a 5- to 7-membered ring, which can optionally contain O, S or further N. In another preferred embodiment, $X^1$ is $NR^4$ and $R^1$ is —$SO_2$—$R^4$.

$X^2$ is O, S, $NR^4$, preferably $X^2$ is O.

$X^3$ is O or S, preferably $X^3$ is O.

$X^4$ is O or S, preferably $X^4$ is O.

$R^1$ is —H, (optionally substituted $C_{1-6}$ alkyl), -(optionally substituted $C_{3-7}$ cycloalkyl), (optionally substituted aryl), —$C_{1-4}$ alkyl(optionally substituted $C_{3-7}$ cycloalkyl), —$C_{1-4}$ alkyl-(optionally substituted aryl). Preferably $R^1$ is —H, -(optionally substituted $C_{1-6}$ alkyl), -(optionally substituted benzyl), more preferably $R^1$ is —H or -(optionally substituted benzyl). Throughout the present specification, it is understood that the definitions of the substituents of the aryl group apply analogously to the benzyl group.

$R^2$ is a hydrocarbon group which contains from 5 to 20 carbon atoms and optionally 1 to 4 heteroatoms selected from O, N and S and which contains at least one ring, wherein the hydrocarbon group can be optionally substituted. Preferably, the at least one ring is aromatic such as an aryl or heteroaryl ring. More preferably, $R^2$ is a hydrocarbon group which contains from 5 to 20 carbon atoms and optionally 1 to 4 heteroatoms and which contains at least two rings, wherein the hydrocarbon group can be optionally substituted.

Even more preferably, at least one of the at least two rings is aromatic such as an aryl or heteroaryl ring. Preferred examples of $R^2$ can be selected from the group consisting of

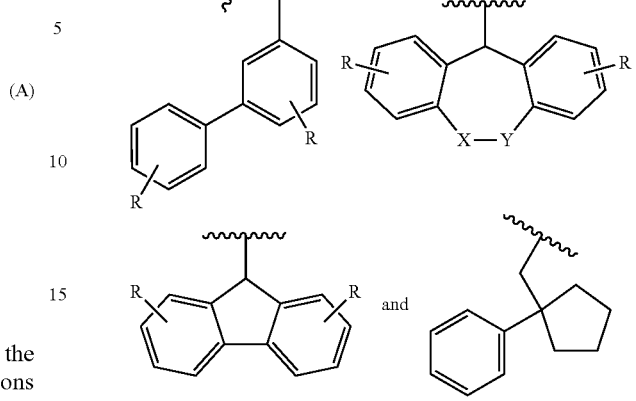

and wherein

X is absent, $CH_2$, NH, C(O)NH, S or O. Furthermore, Y is $CH_2$.

In an alternative embodiment, X and Y can be joined together to form an annulated, carbo- or heterocyclic 3- to 8-membered ring which can be saturated or unsaturated. Specific examples of X-Y include —$CH_2$—, —$CH_2$—$CH_2$—, —O—, and —NH—.

R is independently selected from H, —$C_{1-6}$ alkyl, halogen, —CN, —OH, and —O—$C_{1-6}$ alkyl.

$R^3$ is —H, -(optionally substituted $C_{1-6}$ alkyl), (optionally substituted $C_{3-7}$ cycloalkyl), -(optionally substituted aryl), or —$C_{1-4}$ alkyl(optionally substituted aryl) or if $X^2$ is $NR^4$, then $R^3$ can also be —OH, preferably $R^3$ is —H, —$C_{1-6}$ alkyl or Bz.

$R^4$ is —H, (optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^1$ is $NR^4$, then $R^4$ and $R^1$ can be joined together to form a 5- to 7-membered ring, which can optionally contain O, S or further N or if $X^2$ is $NR^4$, then $R^4$ and $R^3$ can be joined together to form a 5- to 7-membered ring, which can optionally contain O, S or further N. Preferably, $R^4$ is —H, -(optionally substituted aryl), or -(optionally substituted $C_{1-6}$ alkyl), more preferably, $R^4$ is —H or -(optionally substituted benzyl).

$R^5$ is —H, -(optionally substituted $C_{1-6}$ alkyl), -(optionally substituted $C_{3-7}$ cycloalkyl), -(optionally substituted aryl), —$C_{1-4}$ alkyl(optionally substituted $C_{3-7}$ cycloalkyl), or —$C_{1-4}$ alkyl-(optionally substituted aryl). Preferably, $R^5$ is —H.

$R^6$ is —H, or —$C_{1-6}$ alkyl.

The optional substituent of the alkyl group is selected from the group consisting of halogen, —CN, —$NR^6R^6$, —OH, and —O—$C_{1-6}$ alkyl. Preferably the substituent is halogen, more preferably F.

The optional substituent of the cycloalkyl group, the aryl group or the hydrocarbon group is selected from the group consisting of —$C_{1-6}$ alkyl, halogen, —$CF_3$, —CN, —$X^1$—$R^5$ and —$C_{1-4}$ alkyl-aryl. Preferably, the substituent is -halogen (preferably F), —$OCH_3$ or —CN.

The present inventors have surprisingly found that the compounds of the present invention which have a bulky moiety $R^2$ have improved pharmacological properties compared to corresponding compounds which have a smaller moiety $R^2$. Without wishing to be bound by theory it is assumed that the viral polymerase protein has a pocket for binding and that the bulky moiety $R^2$ of the compounds of the present invention fills this pocket to a larger extent. It is further assumed that the larger moiety $R^2$ is able to provide more hydrophobic interaction with the pocket than smaller moieties such as methyl.

The compounds of the present invention can be administered to a patient in the form of a pharmaceutical composition which can optionally comprise one or more pharmaceutically acceptable excipient(s) and/or carrier(s).

The compounds of the present invention can be administered by various well known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a spray, a tablet, a capsule, a capslet, lozenge, a liposome, a suppository, a plaster, a band-aid, a retard capsule, a powder, or a slow release formulation. Preferably, the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride, may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following non-limiting list:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerids and sodium stearyl fumarates,
c) disintegrants such as starches, croscarmellose, sodium methyl cellulose, agar, bentonite, alginic acid, carboxymethyl cellulose, polyvinyl pyrrolidone and the like.

In one embodiment the formulation is for oral administration and the formulation comprises one or more or all of the following ingredients: pregelatinized starch, talc, povidone K 30, croscarmellose sodium, sodium stearyl fumarate, gelatin, titanium dioxide, sorbitol, monosodium citrate, xanthan gum, titanium dioxide, flavoring, sodium benzoate and saccharin sodium.

If a compound of the invention is administered intranasally in a preferred embodiment, it may be administered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoro-alkane such as 1,1,1,2-tetrafluoroethane (HFA 134A™) or 1,1,1,2,3,3,3-heptafluoropropane (HFA 227EA™), carbon dioxide, or another suitable gas. The pressurized container, pump, spray or nebulizer may contain a solution or suspension of the compound of the invention, e.g., using a mixture of ethanol and the propellant as the solvent, which may additionally contain a lubricant, e.g., sorbitan trioleate.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g of the active ingredient (i.e. compound of the invention) per kg body weight. However, in a preferred use of the present invention a compound of the invention is administered to a subject in need thereof in an amount ranging from 1.0 to 500 mg/kg body weight, preferably ranging from 1 to 200 mg/kg body weight. The duration of therapy with a compound of the invention will vary, depending on the severity of the disease being treated and the condition and idiosyncratic response of each individual patient. In one preferred embodiment of a prophylactic or therapeutic use, from 10 mg to 200 mg of the compound are orally administered to an adult per day, depending on the severity of the disease and/or the degree of exposure to disease carriers.

As is known in the art, the pharmaceutically effective amount of a given composition will also depend on the administration route. In general, the required amount will be higher if the administration is through the gastrointestinal tract, e.g., by suppository, rectal, or by an intragastric probe, and lower if the route of administration is parenteral, e.g., intravenous. Typically, a compound of the invention will be administered in ranges of 50 mg to 1 g/kg body weight, preferably 10 mg to 500 mg/kg body weight, if rectal or intragastric administration is used and in ranges of 1 to 100 mg/kg body weight if parenteral administration is used. For intranasal administration, 1 to 100 mg/kg body weight are envisaged.

If a person is known to be at risk of developing a disease treatable with a compound of the invention, prophylactic administration of the biologically active blood serum or the pharmaceutical composition according to the invention may be possible. In these cases the respective compound of the invention is preferably administered in above outlined preferred and particular preferred doses on a daily basis. Preferably, from 0.1 mg to 1 g/kg body weight once a day, preferably 10 to 200 mg/kg body weight. This administration can be continued until the risk of developing the respective viral disorder has lessened. In most instances, however, a compound of the invention will be administered once a disease/disorder has been diagnosed. In these cases it is preferred that a first dose of a compound of the invention is administered one, two, three or four times daily.

The compounds of the present invention are particularly useful for treating, ameliorating, or preventing viral diseases. The type of viral disease is not particularly limited. Examples of possible viral diseases include, but are not limited to, viral diseases which are caused by Poxyiridae, Herpesviridae, Adenoviridae, Papillomaviridae, Polyomaviridae, Parvoviridae, Hepadnaviridae, Retroviridae, Reoviridae, Filoviridae, Paramyxoviridae, Rhabdoviridae, Orthomyxoviridae, Bunyaviridae, Arenaviridae, —Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Retroviridae, Filoviridae, Paramyxoviridae, Rhabdoviridae, Orthomyxoviridae, Bunyaviridae, Arenaviridae, Coronaviridae, Picornaviridae, Togaviridae, Flaviviridae, more preferably viral diseases which are caused by orthomyxoviridae.

Examples of the various viruses are given in the following table.

| Family | Virus (preferred examples) |
|---|---|
| Poxviridae | Smallpox virus |
| | Molluscum contagiosum virus |
| Herpesviridae | Herpes simplex virus |
| | Varicella zoster virus |
| | Cytomegalovirus |
| | Epstein Barr virus |
| | Kaposi's sarcoma-associated herpesvirus |
| Adenoviridae | Human adenovirus A-F |
| Papillomaviridae | Papillomavirus |
| Polyomaviridae | BK-virus |
| | JC-Virsu |
| Parvoviridae | B19 virus |
| | Adeno associated virus 2/3/5 |
| Hepadnaviridae | Hepatitis B virus |
| Retroviridae | Human immunodeficiency virus types 1/2 |
| | Human T-cell leukemia virus |
| | Human foamy virus |
| Reoviridae | Reovirus 1/2/3 |
| | Rotavirus A/B/C |
| | Colorado tick fever virus |
| Filoviridae | Ebola virus |
| | Marburg virus |
| Paramyxoviridae | Parainfluenza virus 1-4 |
| | Mumps virus |
| | Measles virus |
| | Respiratory syncytial virus |
| | Hendravirus |
| Rhabdoviridae | Vesicular stomatitis virus |
| | Rabies virus |
| | Mokola virus |
| | European bat virus |
| | Duvenhage virus |
| Orthomyxoviridae | Influenza virus types A-C |
| Bunyaviridae | California encephalitis virus |
| | La Crosse virus |
| | Hantaan virus |
| | Puumala virus |
| | Sin Nombre virus |
| | Seoul virus |
| | Crimean-Congo hemorrhagic fever virus |
| | Sakhalin virus |
| | Rift valley virus |
| | Sandfly fever virus |
| | Uukuniemi virus |
| Arenaviridae | Lassa virus |
| | Lymphocytic choriomeningitis virus |
| | Guanarito virus |
| | Junin virus, |
| | Machupo virus |
| | Sabia virus |
| Coronaviridae | Human coronavirus |
| Picornaviridae | Human enterovirus types A-D (Poliovirus, Echovirus, Coxsackie virus A/B) |
| | Rhinovirus types A/B/C |
| | Hepatitis A virus |
| | Parechovirus |
| | Food and mouth disease virus |
| Hepeviridae | Hepatitis E virus |
| Caliciviridae | Norwalk virus |
| | Sapporo virus |
| Astroviridae | Human astrovirus 1 |
| Togaviridae | Ross River virus |
| | Chikungunya virus |
| | O'nyong-nyong virus |
| | Rubella virus |
| Flaviviridae | Tick-borne encephalitis virus |
| | Dengue virus |
| | Yellow Fever virus |
| | Japanese encephalitis virus |
| | Murray Valley virus |
| | St. Louis encephalitis virus |
| | West Nile virus |
| | Hepatitis C virus |
| | Hepatitis G virus |
| | Hepatitis GB virus |
| Deltavirus | Hepatitis deltavirus |
| Bornaviridae | Bornavirus |
| Prions | |

Preferably, the compounds of the present invention are employed to treat influenza. Within the present invention, the term "influenza" includes influenza A, B, C, isavirus and thogotovirus and also covers bird flu and swine flu. The subject to be treated is not particularly restricted and can be any vertebrate, such as birds and mammals (including humans).

Without wishing to be bound by theory it is assumed that the compounds of the present invention are capable of inhibiting endonuclease activity, particularly of the influenza virus. More specifically it is assumed that they directly interfere with the N-terminal part of the influenza PA protein, which harbours endonuclease activity. However, delivery of a compound into a cell may represent a problem depending on, e.g., the solubility of the compound or its capabilities to cross the cell membrane. The present invention not only shows that the claimed compounds have in vitro polymerase inhibitory activity but also in vivo antiviral activity.

A possible measure of the in vitro polymerase inhibitory activity of the compounds having the formula (A) and/or (C) is the FRET endonuclease activity assay disclosed herein.

Preferably, the compounds exhibit a % reduction of at least about 50% at 25 μM in the FRET assay. In this context, the % reduction is the % reduction of the initial reaction velocity (v0) of substrate cleavage of compound-treated samples compared to untreated samples. Preferably, the compounds exhibit an IC$_{50}$ of at least about 40 μM, more preferably at least about 20 μM, in the FRET assay. The half maximal inhibitory concentration (IC$_{50}$) is a measure of the effectiveness of a compound in inhibiting biological or biochemical function and was calculated from the initial reaction velocities (v0) in a given concentration series ranging from maximum 100 μM to at least 2 nM.

A possible measure of the in vivo antiviral activity of the compounds having the formula (A) and/or (C) is the CPE assay disclosed herein. Preferably, the compounds exhibit a % reduction of at least about 30% at 50 μM. In this connection, the reduction in the virus-mediated cytopathic effect (CPE) upon treatment with the compounds was calculated as follows: The cell viability of infected-treated and uninfected-treated cells was determined using an ATP-based cell viability assay (Promega). The response in relative luminescent units (RLU) of infected-untreated samples was subtracted from the response (RLU) of the infected-treated samples and then normalized to the viability of the corresponding uninfected sample resulting in % CPE reduction. Preferably, the compounds exhibit an IC$_{50}$ of at least about 45 μM, more preferably at least about 10 μM, in the CPE assay. The half maximal inhibitory concentration (IC$_{50}$) is a measure of the effectiveness of a compound in inhibiting biological or biochemical function and was calculated from the RLU response in a given concentration series ranging from maximum 100 μM to at least 100 nM.

The compounds having the general formula (A) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza.

The following combinations of medicaments are envisaged as being particularly suitable:

(i) The combination of endonuclease and cap-binding inhibitors (particularly targeting influenza). The endonuclease inhibitors are not particularly limited and can be any endonuclease inhibitor, particularly any viral endonuclease inhibitor. Preferred endonuclease inhibitors are those having the general formula (I) as defined in the U.S. application with the Ser. No. 61/550,045, filed on Oct. 21, 2011, the complete disclosure of which is incorporated by reference. In particular, all descriptions with respect to the general formula of the compounds according to U.S. 61/550,045, the preferred embodiments of the various substituents as well as the medical utility and advantages of the compounds are incorporated herein by reference.

The compounds having the general formula (I) of this reference can optionally be in the form of a pharmaceutically acceptable salt, solvate, polymorph, codrug, cocrystal, prodrug, tautomer, racemate, enantiomer, or diastereomer or mixture thereof. They are defined as follows (wherein the definitions of the various moieties given in this earlier application apply):

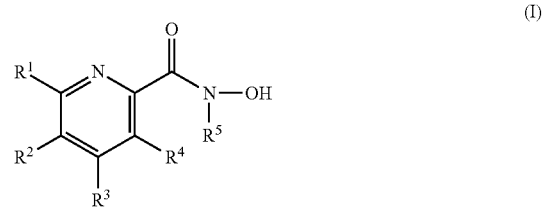

wherein
$R^1$ is selected from —H, —C$_{1-6}$ alkyl, (C$_{3-7}$ cycloalkyl) and —CH$_2$—(C$_{3-7}$ cycloalkyl);
$R^2$ is selected from —H,

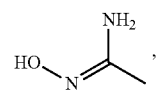

—C$_{1-6}$ alkyl, —Hal, —(C$_{3-7}$ cycloalkyl), —CH$_2$—(C$_{3-7}$ cycloalkyl), —(CH$_2$)$_n$-(optionally substituted aryl), (optionally substituted 5- or 6-membered heterocyclic ring which contains at least one heteroatom selected from N, O and S, wherein the substituent is selected from —C$_{1-4}$ alkyl, halogen, —CN, —CHal$_3$, -aryl, —NR$^6$R$^7$, and —CONR$^6$R$^7$;
$R^3$ is selected from H, —C$_{1-6}$ alkyl,
  —(CH$_2$)$_n$—NR$^6$R$^8$,
  -(optionally substituted 5- or 6-membered carbo- or heterocyclic ring wherein the heterocyclic ring contains at least one heteroatom selected from N, O and S), wherein the substituent is selected from —Hal, —C$_{1-4}$ alkyl, —NR$^9$R$^{10}$, —(CH$_2$)$_n$—OH, —C(O)—NR$^9$R$^{10}$, —SO$_2$—NR$^9$R$^{10}$, —NH—C(O)—O—R$^{11}$, —C(O)—O—R$^{11}$, and a 5- or 6-membered heterocyclic ring which contains at least one heteroatom selected from N, O and S;
or wherein $R^1$ and $R^2$ together form a phenyl ring or wherein $R^2$ and $R^3$ together form a phenyl ring;
$R^4$ is H;
$R^5$ is selected from the group consisting of —H or —(CH$_2$)$_n$-(optionally substituted aryl), wherein the substituent is selected from —Hal and —C$_{1-4}$ alkyl; or wherein $R^4$ and $R^5$ together form a methylene group —CH$_2$—, ethylene group —CH$_2$CH$_2$— or ethyne group —CHCH—, which can be optionally substituted by —C$_{1-4}$ alkyl, halogen, —CHal$_3$, —R$^6$R$^7$, —OR$^6$, —CONR$^6$R$^7$, —SO$_2$R$^6$R$^7$, aryl or heteroaryl;
$R^6$ is selected from —H and —C$_{1-4}$ alkyl;
$R^7$ is selected from —H and —C$_{1-4}$ alkyl;
$R^8$ is selected from —H, —C$_{1-6}$ alkyl, —(CH$_2$)$_n$-(optionally substituted aryl), —SO$_2$—(CH$_2$)$_n$-(optionally substituted aryl), —SO$_2$—(CH$_2$)$_n$-(optionally substituted 5- to 10-membered mono- or bicyclic heteroring which contains at least one heteroatom selected from N, O and S), —(CH$_2$)$_n$-(optionally substituted 5- or 6-membered heterocyclic ring which contains at least one heteroatom selected from N, O and S), wherein the substituent is selected from —Hal, —CF$_3$, —C$_{1-4}$ alkyl, and —(CH$_2$)$_n$-aryl;
$R^9$ is selected from —H, —C$_{1-4}$ alkyl, and —C$_{1-4}$ alkylene-NR$^{11}$R$^{11}$;
$R^{10}$ is selected from —H, —C$_{1-4}$ alkyl, and —C$_{1-4}$ alkylene-NR$^{11}$R$^{11}$;
$R^{11}$ is selected from —H, —CF$_3$, and —C$_{1-4}$ alkyl;

each m is 0 or 1; and each n is independently 0, 1, 2, or 3.

Further preferred endonuclease inhibitors are those having the general formula (C) as defined in the copending application with Ser. No. 13/900,940 which was filed on even date herewith, the complete disclosure of which is incorporated by reference. In particular, all descriptions with respect to the general formula of the compounds having the general formula (C), the preferred embodiments of the various substituents as well as the medical utility and advantages of the compounds are incorporated herein by reference. The compounds having the general formula (C) can be optionally in the form of a pharmaceutically acceptable salt, solvate, polymorph, codrug, cocrystal, prodrug, tautomer, racemate, enantiomer, or diastereomer or mixture thereof. They are defined below.

The cap-binding inhibitors are not particularly limited either and can be any cap-binding inhibitor, particularly any viral cap-binding inhibitor. Preferred cap-binding inhibitors are those having the general formula (II) as defined in U.S. application 61/550,057 and/or the compounds disclosed in WO2011/000566, the complete disclosure of which is incorporated by reference. In particular, all descriptions with respect to the general formula of the compounds according to U.S. 61/550,057 or WO2011/000566, the preferred embodiments of the various substituents as well as the medical utility and advantages of the compounds are incorporated herein by reference.

The compound having the general formula (II) can be optionally in the form of a pharmaceutically acceptable salt, solvate, polymorph, codrug, cocrystal, prodrug, tautomer, racemate, enantiomer, or diastereomer or mixture thereof. It is defined as follows:

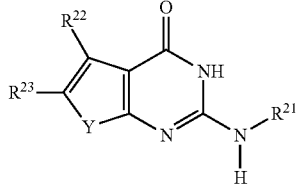

(II)

wherein

Y is S;

$R^{21}$ is selected from —H, —$C_{1-6}$alkyl, —$(CH_2)_q$-aryl, —$(CH_2)_q$-heterocyclyl, —$(CH_2)_q$-cycloalkyl, —$(CH_2)_p$—$OR^{25}$, and —$(CH_2)_p$—$NR^{25}R^{26}$;

$R^{22}$ is selected from —H, —$C_{1-6}$ alkyl, —$(CH_2)_q$-cycloalkyl, —Hal, —$CF_3$ and —CN;

$R^{23}$ is selected from aryl, heterocyclyl, cycloalkyl, —C(—$R^{28}$)(—$R^{29}$)-aryl, —C(—$R^{28}$)(—$R^{29}$)-heterocyclyl, and —C(—$R^{28}$)(—$R^{29}$)-cycloalkyl;

$R^{25}$ is selected from —H, —$C_{1-6}$ alkyl, and —$(CH_2CH_2O)_rH$;

$R^{26}$ is selected from —H, and —$C_{1-6}$ alkyl;

$R^{27}$ is independently selected from —$C_{1-6}$ alkyl, —C(O)—$C_{1-6}$ alkyl, —Hal, —$CF_3$, —CN, —$COOR^{25}$, —$OR^{25}$, —$(CH_2)_q NR^{25}R^{26}$, —C(O)—$NR^{25}R^{26}$, and $NR^{25}$—C(O)—$C_{1-6}$ alkyl;

$R^{28}$ and $R^{29}$ are independently selected from —H, —$C_{1-6}$ alkyl, —$(CH_2)_q$-aryl, —$(CH_2)_q$-heterocyclyl, —$(CH_2)_q$-cycloalkyl, —OH, —O—$C_{1-6}$ alkyl, —O—$(CH_2)_q$-aryl, —O—$(CH_2)_q$-heterocyclyl, and —O—$(CH_2)_q$-cycloalkyl;

or $R^{28}$ and $R^{29}$ are together =O, —$CH_2CH_2$, —$CH_2CH_2CH_2$—, or —$CH_2CH_2CH_2CH_2$—;

p is 1 to 4;

q is 0 to 4; and r is 1 to 3;

wherein the aryl group, heterocyclyl group and/or cycloalkyl group can be optionally substituted with one or more substituents $R^{27}$.

The compounds of WO2011/000566 have the general formula (XXI):

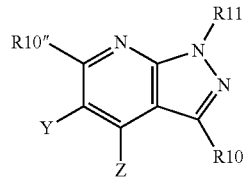

(XXI)

or a pharmaceutically effective salt, a solvate, a prodrug, a tautomer, a racemate, an enantiomer or a diastereomer thereof;

wherein one of Y and Z is $XR^{12}$ and the other is $R^{10'}$;

$R^{10}$, $R^{10'}$ and $R^{10''}$ are each individually selected from the group consisting of hydrogen, $C_1$-$C_6$-alkyl, $C_2$-$C_6$-alkenyl, $C_2$-$C_8$-alkynyl, —$(CH_2)_nC(O)OH$, —$(CH_2)_nC(O)OR^{16}$, —$(CH_2)_nOH$, —$(CH_2)_nOR^{16}$, —$CF_3$, —$(CH_2)_n$-cycloalkyl, —$(CH_2)_nC(O)NH_2$, —$(CH_2)_nC(O)NHR^{16}$, —$(CH_2)_nC(O)NR^{16}R^{17}$, —$(CH_2)_nS(O)_2NH_2$, —$(CH_2)_nS(O)_2NHR^{16}$, —$(CH_2)_nS(O)_2NR^{16}R^{17}$, —$(CH_2)_nS(O)_2R^{16}$, halogen, —CN, —$(CH_2)_n$-aryl, —$(CH_2)_n$-heteroaryl, —$(CH_2)_nNH_2$, —$(CH_2)_nNHR^{16}$, and —$(CH_2)_nNR^{16}R^{17}$; optionally substituted;

$R^{11}$ is selected from the group consisting of hydrogen, $C_1$-$C_6$-alkyl, —$CF_3$, $C_2$-$C_6$-alkenyl, $C_2$-$C_8$-alkynyl, —$(CH_2)_n$-cycloalkyl, —$(CH_2)_n$-aryl, —$(CH_2)_n$-heterocycloalkyl and —$(CH_2)_n$-heteroaryl; optionally substituted;

X is selected from the group consisting of $CH_2$, C(O), C(S), CH(OH), CH($OR^{16}$), $S(O)_2$, —$S(O)_2$—N(H)—, —$S(O)_2$—N($R^{16}$)—, —N(H)—$S(O)_2$—, —N($R^{16}$)—$S(O)_2$—, —C(=NH), —C(=N—$R^{16}$), CH($NH_2$), CH($NHR^{16}$), CH($NR^{16}R^{17}$), —C(O)—N(H)—, —C(O)—N($R^{16}$)—, —N(H)—C(O)—, —N($R^{16}$)—C(O)—, N(H), N(—$R^{16}$) and O;

$R^{12}$ is selected from the group consisting of $C_1$-$C_6$-alkyl, —$CF_3$, $C_2$-$C_6$-alkenyl, $C_2$-$C_8$-alkynyl, —$(CH_2)_n$-cycloalkyl, —$(CH_2)_n$-heterocycloalkyl, —$(CH_2)_n$-aryl, —$NR^{16}R^{17}$, and —$(CH_2)_n$-heteroaryl; optionally substituted;

$R^{16}$ and $R^{17}$ are independently selected from the group consisting of $C_1$-$C_6$-alkyl, $C_2$-$C_6$-alkenyl, $C_2$-$C_6$-alkynyl, —$(CH_2)_n$-cycloalkyl, —$(CH_2)_n$-aryl, —$CF_3$, —$C(O)R^{18}$ and —$S(O)_2R^{18}$; optionally substituted;

$R^{18}$ is independently selected from the group consisting of $C_1$-$C_6$-alkyl, $C_2$-$C_6$-alkenyl, $C_2$-$C_6$-lkynyl, —$(CH_2)_n$-cycloalkyl and —$CF_3$; optionally substituted; and n is in each instance selected from 0, 1 and 2.

In the context of WO2011/000566 the term "optionally substituted" in each instance refers to between 1 and 10 substituents, e.g. 1, 2, 3, 4, 5, 6, 7, 8, 9, or 10 substituents which are in each instance preferably independently selected from the group consisting of halogen, in particular F, Cl, Br or I; —NO$_2$, —CN, —OR', —NR'R'', —(CO)OR', —(CO)OR''', —(CO)NR'R'', —NR'COR'''', —NR'COR', —NR''CO NR'R'', —NR''SO$_2$A, —COR'''; —SO$_2$NR'R'', —OOCR''', —CR'''R''''OH, —R''''OH, =O, and -E;

R' and R'' are each independently selected from the group consisting of hydrogen, alkyl, alkenyl, alkynyl, —OE, cycloalkyl, heterocycloalkyl, aryl, heteroaryl, and aralkyl or together form a heteroaryl, or heterocycloalkyl; optionally substituted;

R''' and R'''' are each independently selected from the group consisting of alkyl, alkenyl, alkynyl, cycloalkyl, heterocycloalkyl, alkoxy, aryl, aralkyl, heteroaryl, and —NR'R''; and E is selected from the group consisting of alkyl, alkenyl, cycloalkyl, alkoxy, alkoxyalkyl, heterocycloalkyl, an alicyclic system, aryl and heteroaryl; optionally substituted.

Widespread resistance to both classes of licensed influenza antivirals (M2 ion channel inhibitors (adamantanes) and neuraminidase inhibitors (Oseltamivir)) occurs in both pandemic and seasonal viruses, rendering these drugs to be of marginal utility in the treatment modality. For M2 ion channel inhibitors, the frequency of viral resistance has been increasing since 2003 and for seasonal influenza A/H3N2, adamantanes are now regarded as ineffective. Virtually all 2009 H1N1 and seasonal H3N2 strains are resistant to the adamantanes (rimantadine and amantadine), and the majority of seasonal H1N1 strains are resistant to oseltamivir, the most widely prescribed neuraminidase inhibitor (NAI). For oseltamivir the WHO reported on significant emergence of influenza A/H1N1 resistance starting in the influenza season 2007/2008; and for the second and third quarters of 2008 in the southern hemisphere. Even more serious numbers were published for the fourth quarter of 2008 (northern hemisphere) where 95% of all tested isolates revealed no Oseltamivir-susceptibility. Considering the fact that now most national governments have been stockpiling Oseltamivir as part of their influenza pandemic preparedness plan, it is obvious that the demand for new, effective drugs is growing significantly. To address the need for more effective therapy, preliminary studies using double or even triple combinations of antiviral drugs with different mechanisms of action have been undertaken. Adamantanes and neuraminidase inhibitors in combination were analysed in vitro and in vivo and found to act highly synergistically. However, it is known that for both types of antivirals resistant viruses emerge rather rapidly and this issue is not tackled by combining these established antiviral drugs.

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. These two targets are located within distinct subunits of the polymerase complex and thus represent unique drug targets. Due to the fact that both functions are required for the so-called "cap-snatching" mechanism mandatory for viral transcription, concurrent inhibition of both functions is expected to act highly synergistically. This highly efficient drug combination would result in lower substance concentrations and hence improved dose-response-relationships and better side effect profiles.

Both of these active sites are composed of identical residues in all influenza A strains (e.g., avian and human) and hence this high degree of sequence conservation underpins the perception that these targets are not likely to trigger rapid resistant virus generation. Thus, endonuclease and cap-binding inhibitors individually and in combination are ideal drug candidates to combat both seasonal and pandemic influenza, irrespectively of the virus strain.

The combination of an endonuclease inhibitor and a cap-binding inhibitor or a dual specific polymerase inhibitor targeting both the endonuclease active site and the cap-binding domain would be effective against virus strains resistant against adamantanes and neuraminidase inhibitors and moreover combine the advantage of low susceptibility to resistance generation with activity against a broad range of virus strains.

(ii) The combination of inhibitors of different antiviral targets (particularly targeting influenza) focusing on the combination with (preferably influenza) polymerase inhibitors as dual or multiple combination therapy. Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of a different antiviral target is expected to act highly synergistically. This is based on the fact that these different types of antiviral drugs exhibit completely different mechanisms of action and pharmacokinetics properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the first group of polymerase inhibitors is combined with at least one compound selected from the second group of polymerase inhibitors.

The first group of polymerase inhibitors which can be used in this type of combination therapy includes, but is not limited to, the compounds having the formula (A) or (C).

The second group of polymerase inhibitors which can be used in this type of combination therapy includes, but is not limited to, the compounds having the general formula (I), the compounds having the general formula (II), the compounds disclosed in WO 2011/000566, WO 2010/110231, WO 2010/110409, WO 2006/030807 or U.S. Pat. No. 5,475,109 as well as flutimide and analogues, favipiravir and analogues, epigallocatechin gallate and analogues, as well as nucleoside analogs such as ribavirine.

(iii) The combination of polymerase inhibitors with neuramidase inhibitors

Influenza virus polymerase inhibitors are novel drugs targeting the transcription activity of the polymerase.

Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of a different extracellular antiviral target, especially the (e.g., viral) neuraminidase is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the above mentioned first group of polymerase inhibitors is combined with at least one neuramidase inhibitor.

The neuraminidase inhibitor (particularly influenza neuramidase inhibitor) is not specifically limited. Examples include zanamivir, oseltamivir, peramivir, KDN DANA, FANA, and cyclopentane derivatives.

(iv) The combination of polymerase inhibitors with M2 channel inhibitors

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of a different extracellular and cytoplasmic antiviral target, especially the viral M2 ion channel, is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the above mentioned first group of polymerase inhibitors is combined with at least one M2 channel inhibitor.

The M2 channel inhibitor (particularly influenza M2 channel inhibitor) is not specifically limited. Examples include amantadine and rimantadine.

(v) The combination of polymerase inhibitors with alpha glucosidase inhibitors

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target, with an inhibitor of a different extracellular target, especially alpha glucosidase, is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the above-mentioned first group of polymerase inhibitors is combined with at least one alpha glucosidase inhibitor.

The alpha glucosidase inhibitor (particularly influenza alpha glucosidase inhibitor) is not specifically limited. Examples include the compounds described in Chang et al., Antiviral Research 2011, 89, 26-34.

(vi) The combination of polymerase inhibitors with ligands of other influenza targets Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of different extracellular, cytoplasmic or nucleic antiviral targets is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles.

Moreover, advantages described under (i) for polymerase inhibitors would prevail for combinations of inhibitors of different antiviral targets with polymerase inhibitors.

Typically at least one compound selected from the above mentioned first group of polymerase inhibitors is combined with at least one ligand of another influenza target.

The ligand of another influenza target is not specifically limited. Examples include compounds acting on the sialidase fusion protein, e.g. Fludase (DAS181), siRNAs and phosphorothioate oligonucleotides, signal transduction inhibitors (ErbB tyrosine kinase, Abl kinase family, MAP kinases, PKCa-mediated activation of ERK signaling as well as interferon (inducers).

(vii) The combination of (preferably influenza) polymerase inhibitors with a compound used as an adjuvance to minimize the symptoms of the disease (antibiotics, anti-inflammatory agents like COX inhibitors (e.g., COX-1/COX-2 inhibitors, selective COX-2 inhibitors), lipoxygenase inhibitors, EP ligands (particularly EP4 ligands), bradykinin ligands, and/or cannabinoid ligands (e.g., CB2 agonists). Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an compound used as an adjuvance to minimize the symptoms of the disease address the causative and symptomatic pathological consequences of viral infection. This combination is expected to act synergistically because these different types of drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Compounds Having the General Formula (C)

The compounds having the general formula (C) are identified in the following.

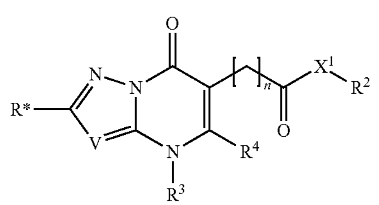

(C)

It is understood that throughout the present specification the term "a compound having the general formula (C)" encompasses pharmaceutically acceptable salts, solvates, polymorphs, prodrugs, tautomers, racemates, enantiomers, or diastereomers or mixtures thereof unless mentioned otherwise.

In the present invention the following definitions apply with respect to the compounds having the general formula (C).

V is N, or $CR^6$.

$X^1$ is O, S, or $NR^B$, preferably $X^1$ is O.

$X^2$ is $NR^5$, $N(R^5)C(O)$, $C(O)NR^5$, O, C(O), C(O)O, OC(O); S, SO, $SO_2$, $SO_2N(R^5)$ or $N(R^5)SO_2$. Preferably, $X^2$ is $NR^5$ or $N(R^5)SO_2$.

R* is —H, —Hal, (optionally substituted $C_{1-6}$ alkyl), (optionally substituted mono- or polycyclic group containing 3 to 20 carbon atoms and optionally 1 to 4 heteroatoms selected from O, N and S), —$C_{1-4}$ alkyl (optionally substituted mono- or polycyclic group containing 3 to 20 carbon atoms and optionally 1 to 4 heteroatoms selected from O, N and S), or —$X^2$—$R^1$. Preferably R* is H, -(optionally substituted $C_{1-6}$ alkyl), (optionally substituted $C_{3-7}$ cycloalkyl) or $X^2$—$R^1$.

$R^1$ is —H, -(optionally substituted $C_{1-6}$ alkyl), (optionally substituted mono- or polycyclic group containing 3 to 20 carbon atoms and optionally 1 to 4 heteroatoms selected from O, N and S), —$C_{1-4}$ alkyl(optionally substituted mono- or polycyclic group containing 3 to 20 carbon atoms and optionally 1 to 4 heteroatoms selected from O, N and S). Preferably $R^1$ is $C_{1-4}$ alkyl(optionally substituted mono- or polycyclic group containing 3 to 20 carbon atoms and optionally 1 to 4 heteroatoms selected from O, N and S).

$R^2$ is —H, (optionally substituted $C_{1-6}$ alkyl), (optionally substituted $C_{3-7}$ cycloalkyl), (optionally substituted aryl), —$C_{1-4}$ alkyl(optionally substituted $C_{3-7}$ cycloalkyl), or —$C_{1-4}$ alkyl(optionally substituted aryl) or if $X^1$ is NR' then $R^2$ can also be —OH. Preferably, $R^2$ is —H or —$C_{1-6}$ alkyl.

$R^3$ is —H, —$R^7$, or —$X^2$—$R^7$. Preferably $R^3$ is —H, —$C_{1-4}$ alkyl(optionally substituted aryl) or —$SO_2$—$R^5$. Preferably $R^3$ is —H.

$R^4$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl). Preferably, $R^4$ is —H, or -(optionally substituted $C_{1-6}$ alkyl).

$R^5$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl). Preferably $R^5$ is —$C_{1-4}$ alkyl-(optionally substituted aryl) or -(optionally substituted $C_{3-7}$ cycloalkyl).

$R^6$H, —$C_{1-6}$ alkyl, aryl, halogen or CN. Preferably, $R^6$ is H or -aryl.

$R^7$ is -(optionally substituted hydrocarbon group which contains from 5 to 20 carbon atoms and optionally 1 to 4 heteroatoms selected from O, N and S and which contains at least one ring). Preferably, $R^7$ is —$C_{1-4}$ alkyl-(optionally substituted aryl).

$R^8$ is —H, —$C_{1-6}$ alkyl or —$C_{1-4}$ alkyl-(optionally substituted aryl). Preferably, $R^8$ is —$C_{1-6}$ alkyl or —$C_{1-4}$ alkyl(optionally substituted aryl).

n is 0 to 4, preferably 0 or 1.

The optional substituent of the alkyl group can be selected from the group consisting of halogen, —CN, —$NR^5R^5$, —OH, and —O—$C_{1-6}$ alkyl.

The optional substituent of the cycloalkyl group, the aryl group, the mono- or polycyclic group or the hydrocarbon group can be selected from the group consisting of —$C_{1-6}$ alkyl, halogen, —$CF_3$, —CN, —$X^2$—$C_{1-6}$ alkyl and —$C_{1-6}$ alkyl-aryl.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention as indicated by the appended claims in any way.

EXAMPLES

FRET Endonuclease Activity Assay

The influenza A virus (IAV) PA-Nter fragment (amino acids 1-209) harbouring the influenza endonuclease activity was generated and purified as described in Dias et al., Nature 2009; April 16; 458(7240), 914-918. The protein was dissolved in buffer containing 20 mM Tris pH 8.0, 100 mM NaCl and 10 mM β-mercaptoethanol and aliquots were stored at −20° C.

A 20 bases dual-labelled RNA oligo with 5'-FAM fluorophore and 3'-BHQ1 quencher was used as a substrate to be cleaved by the endonuclease activity of the PA-Nter. Cleavage of the RNA substrate frees the fluorophore from the quencher resulting in an increase of the fluorescent signal.

All assay components were diluted in assay buffer containing 20 mM Tris-HCl pH 8.0, 100 mM NaCl, 1 mM $MnCl_2$, 10 mM $MgCl_2$ and 10 mM 3-mercaptoethanol. The final concentration of PA-Nter was 0.5 µM and 1.6 µM RNA substrate. The test compounds were dissolved in DMSO and generally tested at two concentrations or a concentration series resulting in a final plate well DMSO concentration of 0.5%. In those cases where the compounds were not soluble at that concentration, they were tested at the highest soluble concentration. SAV-6004 was used as a reference in the assay at a concentration of 0.1 µM.

5 µl of each compound dilution was provided in the wells of white 384-well microtiter plates (PerkinElmer) in eight replicates. After addition of PA-Nter dilution, the plates were sealed and incubated for 30 min at room temperature prior to the addition of 1.6 µM RNA substrate diluted in assay buffer. Subsequently, the increasing fluorescence signal of cleaved RNA was measured in a microplate reader (Synergy HT, Biotek) at 485 nm excitation and 535 nm emission wavelength. The kinetic read interval was 35 sec at a sensitivity of 35. Fluorescence signal data over a period of 20 min were used to calculate the initial velocity (v0) of substrate cleavage. Final readout was the % reduction of v0 of compound-treated samples compared to untreated. The half maximal inhibitory concentration ($IC_{50}$) is a measure of the effectiveness of a compound in inhibiting biological or biochemical function and was calculated from the initial reaction velocities (v0) in a given concentration series ranging from maximum 100 µM to at least 2 nM.

Cytopathic Effect (CPE) Assay

The influenza A virus (IAV) was obtained from American Tissue Culture Collection (A/Aichi/2/68 (H3N2); VR-547). Virus stocks were prepared by propagation of virus on Mardin-Darby canine kidney (MDCK; ATCC CCL-34) cells and infectious titres of virus stocks were determined by the 50% tissue culture infective dose ($TCID_{50}$) analysis as described in Reed, L. J., and H. Muench. 1938, Am. J. Hyg. 27:493-497.

MDCK cells were seeded in 96-well plates at $2 \times 10^4$ cells/well using DMEM/Ham's F-12 (1:1) medium containing 10% foetal bovine serum (FBS), 2 mM L-glutamine and 1% antibiotics (all from PAA). Until infection the cells were incubated for 5 hrs at 37° C., 5.0% $CO_2$ to form a 80% confluent monolayer on the bottom of the well. Each test compound was dissolved in DMSO and generally tested at 25 µM and 250 µM. In those cases where the compounds were not soluble at that concentration they were tested at the highest soluble concentration. The compounds were diluted in infection medium (DMEM/Ham's F-12 (1:1) containing 5 µg/ml trypsin, and 1% antibiotics) for a final plate well DMSO concentration of 1%. The virus stock was diluted in infection medium (DMEM/Ham's F-12 (1:1) containing 5 µg/ml Trypsin, 1% DMSO, and 1% antibiotics) to a theoretical multiplicity of infection (MOI) of 0.05.

After removal of the culture medium and one washing step with PBS, virus and compound were added together to the cells. In the wells used for cytotoxicity determination (i.e. in the absence of viral infection), no virus suspension was added. Instead, infection medium was added. Each treatment was conducted in two replicates. After incubation at 37° C., 5% $CO_2$ for 48 hrs, each well was observed microscopically for apparent cytotoxicity, precipitate formation, or other notable abnormalities. Then, cell viability was determined using CellTiter-Glo luminescent cell viability assay (Promega). The supernatant was removed carefully and 65 µl of the reconstituted reagent were added to each well and incubated with gentle shaking for 15 min at room temperature. Then, 60 µl of the solution was transferred to an opaque plate and luminescence (RLU) was measured using Synergy HT plate reader (Biotek).

Relative cell viability values of uninfected-treated versus uninfected-untreated cells were used to evaluate cytotoxicity of the compounds. Substances with a relative viability below 80% at the tested concentration were regarded as cytotoxic and retested at lower concentrations.

Reduction in the virus-mediated cytopathic effect (CPE) upon treatment with the compounds was calculated as follows: The response (RLU) of infected-untreated samples was subtracted from the response (RLU) of the infected-treated samples and then normalized to the viability of the corresponding uninfected sample resulting in % CPE reduction. The half maximal inhibitory concentration ($IC_{50}$) is a measure of the effectiveness of a compound in inhibiting biological or biochemical function and was calculated from the RLU response in a given concentration series ranging from maximum 100 µM to at least 100 nM.

Compounds Having the General Formula (A)

Scheme I Series:
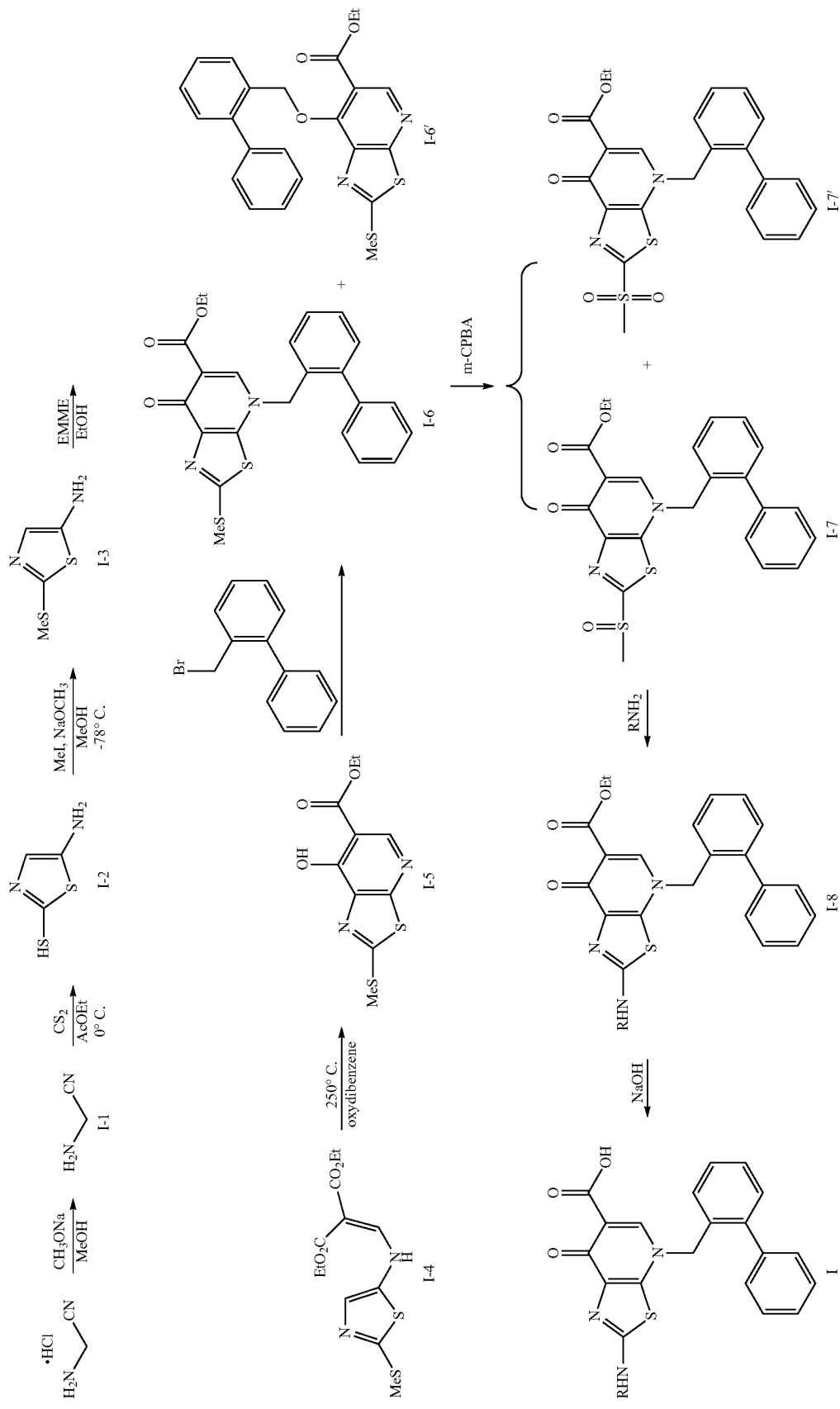

General Procedure:
Synthesis of 2-Aminoacetonitrile (I-1) and 5-Aminothiazole-2-Thiol (I-2)

A solution of sodium methoxide, prepared from sodium (23 g, 1.0 mol) in dry methanol (500 mL), was added dropwise under ice-cooling to a stirred suspension of aminoacetonitrile hydrochloride (100 g, 1.08 mol) in dry methanol (100 mL). This reaction mixture was stirred for 2 hours at room temperature (r.t.), then the mixture was concentrated in vacuo, the residue was dissolved in dry ethyl acetate (500 mL), the mixture was filtered and the filtrate was dropwise added to the solution of carbon disulfide (136 g, 1.79 mol) in dry ethyl acetate (100 mL). The reaction mixture was stirred for overnight while the temperature rose from 0° C. to room temperature. The precipitate was filtered to afford the crude product I-2 as yellow solid 107.4 g, yield 75.6%.

Synthesis of 2-Aminoacetonitrile (I-3)

A solution of sodium methoxide, prepared from sodium (18.7 g, 0.814 mol) in dry methanol (600 ml), was cooled to −78° C., compound I-2 was added at −78° C. To this red-brown solution, methyl iodide (115 g, 0.814 mmol) was dropwise added at −78° C. This reaction mixture was stirred for 3 h at −78° C. The methanol was removed in vacuo and the residue was extracted with ethyl acetate (EA) and water, the organic phase was dried and concentrated in vacuo to afford the crude product I-3 as brown oil 117 g, yield 98%.

Synthesis of 2-Aminoacetonitrile (I-4)

The compound I-3 (117 g, 0.801 mmol) was dissolved in ethanol (400 ml) and diethyl ethoxymethylenemalonate was added. This reaction mixture was stirred for 3 h at reflux. Then the mixture was cooled to r.t. The precipitate was filtered to afford the product I-4 as brown solid 163 g, yield 64%.

Synthesis of 2-Aminoacetonitrile (I-5)

The compound I-4 (20 g, 63.6 mmol) was added to diphenyl ether (150 mL). The mixture was heated to 250° C. for 40 min. Then the mixture was cooled to r.t. and was added to petrolether (PE). The precipitate was filtered to afford the product I-5 as brown solid 16 g, yield 94%.

Synthesis of 2-Aminoacetonitrile (I-6)

The compound I-5 (6.5 g, 24.07 mmol), 2-(bromomethyl)biphenyl (6.5 g, 26.48 mmol) and potassium carbonate (6.6 g, 48.14 mmol) were added to methylsulfinylmethane (60 mL). This reaction mixture was stirred for overnight at r.t. The mixture was extracted with EA and water, the organic phase was concentrated in vacuo to afford the crude product which was purified by column chromatography on silica gel with EA to afford the product I-6 as brown solid 7.4 g, yield 70.5%.

Synthesis of 2-Aminoacetonitrile (I-7)

The compound I-6 (3.1 g, 0.711 mmol) and m-CPBA (3.0 g, 17.775 mmol) were added to dichloromethane (DCM) (20 mL). This reaction mixture was stirred for 5 h at r.t. The mixture was extracted with DCM and a saturated $NaHCO_3$ solution. The organic phase was concentrated in vacuo to afford the crude product I-7 as yellow solid 3.2 g, yield 97%.

Representative Synthetic Method of 2-Aminoacetonitrile ($I_4$-8)

The compound I-7 (200 mg, 0.427 mmol), phenylmethanamine (183 mg, 1.709 mmol) and potassium carbonate (118 mg, 0.854 mmol) were added to dimethylsulfoxide (DMSO) (3 mL). This reaction mixture was stirred overnight at r.t. This mixture was extracted with DCM and water, the organic phase was concentrated in vacuo to afford the crude product I-8 as brown oil 180 mg, yield 85%.

Representative Synthetic Method of 2-Aminoacetonitrile ($I_4$)

The compound $I_4$-8 (62 mg, 0.125 mmol) was dissolved in EtOH (6 mL), then lithium hydroxide hydrate (21 mg, 0.501 mmol) was added. This reaction mixture was stirred for 4 h at r.t. The mixture was adjusted to pH=5 with HCl, the precipitate was filtered to afford the product $I_4$ as pale white solid 32 mg, yield 55%.

Example 1

4-(Biphenyl-2-ylmethyl)-7-oxo-2-(phenylsulfonamido)-4,7-dihydrothiazolo[5,4-b]pyridine-6-carboxylic acid (F4)

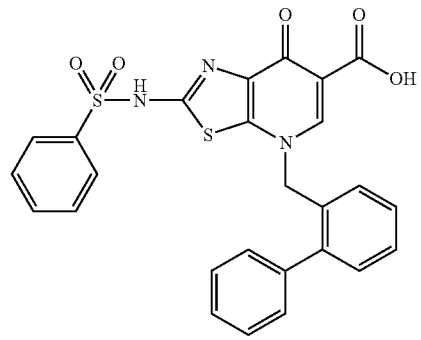 [SMILES: O=C(O)c1cn(Cc2ccccc2-c2ccccc2)c2sc(NS(=O)(=O)c3ccccc3)nc2c1=O]

I-7 (I-7') was treated with phenylsulfonamide according to the representative method to obtain compound F4 as a pale white solid.
Yield: 5%
MS (ESI): 518(M+H)$^+$, 105
$^1$H NMR ($d_6$-DMSO, 300 Hz):
δ 8.46 (br, s, 1H), 7.34-7.73 (m, 14H), 5.35 (s, 2H)

Example 2

4-(Biphenyl-2-ylmethyl)-2-(methylamino)-7-oxo-4,7-dihydrothiazolo[5,4-b]pyridine-6-carboxylic acid (I1)

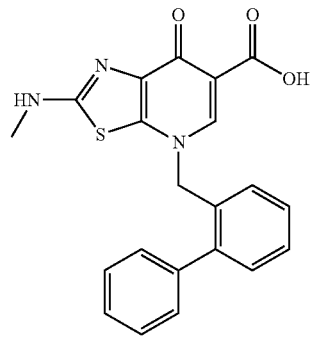 [SMILES: CNc1nc2c(=O)c(C(=O)O)cn(Cc3ccccc3-c3ccccc3)c2s1]

I-7 (I-7') was treated with methanamine according to the representative method to obtain compound I1 as a pale white solid.
Yield: 5%
MS (ESI): 392 (M+H)$^+$, 157
$^1$H NMR ($d_6$-DMSO, 300 Hz):

δ 8.39 (s, 1H), 8.06-8.07 (br, s, 1H), 7.23-7.51 (m, 9H), 5.58 (s, 2H), 2.84 (d, J=4.8 Hz, 3H)

Example 3

4-(Biphenyl-2-ylmethyl)-2-(cyclopropylamino)-7-oxo-4,7-dihydrothiazolo[5,4-b]pyridine-6-carboxylic acid (I2)

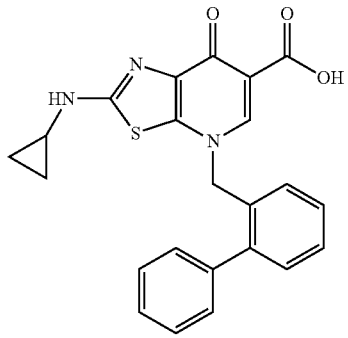 [SMILES: O=C(O)c1cn(Cc2ccccc2-c2ccccc2)c2sc(NC3CC3)nc2c1=O]

I-7 (I-7') was treated with aminocyclopropane according to the representative method to obtain compound 12 as a pale white solid.
Yield: 5%
MS (ESI): 418 (M+H)$^+$
1HNMR (d6-DMSO, 300 MHz):
δ 8.59 (s, 1H), 8.48 (s, 1H), 7.49-7.25 (m, 9H), 5.59 (s, 2H), 2.57 (d, J=1.8 Hz, 1H), 0.72 (m, 2H), 0.47 (m, 2H).

Example 4

4-(Biphenyl-2-ylmethyl)-2-(cyclopentylamino)-7-oxo-4,7-dihydrothiazolo[5,4-b]pyridine-6-carboxylic acid (I3)

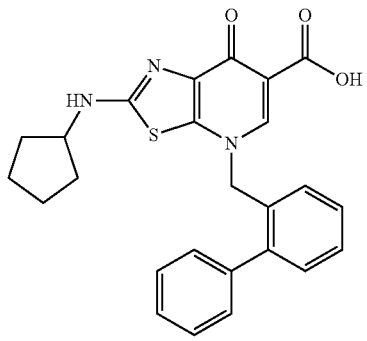 [SMILES: O=C(O)c1cn(Cc2ccccc2-c2ccccc2)c2sc(NC3CCCC3)nc2c1=O]

I-7 (I-7') was treated with aminocyclopentane according to the representative method to obtain compound 13 as a yellow solid.
Yield: 5%
MS (ESI): 446 (M+H)$^+$, 407
$^1$HNMR (d$_6$-DMSO, 300 MHz):
δ 8.42 (s, 1H), 8.16 (d, J=6.0 Hz, 1H), 7.48-7.24 (m, 10H), 5.57 (s, 2H), 4.03 (d, J=6.0 Hz, 2H), 1.89-1.85 (m, 2H), 1.63-1.41 (m, 7H)

Example 5

2-(Benzylamino)-4-(biphenyl-2-ylmethyl)-7-oxo-4,7-dihydrothiazolo[5,4-b]pyridine-6-carboxylic acid (I4)

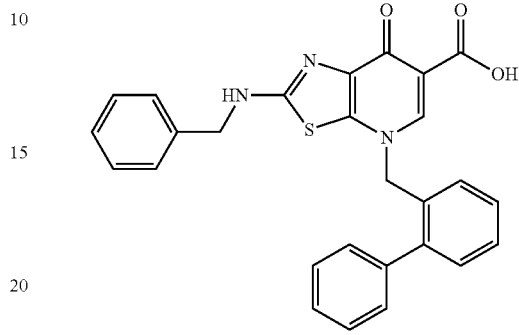

I-7 (I-7') was treated with benzylamine according to the representative method to obtain compound I4 as a pale white solid.
Yield: 5%
MS (ESI): 468 (M+H)$^+$
$^1$HNMR (d$_6$-DMSO, 300 MHz):
δ 8.60 (s, 1H), 8.43 (s, 1H), 7.48-7.25 (m, 14H), 5.57 (s, 2H), 4.49 (d, J=4.5 Hz, 2H)

Example 6

4-(Biphenyl-2-ylmethyl)-7-oxo-2-(pyrrolidin-1-yl)-4,7-dihydrothiazolo[5,4-b]pyridine-6-carboxylic acid (I5)

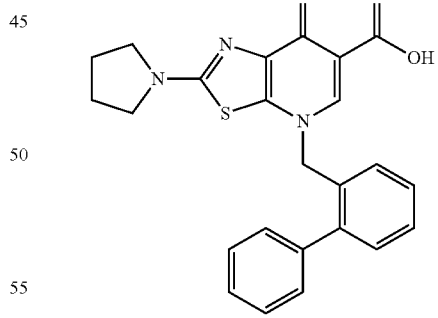

I-7 (I-7') was treated with pyrrolidine according to the representative method to obtain compound 15 as a pale white solid.
Yield: 5%
MS (ESI): 433 (M+H)$^+$
$^1$HNMR (d$_6$-DMSO, 300 MHz):
δ 8.43 (s, 1H), 7.50-7.269 (m, 9H), 5.54 (d, J=8.4 Hz, 2H), 3.32 (s, 5H), 1.95 (s, 4H)

Example 7

4-(Biphenyl-2-ylmethyl)-2-(4-hydroxypiperidin-1-yl)-7-oxo-4,7-dihydrothiazolo[5,4-b]pyridine-6-carboxylic acid (I6)

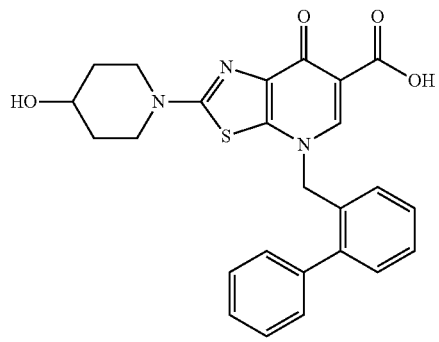 [SMILES: O=C(O)c1cn(Cc2ccccc2-c2ccccc2)c2sc(N3CCC(O)CC3)nc2c1=O]

I-7 (I-7') was treated with piperidin-4-ol according to the representative method to obtain compound 16 as a yellow solid.

Yield: 3%

MS (ESI): 462 (M+H)$^+$ $^1$HNMR (d$_6$-DMSO, 300 MHz):

δ 16.20 (br, s, 1H), 8.45 (s, 1H,), 7.51-7.23 (m, 10H), 5.55 (d, J=7.8 Hz, 2H), 3.76-3.21 (m, 7H), 1.70-1.78 (m, 2H), 1.39-1.48 (m, 2H)

Example 8

4-(Biphenyl-2-ylmethyl)-7-oxo-2-(piperazin-1-yl)-4,7-dihydrothiazolo[5,4-b]pyridine-6-carboxylic acid (I7)

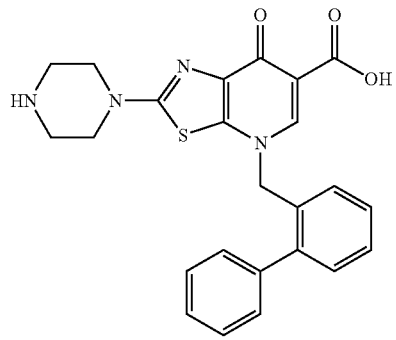 [SMILES: O=C(O)c1cn(Cc2ccccc2-c2ccccc2)c2sc(N3CCNCC3)nc2c1=O]

I-7 (I-7') was treated with piperazine according to the representative method to obtain compound 17 as a yellow solid.

Yield: 3%

MS (ESI): 447 (M+H)$^+$ $^1$HNMR (d$_6$-DMSO, 300 MHz):

δ 9.07 (s, 2H), 8.52 (s, 1H), 7.49-7.23 (m, 10H), 5.61 (s, 2H), 3.63 (s, 4H), 3.22 (s, 4H)

Example 9

2-(4-Benzylpiperazin-1-yl)-4-(biphenyl-2-ylmethyl)-7-oxo-4,7-dihydrothiazolo[5,4-b]pyridine-6-carboxylic acid (I8)

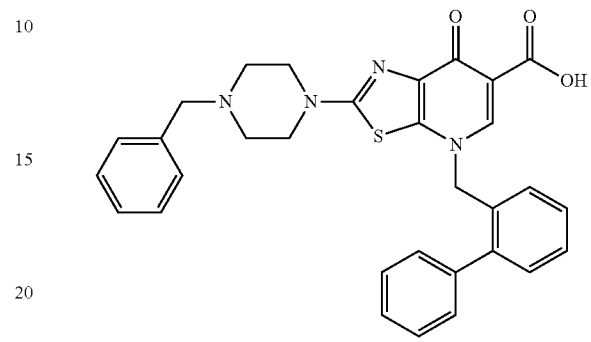

I-7 (I-7') was treated with 1-benzylpiperazine according to the representative method to obtain compound 18 as a yellow solid.

Yield: 5%

MS (ESI): 537 (M+H)$^+$ $^1$HNMR (d$_6$-DMSO, 300 MHz):

δ 8.55 (s, 1H), 7.49-7.22 (m, 14H), 5.61 (s, 2H), 4.30 (s, 2H), 3.16-3.39 (m, 8H)

Example 10

4-(Biphenyl-2-ylmethyl)-7-oxo-2-(piperidin-1-yl)-4,7-dihydrothiazolo[5,4-b]pyridine-6-carboxylic acid (I9)

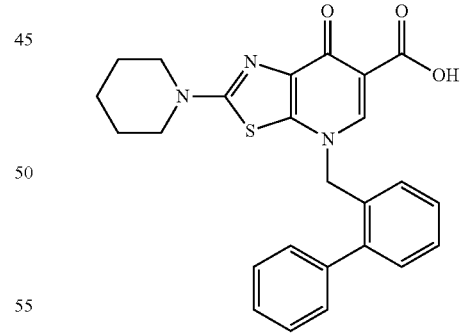

I-7 (I-7') was treated with piperidine according to the representative method to obtain compound 19 as a pale white solid.

Yield: 5%

MS (ESI): 446 (M+H)$^+$ $^1$HNMR (d$_6$-DMSO, 300 MHz):

δ 16.22 (s, 1H), 8.45 (s, 1H), 7.49-7.24 (m, 9H), 5.58 (s, 2H), 3.41-3.42 (m, 4H), 1.57 (s, 6H)

Example 11

4-(Biphenyl-2-ylmethyl)-2-(4-methylpiperidin-1-yl)-7-oxo-4,7-dihydrothiazolo[5,4-b]pyridine-6-carboxylic acid (I10)

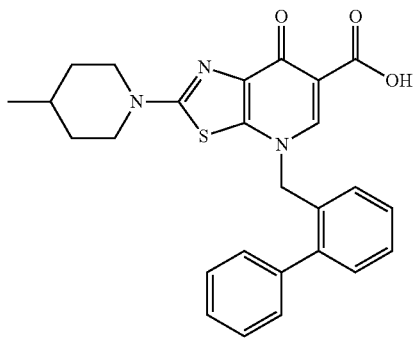 [SMILES: CC1CCN(c2nc3c(=O)c(C(=O)O)cn(Cc4ccccc4-c4ccccc4)c3s2)CC1]

I-7 (I-7') was treated with 4-methylpiperidine according to the representative method to obtain compound I10 as a pale white solid.

Yield: 5%

MS (ESI): 460 (M+H)$^+$ $^1$H NMR (d$_6$-DMSO, 300 MHz):

δ 8.44 (s, 1H), 7.25-7.51 (m, 9H), 5.58 (s, 2H), 3.67-3.71 (m, 2H), 3.02-3.10 (t, J=12 Hz, 2H), 1.57-1.70 (m, 3H) 1.11-1.17 (m, 2H), 0.90 (d, J=6.9 Hz, 3H)

Example 12

4-(Biphenyl-2-ylmethyl)-2-(isopropylamino)-7-oxo-4,7-dihydrothiazolo[5,4-b]pyridine-6-carboxylic acid (I11)

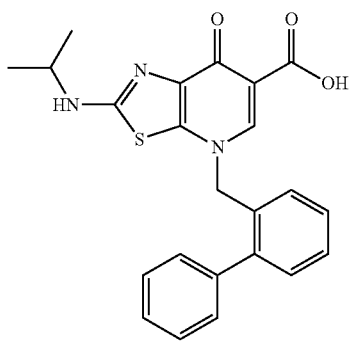 [SMILES: CC(C)Nc1nc2c(=O)c(C(=O)O)cn(Cc3ccccc3-c3ccccc3)c2s1]

I-7 (I-7') was treated with 2-aminopropane according to the representative method to obtain compound I11 as a yellow solid.

Yield: 5%

MS (ESI): 420 (M+H)$^+$, 105

$^1$H NMR (d$_6$-DMSO, 300 MHz):

δ 8.42 (s, 1H), 8.06 (d, J=7.2 Hz, 1H), 7.23-7.51 (m, 9H), 5.56 (s, 2H), 3.85-3.91 (m, 1H), 1.13 (d, J=6.6 Hz, 6H)

Example 13

4-(Biphenyl-2-ylmethyl)-2-(2-methoxyethylamino)-7-oxo-4,7-dihydrothiazolo[5,4-b]pyridine-6-carboxylic acid (I12)

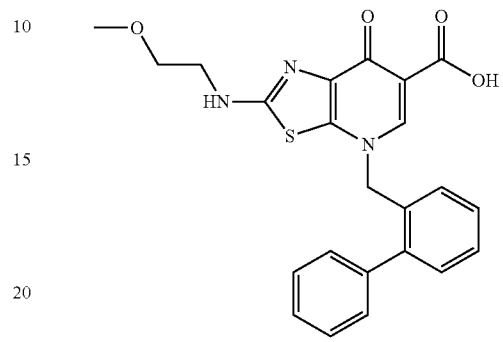

I-7 (I-7') was treated with 2-methoxyethanamine according to the representative method to obtain compound I12 as a pale white solid.

Yield: 5%

MS (ESI): 436 (M+H)$^+$

1H NMR (d$_6$-DMSO, 300 MHz):

δ 8.43 (s, 1H), 8.25 (s, 1H), 7.23-7.51 (m, 9H), 5.57 (s, 2H), 3.45-3.50 (m, 4H), 3.25 (s, 3H)

Example 14

4-(Biphenyl-2-ylmethyl)-2-(4-methyl piperazin-1-yl)-7-oxo-4,7-dihydrothiazolo[5,4-b]pyridine-6-carboxylic acid (I14)

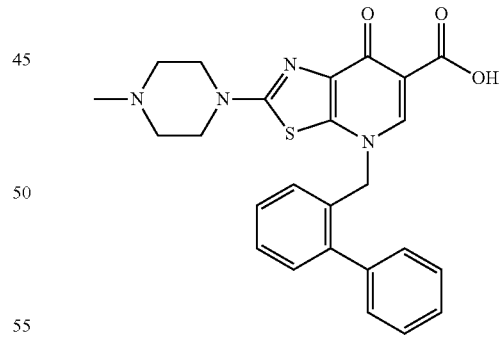

I-7 (I-7') was treated with 1-methylpiperazine according to the representative method to obtain compound I14 as a yellow solid.

Yield: 2%

MS (ESI): 461 (M+H)$^+$, 157, 231

$^1$H NMR (d$_6$-DMSO, 300 MHz):

δ 9.89 (s, 1H), 8.54 (s, 1H), 7.21-7.49 (m, 9H), 5.62 (s, 2H), 3.94-3.97 (br, 2H), 3.33-3.48 (m, 4H), 3.12-3.17 (m, 2H), 2.84 (s, 3H).

Example 15

4-(Biphenyl-2-ylmethyl)-2-morpholino-7-oxo-4,7-dihydrothiazolo[5,4-b]pyridine-6-carboxylic acid (I15)

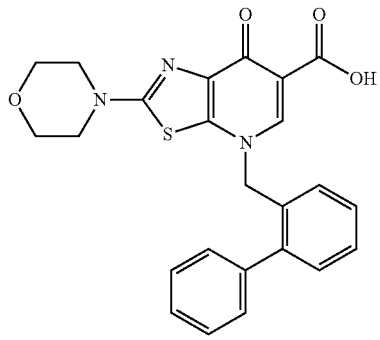 [SMILES: O=C(O)c1cn(Cc2ccccc2-c2ccccc2)c2sc(N3CCOCC3)nc2c1=O]

I-7 (I-7') was treated with morpholine according to the representative method to obtain compound I15 as a yellow solid.

Yield: 2%

MS (ESI): 448 (M+H)$^+$, 157

$^1$H NMR (d$_6$-DMSO, 300 MHz):

δ 8.41 (s, 1H), 7.24-7.48 (m, 9H), 5.59 (s, 2H), 3.66-3.68 (m, 4H), 3.40-3.41 (m, 4H)

Example 16

4-(Biphenyl-2-ylmethyl)-N-methyl-2-(methylamino)-7-oxo-4,7-dihydrothiazolo[5,4-b]pyridine-6-carboxamide (I16)

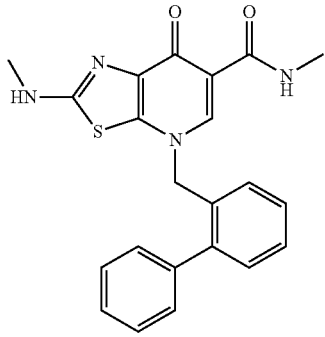

I-7 (I-7') was treated with methanamine according to the representative method to obtain compound I16 as a yellow solid.

Yield: 5%

MS (ESI): 405 (M+H)$^+$ $^1$H NMR (d$_6$-DMSO, 300 MHz):

δ 10.16 (br, s, 1H), 8.39 (s, 1H), 7.84 (br, s, 1H), 7.29-7.48 (m, 8H), 7.08-7.10 (d, J=6.9 Hz, 1H), 5.43 (s, 2H), 2.83 (s, 3H), 2.81 (s, 3H)

Example 17

2-(Benzylamino)-4-(biphenyl-2-ylmethyl)-N-methyl-7-oxo-4,7-dihydrothiazolo[5,4-b]pyridine-6-carboxamide (I17)

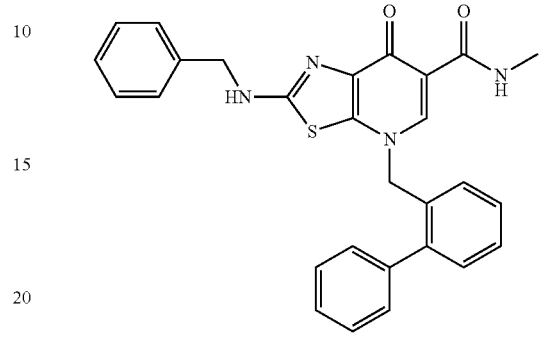

The ethyl ester precursor of I4 was treated with methanamine according to the representative method to obtain compound I17 as a pale white solid.

Yield: 5%

MS (ESI): 481 (M+H)$^+$ $^1$H NMR (d$_6$-DMSO, 300 MHz):

δ 10.15 (s, 1H), 8.41 (s, 1H), 8.37 (s, 1H), 7.68-7.72 (m, 1H), 7.28-7.48 (m, 13H), 7.09 (d, J=7.5 Hz, 1H), 5.42 (s, 2H), 4.45 (d, J=5.1 Hz, 2H), 2.82 (d, J=4.2 Hz, 3H)

Example 18

4-(Biphenyl-2-ylmethyl)-N-methyl-7-oxo-2-(pyrrolidin-1-yl)-4,7-dihydrothiazolo[5,4-b]pyridine-6-carboxamide (I18)

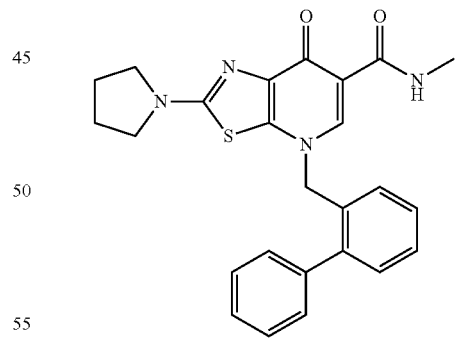

The ethyl ester precursor of I5 was treated with methanamine according to the representative method to obtain compound I18 as a pale white solid.

Yield: 5%

MS (ESI): 445 (M+H)$^+$, 157

$^1$H NMR (CDCl$_3$, 300 MHz):

δ 10.28 (s, 1H), 8.32 (s, 1H), 7.22-7.46 (m, 8H), 7.08 (d, J=7.8 Hz, 1H), 5.15 (s, 2H), 3.67 (s, 4H), 2.97 (d, J=4.5 Hz, 3H), 2.02 (s, 4H)

Example 19

N-Benzyl-2-(benzylamino)-4-(biphenyl-2-ylmethyl)-7-oxo-4,7-dihydrothiazolo[5,4-b]pyridine-6-carboxamide (I19)

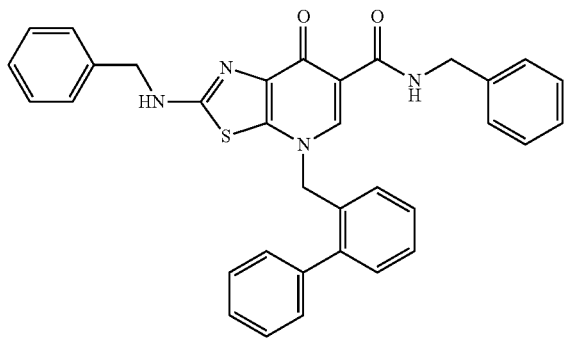 [SMILES: O=C(NCc1ccccc1)c1cn(Cc2ccccc2-c2ccccc2)c2sc(NCc3ccccc3)nc2c1=O]

I4 was treated with benzylamine according to the representative method to obtain compound I19 as a brown solid.

Yield: 2%

MS (ESI): 557 (M+H)$^+$, 105.

$^1$H NMR (d$_6$-DMSO, 300 MHz):

δ 10.75 (s, 1H), 8.42 (s, 1H), 8.39 (s, 1H), 7.25-7.46 (m, 18H), 7.14 (d, J=7.2 Hz, 1H), 5.44 (s, 2H), 4.52 (d, J=5.4 Hz, 2H), 4.44 (d, J=5.7 Hz, 2H)

Example 20

4-(Biphenyl-2-ylmethyl)-7-oxo-2-(phenylmethylsulfonamido)-4,7-dihydrothiazolo[5,4-]pyridine-6-carboxylic acid (I20)

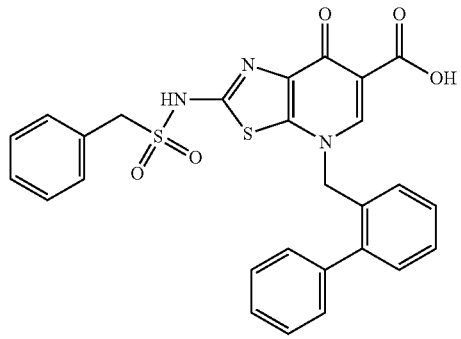 [SMILES: O=C(O)c1cn(Cc2ccccc2-c2ccccc2)c2sc(NS(=O)(=O)Cc3ccccc3)nc2c1=O]

I-7 (I-7') was treated with benzylsulfonamide according to the representative method to obtain compound I20 as a pale white solid.

Yield: 5%

MS (ESI): 532 (M+H)$^+$ $^1$H NMR (d$_6$-DMSO, 300 MHz):

δ 8.51 (s, 1H), 7.20-7.54 (m, 14H), 5.53 (s, 2H), 4.36 (s, 2H)

Example 21

4-(Biphenyl-2-ylmethyl)-2-(3-fluorophenylsulfonamido)-7-oxo-4,7-dihydrothiazolo[5,4-b]pyridine-6-carboxylic acid (I21)

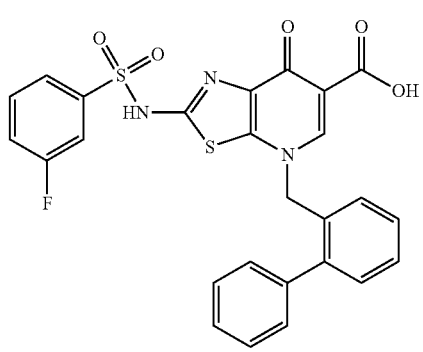 [SMILES: O=C(O)c1cn(Cc2ccccc2-c2ccccc2)c2sc(NS(=O)(=O)c3cccc(F)c3)nc2c1=O]

I-7 (I-7') was treated with 3-fluorobenzylsulfonamide according to the representative method to obtain compound I21 as a pale white solid.

Yield: 5%

MS (ESI): 286 (M+H)$^+$, 157, 105.

$^1$H NMR (d$_6$-DMSO, 300 MHz):

δ 8.53 (s, 1H), 7.24-7.57 (m, 13H), 5.63 (s, 2H)

Example 22

4-(Biphenyl-2-ylmethyl)-2-(methylsulfonamido)-7-oxo-4,7-dihydrothiazolo[5,4-b]pyridine-6-carboxylic acid (I22)

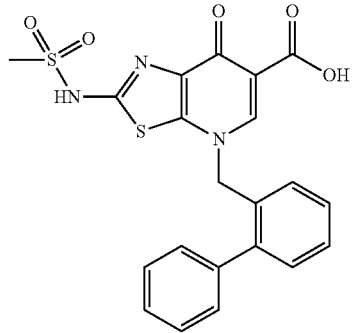 [SMILES: CS(=O)(=O)Nc1nc2c(=O)c(C(=O)O)cn(Cc3ccccc3-c3ccccc3)c2s1]

I-7 (I-7') was treated with methylsulfonamide according to the representative method to obtain compound I22 as a pale white solid.

Yield: 5%

MS (ESI): 456(M+H)$^+$ $^1$H NMR (d$_6$-DMSO, 300 MHz):

δ 8.55 (s, 1H), 7.26-7.50 (m, 9H), 5.60 (s, 2H), 2.96 (s, 3H)

Example 23

4-(Biphenyl-2-ylmethyl)-2-(2-chlorobenzylamino)-7-oxo-4,7-dihydrothiazolo[5,4-b]pyridine-6-carboxylic acid (I$_{1A}$)

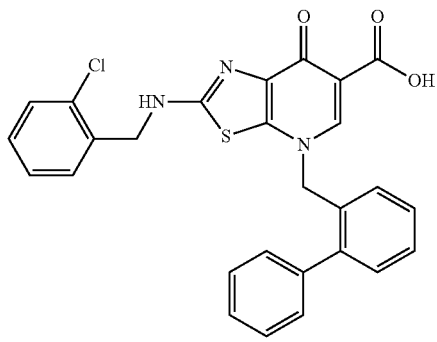 [SMILES: O=C(O)c1cn(Cc2ccccc2-c2ccccc2)c2sc(NCc3ccccc3Cl)nc2c1=O]

I-7 (I-7') was treated with 2-chlorobenzylamine according to the representative method to obtain compound I$_{1A}$ as a pale white solid.

Yield: 4%

MS (ESI): 502 (M+H)$^+$ $^1$H NMR (d$_6$-DMSO, 300 Hz):

δ 8.62 (br, s, 1H), 8.44 (s, 1H), 7.24-7.49 (m, 13H), 5.59 (s, 2H), 4.57 (d, J=3.9 Hz, 2H)

Example 24

Ethyl-4-(biphenyl-2-ylmethyl)-2-(2-chlorobenzylamino)-7-oxo-4,7-dihydrothiazolo[5,4-b]pyridine-6-carboxylate (I$_{1A}$-h)

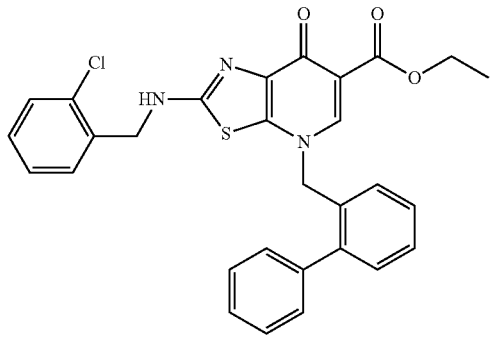 [SMILES: CCOC(=O)c1cn(Cc2ccccc2-c2ccccc2)c2sc(NCc3ccccc3Cl)nc2c1=O]

I-7 (I-7') was treated with 2-chlorobenzylamine according to the representative method to obtain compound I$_{1A}$-h as a pale white solid.

Yield: 4%

MS (ESI): 531(M+H)$^+$, 169

$^1$H NMR (d$_6$-DMSO, 400 Hz):

δ 8.31 (br, s, 1H), 8.07 (s, 1H), 7.20-7.46 (m, 13H), 5.36 (s, 2H), 4.51 (d, J=3.9 Hz, 2H), 4.16 (q, J=6.8 Hz, 2H), 1.26 (t, J=7.2 Hz, 3H)

Example 25

4-(Biphenyl-2-ylmethyl)-2-(3-chlorobenzylamino)-7-oxo-4,7-dihydrothiazolo[5,4-]pyridine-6-carboxylic acid (I$_{2A}$)

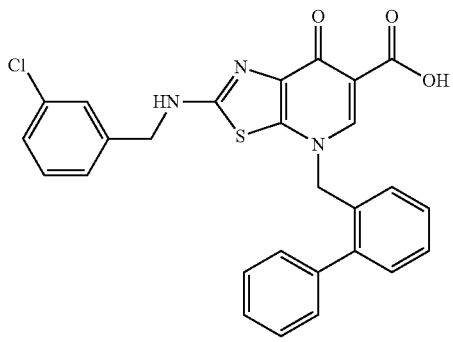 [SMILES: O=C(O)c1cn(Cc2ccccc2-c2ccccc2)c2sc(NCc3cccc(Cl)c3)nc2c1=O]

I-7 (I-7') was treated with 3-chlorobenzylamine according to the representative method to obtain compound I$_{2A}$ as a pale white solid.

Yield: 3%

MS (ESI): 502 (M+H)$^+$, 405

$^1$HNMR (d$_6$-DMSO, 400 MHz):

δ 8.64 (s, 1H), 8.44 (s, 1H), 7.50-7.23 (m, 13H), 5.59 (s, 2H), 4.51 (d, J=9.2 Hz, 2H).

Example 26

Ethyl 4-(biphenyl-2-ylmethyl)-2-(3-chlorobenzylamino)-7-oxo-4,7-dihydrothiazolo[5,4-b]pyridine-6-carboxylate (I$_{2A}$-h)

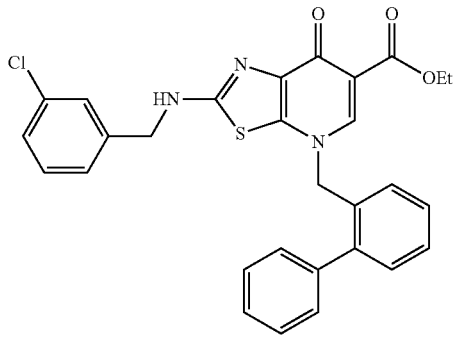 [SMILES: CCOC(=O)c1cn(Cc2ccccc2-c2ccccc2)c2sc(NCc3cccc(Cl)c3)nc2c1=O]

I-7 (I-7') was treated with 3-chlorobenzylamine according to the representative method to obtain compound I$_{2A}$-h as a pale white solid.

Yield: 4%

MS (ESI): 530 (M+H)$^+$ $^1$HNMR (d$_6$-DMSO, 400 MHz):

δ 8.39 (s, 1H), 8.10 (s, 1H), 7.48-7.21 (m, 13H), 5.39 (s, 2H), 4.47 (d, J=4.4 Hz, 2H), 4.19 (q, J=7.2 Hz, 2H), 1.27 (t, J=7.2 Hz, 2H)

Example 27

4-(Biphenyl-2-ylmethyl)-2-(4-chlorobenzylamino)-7-oxo-4,7-dihydrothiazolo[5,4-b]pyridine-6-carboxylic acid (I₃ₐ)

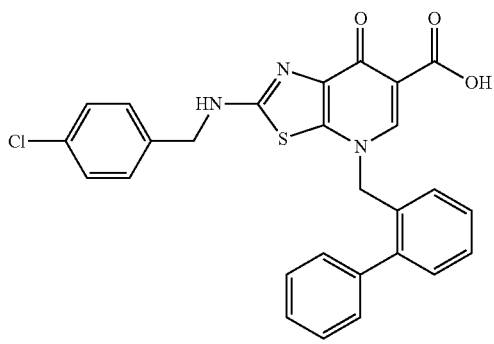 [SMILES: O=C(O)c1cn(Cc2ccccc2-c2ccccc2)c2sc(NCc3ccc(Cl)cc3)nc2c1=O]

I-7 (I-7') was treated with 4-chlorobenzylamine according to the representative method to obtain compound I₃ₐ as a pale white solid.

Yield: 3%

MS (ESI): 502 (M+H)⁺

¹HNMR (d₆-DMSO, 400 MHz):

δ 8.63 (s, 1H), 8.44 (s, 1H), 7.48-7.23 (m, 13H), 5.58 (s, 2H), 4.48 (d, J=5.2 Hz, 2H)

Example 28

Ethyl 4-(biphenyl-2-ylmethyl)-2-(4-chlorobenzylamino)-7-oxo-4,7-dihydrothiazolo[5,4-b]pyridine-6-carboxylate (I₃ₐ-h)

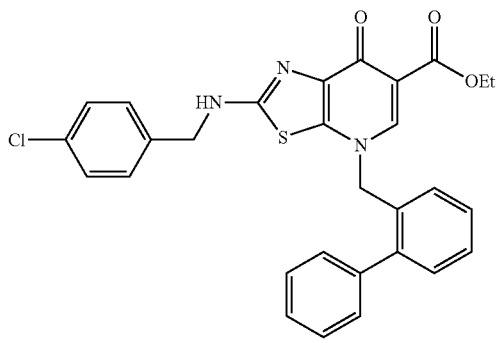 [SMILES: CCOC(=O)c1cn(Cc2ccccc2-c2ccccc2)c2sc(NCc3ccc(Cl)cc3)nc2c1=O]

I-7 (I-7') was treated with 4-chlorobenzylamine according to the representative method to obtain compound I₃ₐ-h as a yellow solid.

Yield: 3%

MS (ESI): 531 (M+H)⁺

¹HNMR (d₆-DMSO, 400 MHz), 68.31 (s, 1H), 8.06 (s, 1H), 7.48-7.16 (m, 13H), 5.35 (s, 2H), 4.43 (d, J=5.2 Hz, 2H), 4.16 (q, J=6.8 Hz, 2H), 1.26 (t, J=6.8 Hz, 3H)

Example 29

4-(Biphenyl-2-ylmethyl)-2-(4-methoxybenzylamino)-7-oxo-4,7-dihydrothiazolo[5,4-]pyridine-6-carboxylic acid (I₄ₐ)

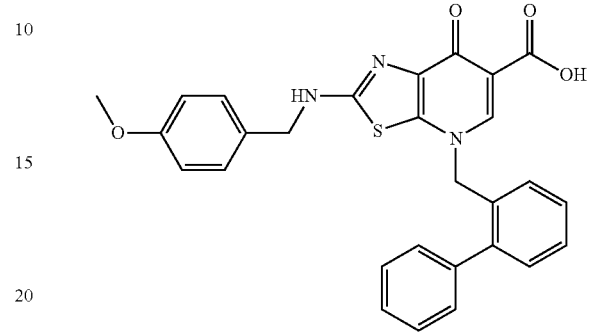

I-7 (I-7') was treated with 4-methoxybenzylamine according to the representative method to obtain compound I₄ₐ as a pale white solid.

Yield: 11%

MS (ESI): 498 (M+H)⁺, 405

¹HNMR (d₆-DMSO, 400 MHz):

δ 16.38 (s, 1H), 8.44 (s, 1H), 7.42-7.23 (m, 11H), 6.89 (d, J=8.0 Hz, 2H), 5.57 (s, 2H), 4.40 (d, J=5.6 Hz, 2H), 3.73 (s, 3H)

Example 30

Ethyl 4-(biphenyl-2-ylmethyl)-2-(4-methoxybenzylamino)-7-oxo-4,7-dihydrothiazolo[5,4-b]pyridine-6-carboxylate (I₄ₐ-h)

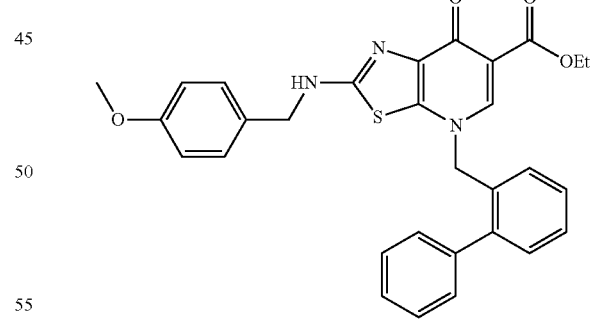

I-7 (I-7') was treated with 4-methoxybenzylamine according to the representative method to obtain compound I₄ₐ-h as a pale white solid.

Yield: 5%

MS (ESI): 526 (M+H)⁺, 405

¹HNMR (d₆-DMSO, 400 MHz):

δ 8.26 (s, 1H), 8.09 (s, 1H), 7.47-7.18 (m, 11H), 6.87 (d, J=8.4 Hz, 2H), 5.37 (s, 2H), 4.35 (d, J=4.8 Hz, 2H), 4.17 (q, J=6.8 Hz, 2H), 1.27 (t, J=6.8 Hz, 3H)

Example 31

4-Benzhydryl-2-(4-methoxybenzylamino)-7-oxo-4,7-dihydrothiazolo[5,4-b]pyridine-6-carboxylic acid ($I_{4D}$)

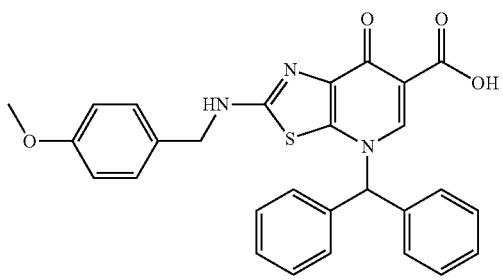 [SMILES: COc1ccc(CNc2nc3c(=O)c(C(=O)O)cn(C(c4ccccc4)c4ccccc4)c3s2)cc1]

The analogue of I-7 (I-7') with diphenylmethyl substitution was treated with 4-methoxybenzylamine according to the representative method to obtain compound $I_{4D}$ as a pale white solid.

Yield: 5%

MS (ESI): 498 (M+H)$^+$ $^1$HNMR (d$_6$-DMSO, 400 MHz):

δ 8.63 (s, 1H), 8.03 (s, 1H), 7.47-7.49 (m, 6H), 7.25-7.29 (m, 6H), 7.11 (s, 1H), 6.88 (d, J=8.0 Hz, 2H), 4.45 (d, J=5.2 Hz, 2H), 3.73 (s, 3H)

Example 32

4-(Biphenyl-2-ylmethyl)-2-(2,6-dichlorobenzylamino)-7-oxo-4,7-dihydrothiazolo[5,4-b]pyridine-6-carboxylic acid ($I_{5A}$)

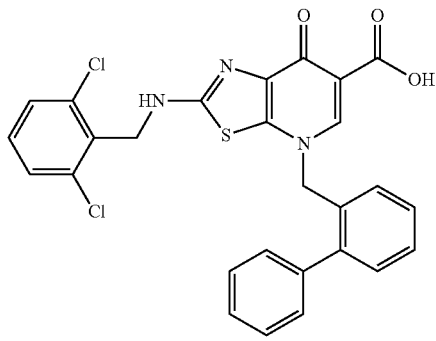 [SMILES: O=C(O)c1cn(Cc2ccccc2-c2ccccc2)c2sc(NCc3c(Cl)cccc3Cl)nc2c1=O]

I-7 (I-7') was treated with 2,5-dichlorobenzylamine according to the representative method to obtain compound $I_{5A}$ as a pink solid.

Yield: 2%

MS (ESI): 536 (M+H)$^+$, 405

$^1$HNMR (d$_6$-DMSO, 400 MHz):

δ 8.48 (s, 1H), 8.34 (s, 1H), 7.21-7.53 (m, 12H), 5.58 (s, 2H), 4.70 (d, J=4.0 Hz, 2H)

Example 33

Ethyl 4-(biphenyl-2-ylmethyl)-2-(2,6-dichlorobenzylamino)-7-oxo-4,7-dihydrothiazolo[5,4-b]pyridine-6-carboxylate ($I_{5A}$-h)

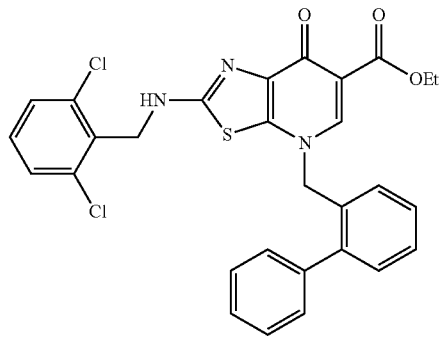 [SMILES: CCOC(=O)c1cn(Cc2ccccc2-c2ccccc2)c2sc(NCc3c(Cl)cccc3Cl)nc2c1=O]

I-7 (I-7') was treated with 2,5-dichlorobenzylamine according to the representative method to obtain compound $I_{5A}$-h as a yellow solid.

Yield: 2%

MS (ESI): 564 (M+H)$^+$ $^1$HNMR d$_6$-DMSO, 400 MHz):

δ8.15 (s, 1H), 8.08 (s, 1H), 7.21-7.53 (m, 12H), 5.40 (s, 2H), 4.66 (s, 2H), 4.20 (q, J=6.8 Hz, 2H), 1.29 (t, J=6.8 Hz, 3H)

Example 34

4-(Biphenyl-2-ylmethyl)-2-(4-carbamoylbenzylamino)-7-oxo-4,7-dihydrothiazolo[5,4-b]pyridine-6-carboxamide ($I_{6A}$-h')

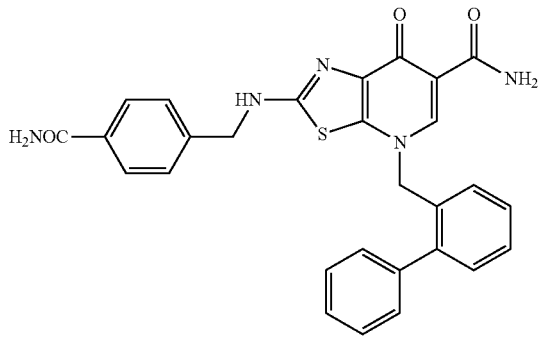 [SMILES: NC(=O)c1ccc(CNc2nc3c(=O)c(C(N)=O)cn(Cc4ccccc4-c4ccccc4)c3s2)cc1]

I-7 (I-7') was treated with ethyl 4-(aminomethyl)benzoate according to the representative method and then ammonia to obtain compound $I_{6A}$-h' as a pale white solid.

Yield: 1%

MS (ESI): 510 (M+H)$^+$ $^1$HNMR (d$_6$-DMSO, 400 MHz):

δ 12.99 (s, 1H), 9.59 (s, 1H), 8.39-8.44 (m, 2H), 7.83-7.88 (m, 2H), 7.48-7.56 (m, 12H), 7.12 (d, J=6.8 Hz, 1H), 5.42 (s, 2H), 4.54 (s, 2H)

Example 35

4-(Biphenyl-2-ylmethyl)-7-oxo-2-(1-phenylethyl-amino)-4,7-dihydrothiazolo[5,4-]pyridine-6-carboxylic acid (I$_{7A}$)

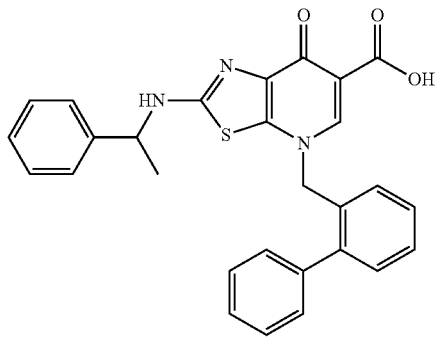 [SMILES: CC(Nc1nc2c(=O)c(C(=O)O)cn(Cc3ccccc3-c3ccccc3)c2s1)c1ccccc1]

I-7 (I-7') was treated with 1-phenylethanamine according to the representative method to obtain compound I$_{7A}$ as a pale white solid.

Yield: 3%

MS (ESI): 482 (M+H)$^+$ $^1$HNMR (d$_6$-DMSO, 400 MHz):

δ 8.68 (d, J=7.2 Hz, 1H), 8.43 (s, 1H), 7.23-7.50 (m, 14H), 5.56 (s, 2H), 4.89-4.92 (m, 1H), 1.41 (d, J=6.8 Hz, 3H)

Example 36

Ethyl 4-(biphenyl-2-ylmethyl)-7-oxo-2-(1-phenyl-ethylamino)-4,7-dihydrothiazolo[5,4-b]pyridine-6-carboxylate (I$_{7A}$-h)

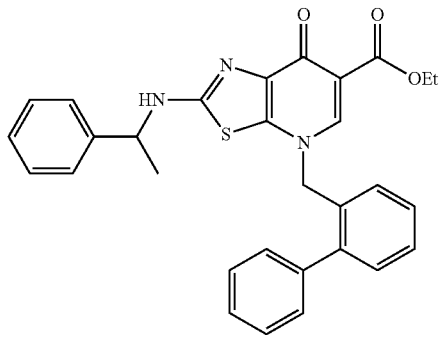 [SMILES: CCOC(=O)c1cn(Cc2ccccc2-c2ccccc2)c2sc(NC(C)c3ccccc3)nc2c1=O]

I-7 (I-7') was treated with 1-phenylethanamine according to the representative method to obtain compound I$_{7A}$-h as a pink solid.

Yield: 1%

MS (ESI): 510 (M+H)$^+$ $^1$HNMR d$_6$-DMSO, 400 MHz):

δ 8.38 (d, J=6.8 Hz, 1H), 8.07 (s, 1H), 7.16-7.46 (m, 14H), 5.38 (s, 2H), 4.83-4.84 (m, 1H), 4.12-4.17 (m, 2H), 1.39 (d, J=6.0 Hz, 3H), 1.26 (t, J=7.2 Hz, 3H)

Example 37

4-(Biphenyl-2-ylmethyl)-2-(4-chloro-2-fluorophe-nylsulfonamido)-7-oxo-4,7-dihydrothiazolo[5,4-b]pyridine-6-carboxylic acid (I$_{9A}$)

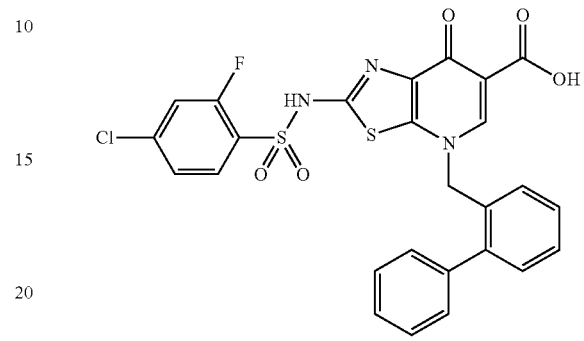

I-7 (I-7') was treated with 2-fluoro-4-chlorophenylsulfo-namide according to the representative method to obtain compound I$_{9A}$ as a pale white solid.

Yield: 2%

MS (ESI): 571 (M+H)$^+$ $^1$HNMR (d$_6$-DMSO, 400 MHz):

δ 8.57 (s, 1H), 7.69-7.77 (m, 2H), 7.25-7.55 (m, 10H), 5.65 (s, 2H)

Example 38

Ethyl 4-(biphenyl-2-ylmethyl)-2-(4-chloro-2-fluoro-phenylsulfonamido)-7-oxo-4,7-dihydrothiazolo[5,4-b]pyridine-6-carboxylate (I$_{9A}$-h)

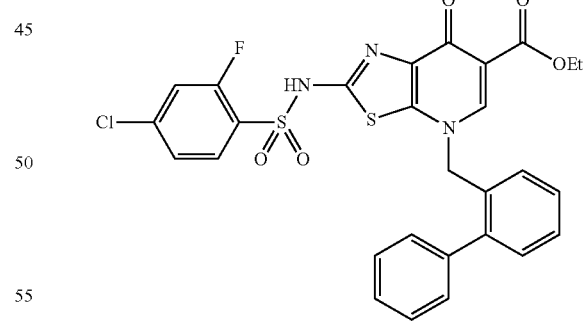

I-7 (I-7') was treated with 2-fluoro-4-chlorophenylsulfo-namide according to the representative method to obtain compound I$_{9A}$-h as a pale white solid.

Yield: 7%

MS (ESI): 599 (M+H)$^+$ $^1$HNMR (d$_6$-DMSO, 400 MHz):

δ 8.21 (s, 1H), 7.68-7.77 (m, 2H), 7.26-7.54 (m, 10H), 5.48 (s, 2H), 4.20 (q, J=7.2 Hz, 2H), 1.27 (t, J=7.2 Hz, 3H)

Example 39

4-Benzhydryl-2-(4-chloro-2-fluorophenylsulfonamido)-7-oxo-4,7-dihydrothiazolo[5,4-b]pyridine-6-carboxylic acid (6)

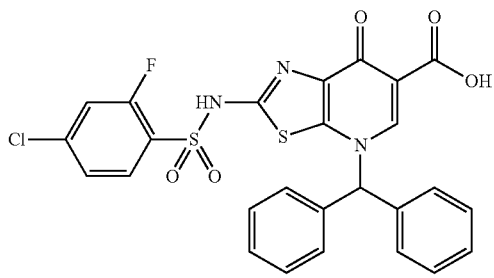 [SMILES: O=C(O)c1cn(C(c2ccccc2)c2ccccc2)c2sc(NS(=O)(=O)c3ccc(Cl)cc3F)nc2c1=O]

The analogue of I-7 (I-7') with diphenylmethyl substitution was treated with 2-fluoro-4-chlorophenylsulfonamide according to the representative method to obtain compound $I_{9D}$ as a pale white solid.

Yield: 1%

MS (ESI): 570 (M+H)+

1HNMR (d6-DMSO, 400 MHz):

δ 8.14 (s, 1H), 7.67-7.74 (m, 2H), 7.40-7.50 (m, 7H), 7.27-7.30 (m, 5H)

Example 40

Ethyl 4-benzhydryl-2-(4-chloro-2-fluorophenylsulfonamido)-7-oxo-4,7-dihydrothiazolo[5,4-b]pyridine-6-carboxylate ($I_{9D}$-h)

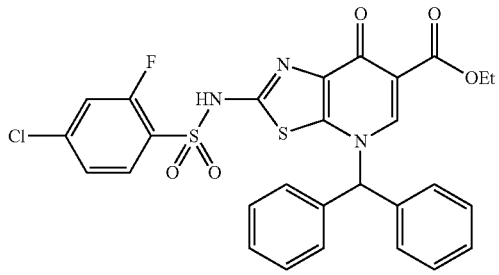 [SMILES: CCOC(=O)c1cn(C(c2ccccc2)c2ccccc2)c2sc(NS(=O)(=O)c3ccc(Cl)cc3F)nc2c1=O]

The analogue of I-7 (I-7') with diphenylmethyl substitution was treated with 2-fluoro-4-chlorophenylsulfonamide according to the representative method to obtain compound 6-h as a yellow solid.

Yield: 5%

MS (ESI): 598 (M+H)+

1HNMR (d6-DMSO, 400 MHz):

δ 8.01 (s, 1H), 7.68-7.73 (m, 2H), 7.40-7.49 (m, 7H), 7.29 (s, 4H), 7.12 (s, 1H), 4.10 (q, J=7.2 Hz, 2H), 1.14 (t, J=6.8 Hz, 3H)

Example 41

4-(Biphenyl-2-ylmethyl)-2-(4-cyanophenylsulfonamido)-7-oxo-4,7-dihydrothiazolo[5,4-b]pyridine-6-carboxylic acid ($I_{10A}$)

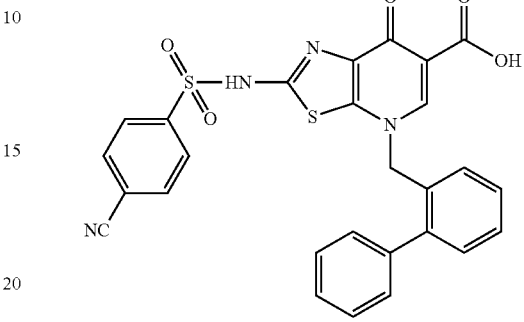

I-7 (I-7') was treated with 4-cyanophenylsulfonamide according to the representative method to obtain compound $I_{10A}$ as a pale white solid.

Yield: 9%

MS (ESI): 543 (M+H)+

1H NMR (d6-DMSO, 400 MHz):

δ 8.54 (s, 1H), 8.02 (d, J=8.0 Hz, 2H), 7.83 (d, J=8.0 Hz, 2H), 7.57 (t, J=7.2 Hz, 1H), 7.46-7.49 (t, J=7.6 Hz, 1H), 7.32-7.41 (m, 5H), 7.24 (d, J=7.2 Hz, 2H), 5.64 (s, 2H),

Example 42

Ethyl 4-(biphenyl-2-ylmethyl)-2-(4-cyanophenylsulfonamido)-7-oxo-4,7-dihydrothiazolo[5,4-b]pyridine-6-carboxylate ($I_{10A}$-h)

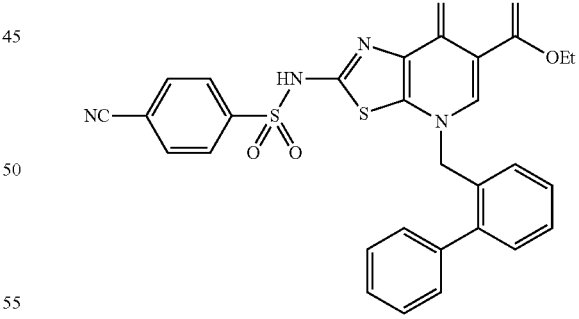

I-7 (I-7') was treated with 4-cyanophenylsulfonamide according to the representative method to obtain compound $I_{10A}$-h as a pale white solid.

Yield: 2%

MS (ESI): 571 (M+H)+

1HNMR (d6-DMSO, 400 MHz):

δ 8.20 (s, 1H), 8.03 (d, J=7.6 Hz, 2H), 7.82 (d, J=8.0 Hz, 2H), 7.26-7.55 (m, 9H), 5.49 (s, 2H), 4.18 (q, J=7.2 Hz, 2H), 1.27 (t, J=7.2 Hz, 3H)

Example 43

Ethyl 4-(biphenyl-2-ylmethyl)-2-(4-(ethoxycarbonyl)phenylsulfonamido)-7-oxo-4,7-dihydrothiazolo[5,4-b]pyridine-6-carboxylate ($I_{10A}$-h')

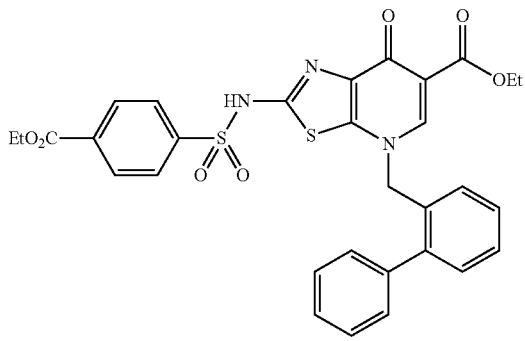 [SMILES: CCOC(=O)c1ccc(S(=O)(=O)Nc2nc3c(=O)c(C(=O)OCC)cn(Cc4ccccc4-c4ccccc4)c3s2)cc1]

I-7 (I-7') was treated with ethyl 4-sulfamoylbenzoate according to the representative method to obtain compound $I_{10A}$-h' as a pale white solid.

Yield: 2%

MS (ESI): 618 (M+H)$^+$ $^1$HNMR (d$_6$-DMSO, 400 MHz):

δ 8.19 (s, 1H), 8.06 (d, J=8.0 Hz, 2H), 7.82 (d, J=7.6 Hz, 2H), 7.53-7.27 (m, 9H), 5.47 (s, 2H), 4.34 (q, J=6.8 Hz, 2H), 4.18 (q, J=6.8 Hz, 2H), 4.20 (q, J=6.8 Hz, 2H), 1.33 (t, J=7.2 Hz, 3H), 1.26 (t, J=7.2 Hz, 3H)

Example 44

4-(Biphenyl-2-ylmethyl)-2-(4-methoxyphenylsulfonamido)-7-oxo-4,7-dihydrothiazolo[5,4-b]pyridine-6-carboxylic acid ($I_{11A}$)

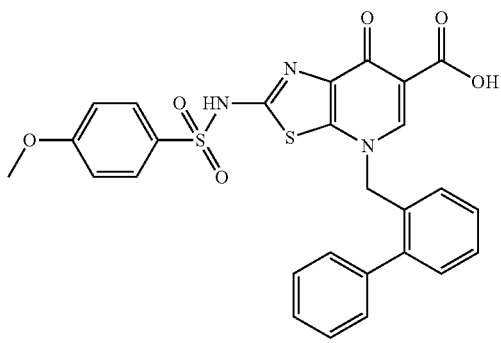 [SMILES: COc1ccc(S(=O)(=O)Nc2nc3c(=O)c(C(=O)O)cn(Cc4ccccc4-c4ccccc4)c3s2)cc1]

I-7 (I-7') was treated with 4-methoxyphenylsulfonamide according to the representative method to obtain compound $I_{11A}$ as a pale white solid.

Yield: 7%

MS (ESI): 548 (M+H)$^+$ $^1$H NMR (d$_6$-DMSO, 400 MHz):

δ 8.56 (s, 1H), 7.59-7.65 (m, 3H), 7.55 (t, J=7.2 Hz, 1H), 7.44 (d, J=7.2 Hz, 1H), 7.29-7.49 (m, 4H), 7.20 (d, J=6.8 Hz, 2H), 7.07 (d, J=7.6 Hz, 2H), 5.63 (s, 2H), 3.83 (s, 3H)

Example 45

Ethyl 4-(biphenyl-2-ylmethyl)-2-(4-methoxyphenylsulfonamido)-7-oxo-4,7-dihydrothiazolo[5,4-b]pyridine-6-carboxylate ($I_{11A}$-h)

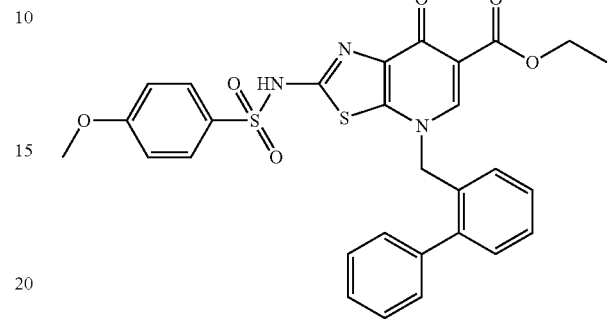

I-7 (I-7') was treated with 4-methoxyphenylsulfonamide according to the representative method to obtain compound $I_{11A}$-h as a pale white solid.

Yield: 3%

MS (ESI): 576(M+H)$^+$, 169

$^1$H NMR (d$_6$-DMSO, 400 MHz):

δ 8.19 (s, 1H), 7.60 (d, J=8.4 Hz, 2H), 7.55 (t, J=7.2 Hz, 1H), 7.48 (t, J=7.2 Hz, 1H), 7.33-7.43 (m, 5H), 7.27 (d, J=6.8 Hz, 2H), 7.04 (d, J=8.8 Hz, 2H), 5.48 (s, 2H), 4.18 (q, J=7.2 Hz, 2H), δ 3.82 (s, 3H), 1.26 (t, J=7.2 Hz, 3H)

Example 46

4-Benzhydryl-2-(4-methoxyphenylsulfonamido)-7-oxo-4,7-dihydrothiazolo[5,4-b]pyridine-6-carboxylic acid ($I_{11D}$)

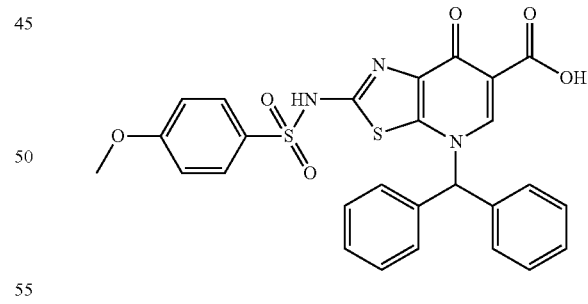

The analogue of I-7 (I-7') with diphenylmethyl substitution was treated with 4-methoxyphenylsulfonamide according to the representative method to obtain compound $I_{11D}$ as a pale white solid.

Yield: 1%

MS (ESI): 548(M+H)$^+$, 169

$^1$H NMR (d$_6$-DMSO, 400 MHz):

δ 8.12 (s, 1H), 7.60 (d, J=8.4 Hz, 2H), 7.52 (br, s, 6H), 7.32 (br, s, 4H), 7.26 (s, 1H), 7.02 (d, J=8.4 Hz, 2H), 3.83 (s, 3H)

Example 47

Ethyl 4-benzhydryl-2-(4-methoxyphenylsulfonamido)-7-oxo-4,7-dihydro thiazolo[5,4-b]pyridine-6-carboxylate (I$_{11D}$-h)

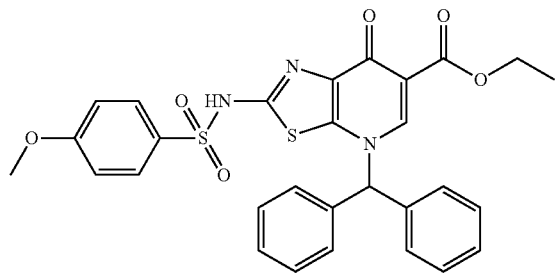 [SMILES: CCOC(=O)c1cn(C(c2ccccc2)c2ccccc2)c2sc(NS(=O)(=O)c3ccc(OC)cc3)nc2c1=O]

The analogue of I-7 (I-7') with diphenylmethyl substitution was treated with 4-methoxyphenylsulfonamide according to the representative method to obtain compound I$_{11D}$-h as a pale white solid.

Yield: 2%

MS (ESI): 576(M+H)$^+$, 169

$^1$H NMR (d$_6$-DMSO, 400 MHz):

δ 7.98 (s, 1H), 7.59 (d, J=8.8 Hz, 2H), 7.51 (br, s, 6H), 7.30 (br, s, 4H), 7.11 (s, 1H), 7.02 (d, J=8.4 Hz, 2H), 4.10 (q, J=7.2 Hz, 2H), 3.83 (s, 3H), 1.13 (t, J=7.2 Hz, 3H)

Example 48

4-(Biphenyl-2-ylmethyl)-2-((4-chlorophenyl)methylsulfonamido)-7-oxo-4,7-dihydrothiazolo[5,4-b]pyridine-6-carboxylic acid (I$_{12A}$)

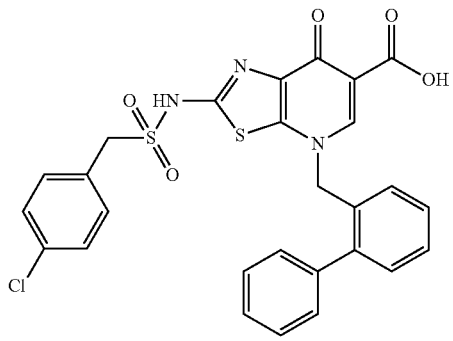 [SMILES: O=C(O)c1cn(Cc2ccccc2-c2ccccc2)c2sc(NS(=O)(=O)Cc3ccc(Cl)cc3)nc2c1=O]

I-7 (I-7') was treated with 4-chlorophenylsulfonamide according to the representative method to obtain compound I$_{12A}$ as a pale white solid.

Yield: 1%

MS (ESI): 566 (M+H)$^+$, 157

$^1$H NMR (d$_6$-DMSO, 400 MHz):

δ 8.51 (s, 1H), 7.19-7.54 (m, 13H), 5.57 (s, 2H), 4.39 (s, 2H)

Example 49

Ethyl 4-(biphenyl-2-ylmethyl)-2-((4-chlorophenyl)methylsulfonamido)-7-oxo-4,7-dihydrothiazolo[5,4-b]pyridine-6-carboxylate(I$_{12A}$-h)

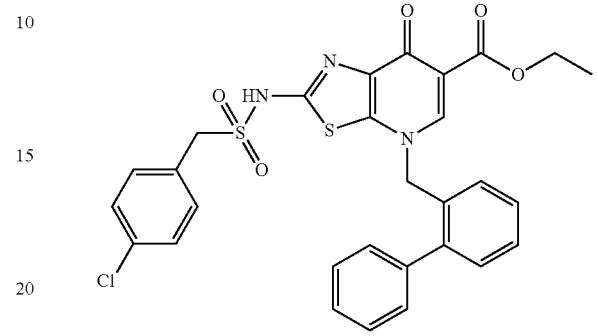

I-7 (I-7') was treated with 4-chlorophenylsulfonamide according to the representative method to obtain compound I$_{12A}$-h as a pale white solid.

Yield: 2%

MS (ESI): 594 (M+H)$^+$

1H NMR (d$_6$-DMSO, 400 MHz):

δ 8.24 (s, 1H), 8.17 (s, 1H), 7.25-7.50 (m, 13H), 5.36 (s, 2H), 4.30 (s, 2H), 4.21 (q, J=7.2 Hz, 2H), 1.30 (t, J=7.2 Hz, 3H)

Example 50

Ethyl 4-(biphenyl-2-ylmethyl)-2-((2,4-dichlorophenyl)methylsulfonamido)-7-oxo-4,7-dihydrothiazolo[5,4-b]pyridine-6-carboxylate (I$_{13A}$-h)

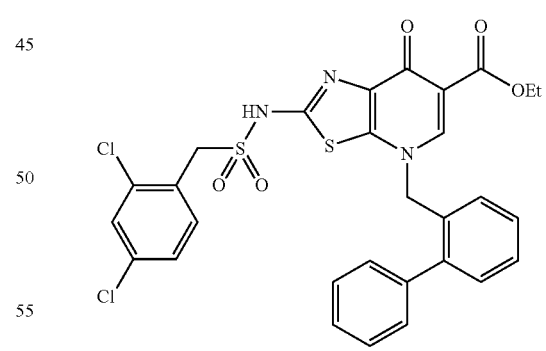

I-7 (I-7') was treated with 2,4-dichlorophenylsulfonamide according to the representative method to obtain compound I$_{13A}$-h as a pale white solid.

Yield: 1%

MS (ESI): 628 (M+H)$^+$, 169

$^1$H NMR (d$_6$-DMSO, 400 MHz):

δ 8.16 (s, 1H), 7.23-7.57 (m, 12H), 5.41 (s, 2H), 4.45 (s, 2H), 4.19 (q, J=6.8 Hz, 2H), 1.28 (t, J=7.2 Hz, 3H)

Example 51

Ethyl 7-(benzhydryloxy)-2-(methylthio)thiazolo[5,4-b]pyridine-6-carboxylate (I$_d$-f')

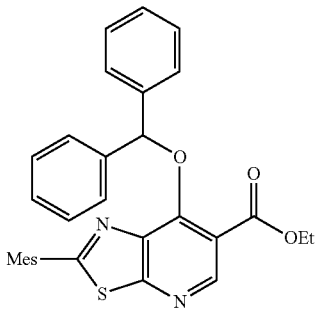

I-5 was treated with (bromomethylene)dibenzene according to the general procedure to obtain compound I$_d$-f' as a pale white solid.

Yield: 1%

MS (ESI): 437 (M+H)$^+$, 105

$^1$H NMR (d$_6$-DMSO, 400 MHz):

δ 8.66 (s, 1H), 7.98 (s, 1H), 7.57-7.59 (m, 4H), 7.32-7.36 (m, 4H), 7.23-7.26 (m, 2H), 4.42 (q, J=6.8 Hz, 2H), 2.90 (s, 3H), 1.35-1.38 (t, J=7.2 Hz, 3H)

Example 52

Ethyl 4-(biphenyl-2-ylmethyl)-7-oxo-4,7-dihydrothiazolo[5,4-b]pyridine-6-carboxylate (I-f-a)

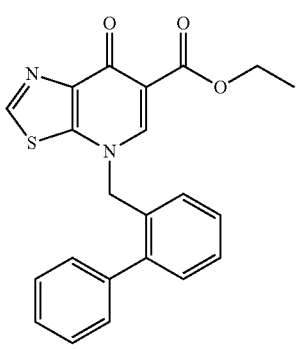 [SMILES: CCOC(=O)c1cn(Cc2ccccc2-c2ccccc2)c2scnc2c1=O]

I-6 was treated with zinc in acetic acid to obtain compound I-f-a as a yellow solid.

Yield: 5%

MS (ESI): 391(M+H)$^+$, 130, 105

$^1$H NMR (CDCl$_3$, 400 MHz):

δ 8.57 (s, 1H), 8.00 (s, 1H), 7.32-7.50 (m, 7H), 7.12 (d, J=6.4 Hz, 2H), 5.28 (s, 2H), 4.35 (q, J=6.8 Hz, 2H), 1.38 (t, J=7.2 Hz, 3H)

Example 53

7-Hydroxy-2-(methylthio)thiazolo[5,4-b]pyridine-6-carboxylic acid (I-e-1)

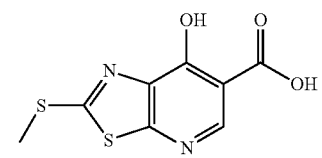

I-5 was treated with LiOH in ethanol and water to obtain compound I-e-1 as a pale white solid.

Yield: 5%

MS (ESI): 243 (M+H)$^+$, 157

$^1$H NMR (d$_6$-DMSO, 300 MHz):

δ 8.77 (s, 1H), 2.79 (s, 3H)

Example 54

7-(Biphenyl-2-ylmethoxy)-2-(methylthio)thiazolo[5,4-b]pyridine-6-carboxylic acid (I-f'-1)

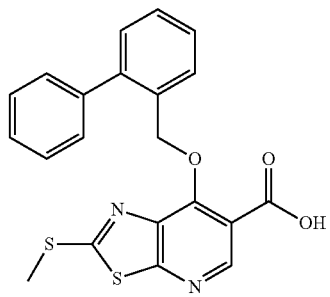 [SMILES: CSc1nc2c(OCc3ccccc3-c3ccccc3)c(C(=O)O)cnc2s1]

I-5 was treated with 2-(bromomethyl)biphenyl and then LiOH to obtain compound I-f'-1 as a pale white solid.

Yield: 5%

MS (ESI): 409 (M+H)$^+$, 157

$^1$H NMR (d$_6$-DMSO, 300 MHz):

δ 13.24 (br, s, 1H), 8.62 (s, 1H), 7.87-7.90 (m, 1H), 7.28-7.46 (m, 8H), 5.92 (s, 2H), 2.54 (s, 3H)

Example 55

4-(Biphenyl-2-ylmethyl)-2-(methylthio)-7-oxo-4,7-dihydrothiazolo[5,4-b]pyridine-6-carboxylic acid (I-f-2)

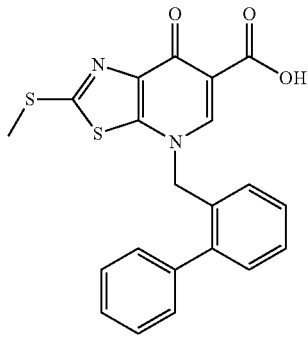 [SMILES: CSc1nc2c(=O)c(C(=O)O)cn(Cc3ccccc3-c3ccccc3)c2s1]

I-5 was treated with 2-(bromomethyl)biphenyl and then LiOH to obtain compound 14-2 as a pale white solid.
Yield: 5%
MS (ESI): 409(M+H)$^+$, 157
$^1$H NMR (d$_6$-DMSO, 300 MHz):
δ 15.46 (s, 1H), 8.57 (s, 1H), 7.21-7.50 (m, 9H), 5.67 (s, 2H), 2.69 (s, 3H)

Example 56

4-(Biphenyl-2-ylmethyl)-2-hydroxy-7-oxo-4,7-dihydrothiazolo[5,4-b]pyridine-6-carboxylic acid(I-h')

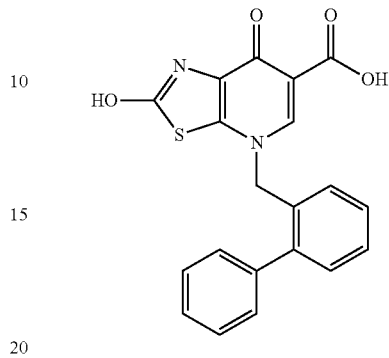

I-6 was treated with sodium hydroxide to obtain compound I-h' as a pale white solid.
Yield: 2%
MS (ESI): 379(M+H)$^+$
$^1$H NMR (d$_6$-DMSO, 400 MHz):
δ 15.23 (s, 1H), 12.71 (s, 1H), 8.53 (s, 1H), 7.26-7.51 (m, 9H), 5.55 (s, 2H)

All of the compounds listed in the following table have been prepared as set out above or by analogous methods.
Activity Data for Compounds Having the General Formula (A)

| Structure | FRET | CPE |
|---|---|---|
| 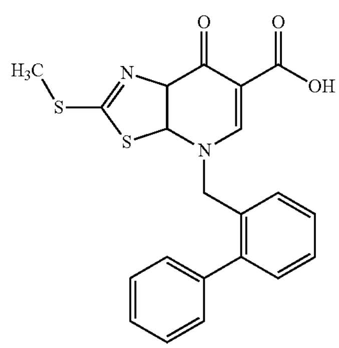 [SMILES: CSC1=NC2C(=O)C(C(=O)O)=CN(Cc3ccccc3-c3ccccc3)C2S1] | IC$_{50}$ = 12 μM | inactive; Toxic at 50 μM |
| 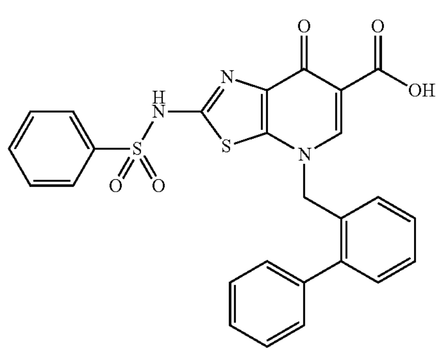 [SMILES: O=C(O)c1cn(Cc2ccccc2-c2ccccc2)c2sc(NS(=O)(=O)c3ccccc3)nc2c1=O] | IC$_{50}$ = 6.5 μM | IC$_{50}$ = 17 μM |

-continued

| Structure | FRET | CPE |
|---|---|---|
| (2-benzylamino-7-oxo-4-([1,1'-biphenyl]-2-ylmethyl)-4,7-dihydrothiazolo[5,4-b]pyridine-6-carboxylic acid) | IC$_{50}$ = 3.2 μM | IC$_{50}$ = 19 μM |
| (2-cyclopentylamino-7-oxo-4-([1,1'-biphenyl]-2-ylmethyl)-4,7-dihydrothiazolo[5,4-b]pyridine-6-carboxylic acid) | inactive | 70% reduction @ 50 μM |
| (2-benzylamino-7-oxo-4-([1,1'-biphenyl]-2-ylmethyl)-4,7-dihydrothiazolo[4,5-b]pyridine-6-carboxylic acid) | inactive | 68% reduction @ 50 μM |
| (2-methylamino-7-oxo-4-([1,1'-biphenyl]-2-ylmethyl)-4,7-dihydrothiazolo[5,4-b]pyridine-6-carboxylic acid) | IC$_{50}$ = 2.8 μM | inactive |

| Structure | FRET | CPE |
|---|---|---|
| 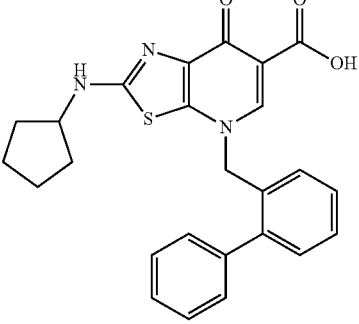 | IC$_{50}$ = 5.5 μM | inactive; toxic at 50 μM |
| 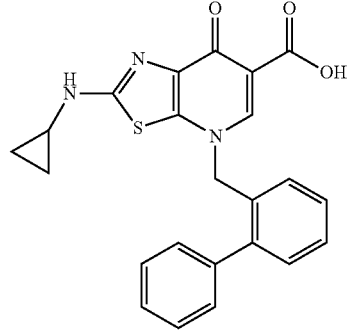 [SMILES: O=C(O)c1cn(Cc2ccccc2-c2ccccc2)c2sc(NC3CC3)nc2c1=O] | IC$_{50}$ = 2.5 μM | IC$_{50}$ = 31 μM |
| 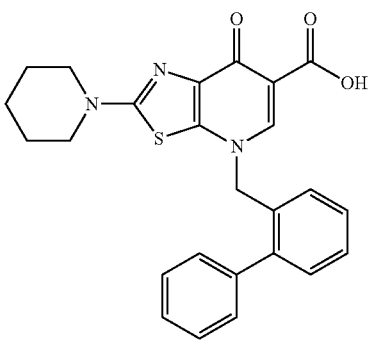 [SMILES: O=C(O)c1cn(Cc2ccccc2-c2ccccc2)c2sc(N3CCCCC3)nc2c1=O] | inactive | 83% reduction @ 50 μM |
| 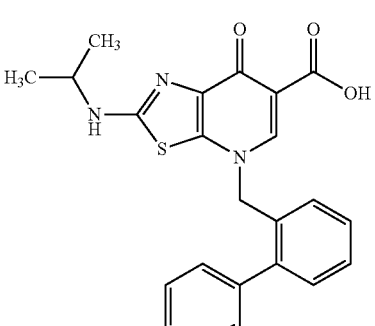 | IC$_{50}$ = 14 μM | inactive |

-continued

| Structure | FRET | CPE |
|---|---|---|
| (structure) | IC$_{50}$ = 9 μM | inactive |
| (structure) | IC$_{50}$ = 0.78 μM | inactive |
| (structure) | inactive | 41% @ 50 μM |
| (structure) | IC$_{50}$ = 7.3 μM | n.d. |

| Structure | FRET | CPE |
|---|---|---|
| (3-fluorophenylsulfonylamino-thiazolopyridinone carboxylic acid with 2-biphenylmethyl) | IC$_{50}$ = 6.7 μM | IC$_{50}$ = 19 μM |
| (methylsulfonylamino-thiazolopyridinone carboxylic acid with 2-biphenylmethyl) | IC$_{50}$ = 8.1 μM | inactive |
| (4-chlorobenzylamino-thiazolopyridinone carboxylic acid with 2-biphenylmethyl) | IC$_{50}$ = 2.3 μM | IC$_{50}$ = 9.3 μM |
| (4-methoxybenzylamino-thiazolopyridinone carboxylic acid with 2-biphenylmethyl) | IC$_{50}$ = 2.9 μM | IC$_{50}$ = 11 μM |

-continued

| Structure | FRET | CPE |
|---|---|---|
| (structure: 2-[(3-chlorobenzyl)amino]-4-([1,1'-biphenyl]-2-ylmethyl)-7-oxo-4,7-dihydrothiazolo[5,4-b]pyridine-6-carboxylic acid) | IC$_{50}$ = 5.2 µM | IC$_{50}$ = 12 µM |
| (structure: 2-[(1-phenylethyl)amino] analog with biphenylmethyl) | IC$_{50}$ = 5.8 µM | IC$_{50}$ = 24 µM |
| (structure: 2-[(4-cyanophenylsulfonyl)amino] analog with biphenylmethyl) | IC$_{50}$ = 2.2 µM | IC$_{50}$ = 18 µM |
| (structure: 2-hydroxy analog with biphenylmethyl) | IC$_{50}$ = 0.16 µM | IC$_{50}$ = 33 µM |

| Structure | FRET | CPE |
|---|---|---|
| (4-methoxyphenylsulfonamido thiazolopyridinone carboxylic acid, N-biphenylmethyl) | IC$_{50}$ = 2.7 μM | IC$_{50}$ = 15 μM |
| (4-chloro-2-fluorophenylsulfonamido thiazolopyridinone ethyl ester, N-biphenylmethyl) | inactive | IC$_{50}$ = 39 μM |
| (4-chloro-2-fluorophenylsulfonamido thiazolopyridinone carboxylic acid, N-biphenylmethyl) | IC$_{50}$ = 5.7 μM | IC$_{50}$ = 11 μM |
| (4-chlorophenylsulfonamido thiazolopyridinone ethyl ester, N-biphenylmethyl) | 6.2% @ 1 μM | IC$_{50}$ = 23 μM |

-continued

| Structure | FRET | CPE |
|---|---|---|
| | IC$_{50}$ = 6.3 µM | n.d. |
| | 8.1% @ 1 µM | n.d. |
| | 21.5% @ 10 µM | n.d. |
| | 5.6% @ 1 µM | n.d. |
| | 2% @ 1 µM | IC$_{50}$ = 26 µM |

-continued

| Structure | FRET | CPE |
|---|---|---|
| (4-methoxyphenylsulfonamido thiazolo-pyridinone carboxylic acid, N-benzhydryl) | 7.8% @ 1 µM | IC$_{50}$ = 31 µM |
| (4-methoxyphenylsulfonamido thiazolo-pyridinone carboxylic acid ethyl ester, N-benzhydryl) | 25% @ 1 µM | IC$_{50}$ = 36 µM |
| (3-chlorobenzylamino thiazolo-pyridinone carboxylic acid ethyl ester, N-benzhydryl) | n.d. | IC$_{50}$ = 27 µM |
| (4-chlorobenzylamino thiazolo-pyridinone carboxylic acid ethyl ester, N-benzhydryl) | n.d. | IC$_{50}$ = 45 µM |
| (2-hydroxy thiazolo-pyridinone carboxylic acid, N-benzhydryl) | IC$_{50}$ = 0.78 µM | IC$_{50}$ = 47 µM |

-continued

| Structure | FRET | CPE |
|---|---|---|
| 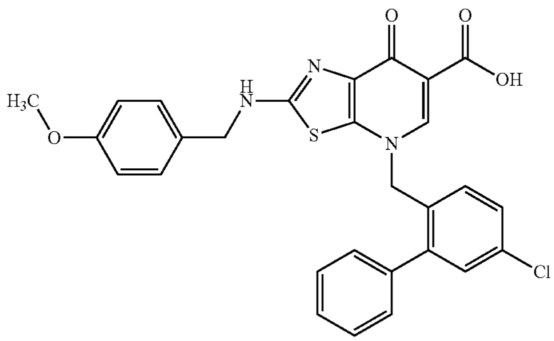 [SMILES: COc1ccc(CNc2nc3c(=O)c(C(=O)O)cn(Cc4ccc(Cl)cc4-c4ccccc4)c3s2)cc1] | $IC_{50}$ = 3.8 μM | $IC_{50}$ = 22 μM |
| 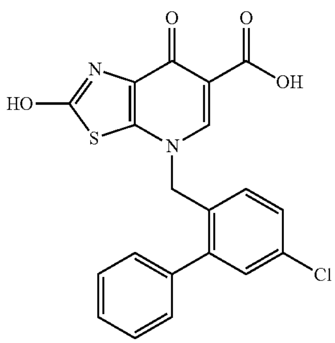 [SMILES: O=C(O)c1cn(Cc2ccc(Cl)cc2-c2ccccc2)c2sc(O)nc2c1=O] | $IC_{50}$ = 0.87 μM | $IC_{50}$ = 18 μM |
| | n.d. | $IC_{50}$ = 32 μM |
| | n.d. | n.d. |
| | n.d. | n.d. |

| Structure | FRET | CPE |
|---|---|---|
| | n.d. | IC$_{50}$ = 14 μM |
| | n.d. | n.d. |
| | n.d. | 63% @ 50 μM |
| | n.d. | 67% @ 50 μM |

-continued

| Structure | FRET | CPE |
|---|---|---|
| (structure) | 64% @ 10 μM | inactive |
| (structure) | IC$_{50}$ = 7 μM | IC$_{50}$ = 20 μM |
| (structure) | IC$_{50}$ = 2.5 μM | IC$_{50}$ = 14 μM |
| (structure) | IC$_{50}$ = 7.2 μM | IC$_{50}$ = 8.9 μM |

-continued
| Structure | FRET | CPE |
|---|---|---|
| 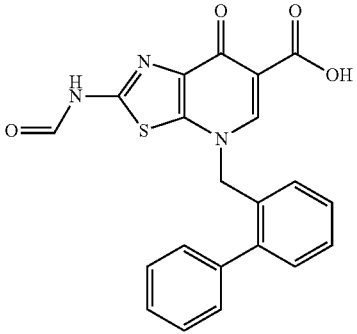 [SMILES: O=CNc1nc2c(=O)c(C(=O)O)cn(Cc3ccccc3-c3ccccc3)c2s1] | IC$_{50}$ = 4.7 µM | inactive |
| 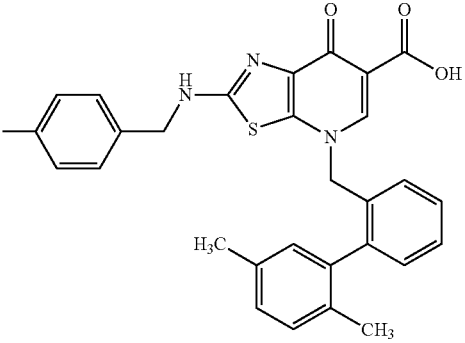 | IC$_{50}$ = 2.1 µM | n.d. |
| 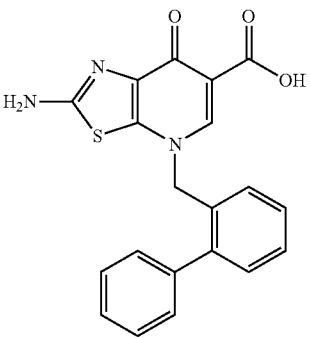 [SMILES: Nc1nc2c(=O)c(C(=O)O)cn(Cc3ccccc3-c3ccccc3)c2s1] | IC$_{50}$ = 0.94 µM | inactive |
| 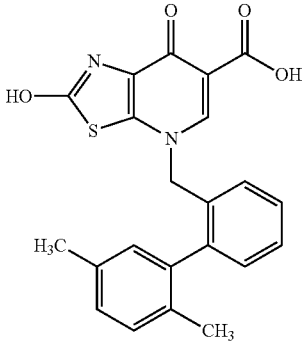 [SMILES: Cc1ccc(C)c(-c2ccccc2Cn2cc(C(=O)O)c(=O)c3nc(O)sc32)c1] | IC$_{50}$ = 0.25 µM | n.d. |

| Structure | FRET | CPE |
|---|---|---|
| 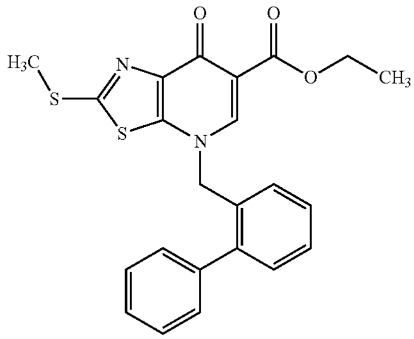 [SMILES: CCOC(=O)c1cn(Cc2ccccc2-c2ccccc2)c2sc(SC)nc2c1=O] | inactive | 35% @ 50 μM |

Compounds Having the General Formula (C)

Key Intermediate I

2-Formyl-Succinic Acid Diethyl Ester

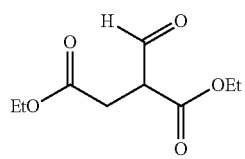

I

Key Intermediate II

2-Cyclopropyl-7-oxo-4,7-dihydro-pyrazolo[1,5-a]pyrimidine-6-carboxylic acid ethyl ester

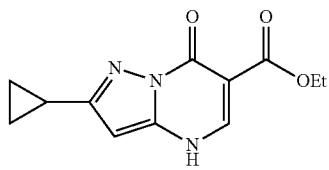

II

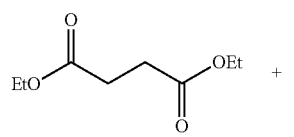 + 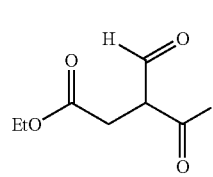 → 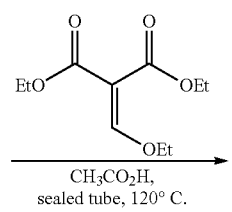

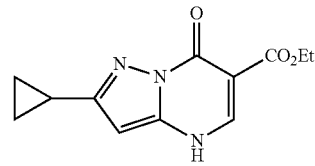

To a suspension of sodium (333 mg, 14 mmol, 1.2 eq) in diethyl ether (7 mL) were added succinic acid diethyl ester (2.1 g, 12 mmol, 1 eq) and formic acid ethyl ester (1.7 mL, 20 mmol, 1.7 eq). The mixture was stirred at 40° C. for 5 h. Water (10 mL) was added and the aqueous layer was washed with diethyl ether (2×10 mL). The aqueous layer was then acidified with a 6N solution of hydrochloric acid and extracted with diethyl ether (3×10 mL). The organic layers were dried over magnesium sulfate, filtered and evaporated in vacuo to afford the expected compound as orange oil (2.6 g, quant. yield).

To a solution of 5-cyclopropyl-2H-pyrazol-3-ylamine (280 mg, 2.3 mmol, 1 eq) in acetic acid (3 mL) was added 2-ethoxymethylene-malonic acid diethyl ester (500 μL, 2.5 mmol, 1.1 eq). The mixture was heated at 120° C. for 2 h in a sealed tube. After cooling, the precipitate was filtered and washed with ethanol to afford the expected compound as white powder (420 mg, 75% yield).

Key Intermediate III

2-Isopropyl-7-oxo-4,7-dihydro-pyrazolo[1,5-a]pyrimidine-6-carboxylic acid ethyl ester

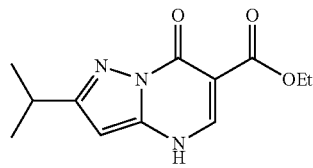

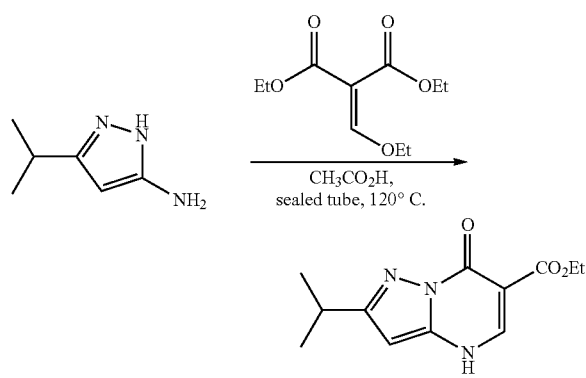

To a solution of 5-isopropyl-2H-pyrazol-3-ylamine (2.5 g, 20 mmol, 1 eq) in acetic acid (20 mL) was added 2-ethoxymethylene-malonic acid diethyl ester (4.4 mL, 22 mmol, 1.1 eq). The mixture was heated at 120° C. for 3 h in a sealed tube. After cooling, the precipitate was filtered and washed with ethanol to afford the expected compound as beige powder (3.2 g, 65% yield).

Key Intermediate IV

2-Cyclopentyl-7-oxo-4,7-dihydro-pyrazolo[1,5-a]pyrimidine-6-carboxylic acid ethyl ester

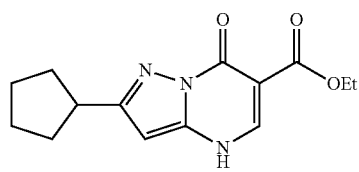

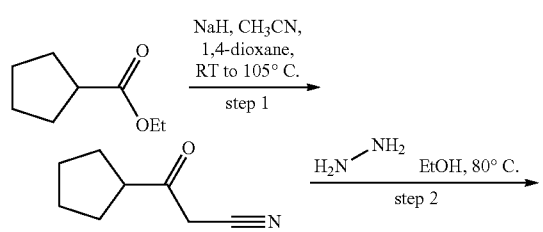

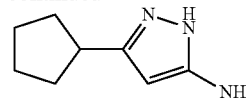

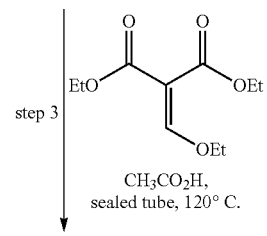

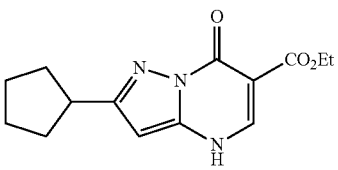

Step 1:

To a suspension of sodium hydride (350 mg, 8.8 mmol, 1.2 eq) in 1,4-dioxane (10 mL) was added acetonitrile (450 µL, 8.8 mmol, 1.2 eq). The mixture was stirred at room temperature for 30 min. Then cyclopentanecarboxylic acid ethyl ester (660 µL, 7.3 mmol, 1 eq) was added. After stirring for 30 min at room temperature, the mixture was heated at 105° C. during 16 h. After cooling, the solvent was evaporated to dryness and water was added (30 mL). The mixture was extracted with dichloromethane (3×30 mL) to get rid of the starting material and the aqueous phase was acidified with a 1N solution of hydrochloric acid and extracted with dichloromethane (3×30 mL). The combined organic phases were dried over magnesium sulfate, filtered and dried in vacuo to afford 3-cyclopentyl-3-oxo-propionitrile as very volatile yellow oil (1.0 g, quant. yield)

Step 2:

To a solution of 3-cyclopentyl-3-oxo-propionitrile (1.0 g, 7.3 mmol, 1 eq) in ethanol (10 mL) was added a 64 wt.-% solution of hydrazine hydrate (1.1 mL, 14.6 mmol, 2 eq). The mixture was heated at 80° C. for 16 h and was evaporated to dryness. The residue was purified by flash chromatography using dichloromethane and methanol (100/0 to 90/10) to afford 5-cyclopentyl-2H-pyrazol-3-ylamine as yellow oil (510 mg, 46% yield).

Step 3:

To a solution of 5-cyclopentyl-2H-pyrazol-3-ylamine (510 mg, 3.4 mmol, 1 eq) in acetic acid (4.8 mL) was added 2-ethoxymethylene-malonic acid diethyl ester (750 µL, 3.7 mmol, 1.1 eq). The mixture was heated at 120° C. for 3 h in a sealed tube. After cooling, the precipitate was filtered and washed with ethanol and diethyl ether and recrystallised from methanol to afford the expected compound as white powder (657 mg, 71% yield).

MS: 276.1

Mp: decomposes at 300° C.

Key Intermediate V

7-Oxo-4,7-dihydro-pyrazolo[1,5-a]pyrimidine-2,6-dicarboxylic acid 6-ethyl ester

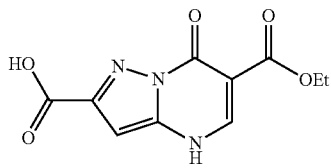

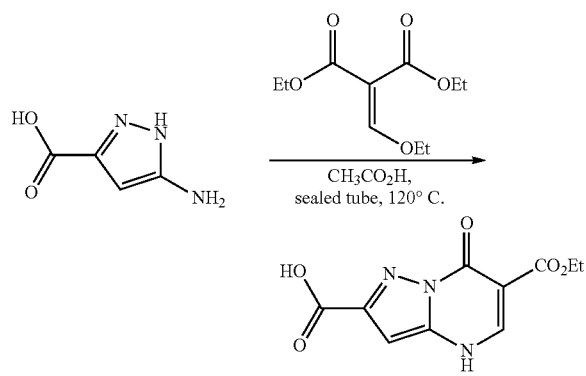

To a solution of 5-amino-1H-pyrazole-3-carboxylic acid (600 mg, 4.7 mmol, 1 eq) in acetic acid (30 mL) was added 2-ethoxymethylene-malonic acid diethyl ester (1.1 g, 5.2 mmol, 1.1 eq). The mixture was heated at 120° C. for 4 h in a sealed tube. After cooling, the precipitate was filtered and washed with ethanol to afford the expected compound as grey powder (353 mg, 30% yield).

General Procedure A

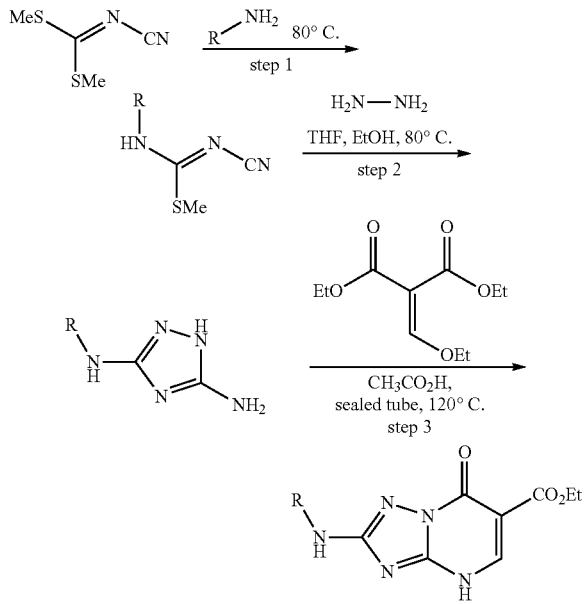

Step 1:

To a solution of the appropriate amine (4.3 mmol, 1 eq) in ethanol (10 mL) was added dimethyl N-cyanodithioiminocarbonate (1.0 g, 6.8 mmol, 1.6 eq). The mixture was stirred at 80° C. for 20 h. After cooling, the precipitate was filtered and rinsed with ethanol to afford the expected compound (from 25% to 70% yield).

Step 2:

To a solution of the compound from step 1 (1.1 mmol, 1 eq) in ethanol (10 mL) was added a 1M solution of hydrazine in tetrahydrofuran (2.3 mL, 2.3 mmol, 2 eq). The mixture was heated at 80° C. for 20 h and was evaporated to dryness. The product was then triturated with diethyl ether, filtered and washed with diethyl ether to afford the expected compound (from 75% to 85% yield).

Step 3:

To a solution of the compound from step 2 (0.86 mmol, 1 eq) in acetic acid (4 mL) was added 2-ethoxymethylene-malonic acid diethyl ester (190 μL, 0.94 mmol, 1.1 eq). The mixture was heated at 120° C. for 20 h in a sealed tube. After cooling, the precipitate was filtered and washed with ethanol to afford the expected compound (from 25% to 65% yield).

Example 58

2-Benzylamino-7-oxo-4,7-dihydro-[1,2,4]triazolo[1,5-a]pyrimidine-6-carboxylic acid ethyl ester

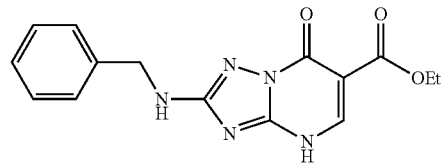 [SMILES: CCOC(=O)c1c[nH]c2nc(NCc3ccccc3)nn2c1=O]

The expected compound was obtained according to general procedure A using benzylamine. The expected compound was isolated as white powder.

MS: 314.1

Mp: 275° C.-278° C.

Example 59

2-(4-Bromobenzylamino)-7-oxo-4,7-dihydro-[1,2,4]triazolo[1,5-a]pyrimidine-6-carboxylic acid ethyl ester

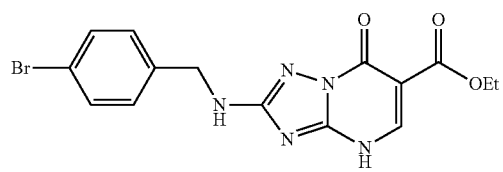 [SMILES: CCOC(=O)c1c[nH]c2nc(NCc3ccc(Br)cc3)nn2c1=O]

The expected compound was obtained according to general procedure A using 4-bromo-benzylamine. The expected compound was isolated as white powder.

Example 60

2-[(Naphthalen-1-ylmethyl)-amino]-7-oxo-4,7-dihydro-[1,2,4]triazolo[1,5a]pyrimidine-6-carboxylic acid ethyl ester

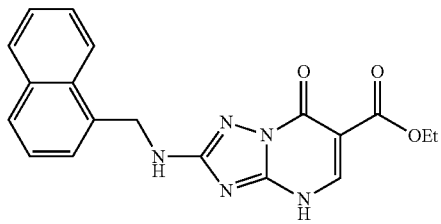 [SMILES: CCOC(=O)c1c[nH]c2nc(NCc3cccc4ccccc34)nn2c1=O]

The expected compound was obtained according to general procedure A using C-(2,3-dihydro-naphthalen-1-yl)-methylamine. The expected compound was isolated as white powder.

MS: 364.2
Mp: 273° C.-275° C.

Example 61

2-(4-Isopropoxy-phenylamino)-7-oxo-4,7-dihydro-[1,2,4]triazolo[1,5-a]pyrimidine-6-carboxylic acid ethyl ester

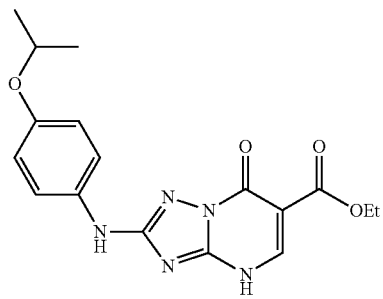 [SMILES: CCOC(=O)c1c[nH]c2nc(Nc3ccc(OC(C)C)cc3)nn2c1=O]

The expected compound was obtained according to general procedure A using 4-isopropoxy-phenylamine. The expected compound was isolated as pale yellow powder.

MS: 358.2
Mp: decomposes at 325° C.-330° C.

Example 62

2-(4-Acetylamino-phenylamino)-7-oxo-4,7-dihydro-[1,2,4]triazolo[1,5-a]pyrimidine-6-carboxylic acid ethyl ester

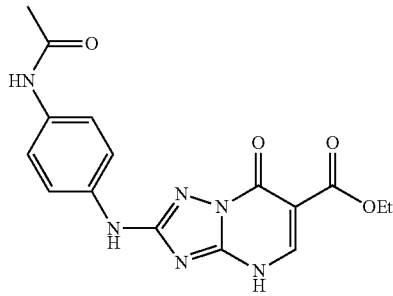 [SMILES: CCOC(=O)c1c[nH]c2nc(Nc3ccc(NC(C)=O)cc3)nn2c1=O]

MS: 392.2
Mp: 286° C.-287° C.

The expected compound was obtained according to general procedure A using N-(4-amino-phenyl)-acetamide. The expected compound was isolated as off-white powder.

MS: 357.2
Mp>330° C.

Example 63

2-(3-Chloro-4-methyl-phenylamino)-7-oxo-4,7-dihydro-[1,2,4]triazolo[1,5-a]pyrimidine-6-carboxylic acid ethyl ester

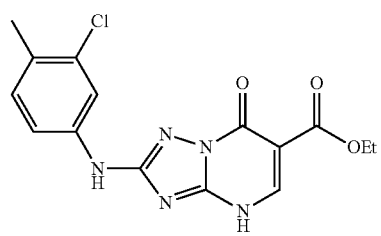 [SMILES: CCOC(=O)c1c[nH]c2nc(Nc3ccc(C)c(Cl)c3)nn2c1=O]

The expected compound was obtained according to general procedure A using 3-chloro-4-methyl-phenylamine. The expected compound was isolated as white powder.

MS: 348.1
Mp>340° C.

General Procedure B

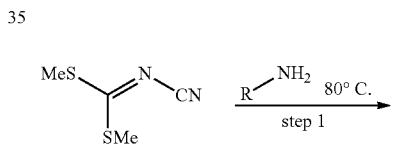

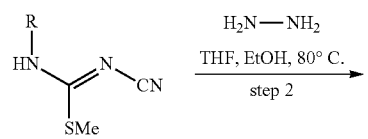

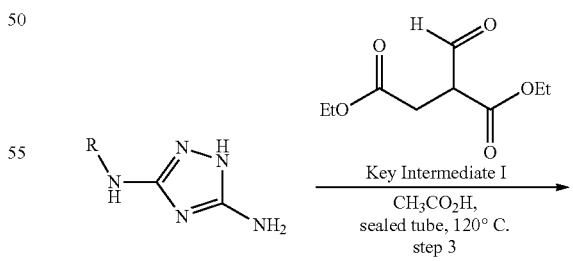

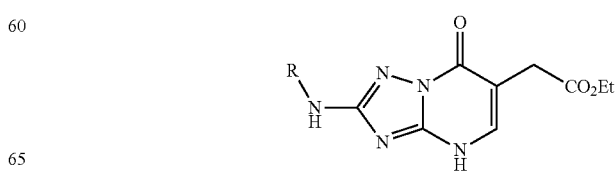

step 1:

To a solution of the appropriate amine (4.3 mmol, 1 eq) in ethanol (10 mL) was added dimethyl N-cyanodithioiminocarbonate (1.0 g, 6.8 mmol, 1.6 eq). The mixture was stirred at 80° C. for 20 h. After cooling, the precipitate was filtered and rinsed with ethanol to afford the expected compound (from 25% to 70% yield).

Step 2:

To a solution of the compound from step 1 (1.1 mmol, 1 eq) in ethanol (10 mL) was added a 1M solution of hydrazine in tetrahydrofuran (2.3 mL, 2.3 mmol, 2 eq). The mixture was heated at 80° C. for 20 h and was evaporated to dryness. The product was then triturated with diethyl ether, filtered and washed with diethyl ether to afford the expected compound (from 75% to 85% yield).

Step 3:

To a solution of the compound from step 2 (1.2 mmol, 1 eq) in acetic acid (6 mL) was added 2-formyl-succinic acid diethyl ester (Key Intermediate I) (277 mg, 1.37 mmol, 1.1 eq). The mixture was heated in a sealed tube at 120° C. for 20 h. After cooling, the mixture was evaporated to dryness. The residue was diluted in ethyl acetate (10 mL) and washed with a saturated solution of sodium bicarbonate (2×10 mL). The organic layers were dried over magnesium sulfate, filtered and evaporated in vacuo. If necessary, the crude compound was purified by flash chromatography using dichloromethane and methanol to afford the expected compound (from 35% to 45% yield).

Example 64

(7-oxo-2-phenylamino-4,7-dihydro-[1,2,4]triazolo[1,5-a]pyrimidin-6-yl)-acetic acid ethyl ester

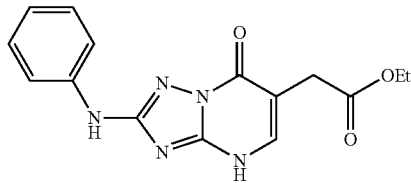 [SMILES: CCOC(=O)Cc1c[nH]c2nc(Nc3ccccc3)nn2c1=O]

The expected compound was obtained according to general procedure B using aniline. The expected compound was isolated as white powder.

MS: 314.2
Mp: 255° C.-257° C.

Example 65

[2-(4-Isopropoxy-phenylamino)-7-oxo-4,7-dihydro-[1,2,4]triazolo[1,5-a]pyrimidin-6-yl]-acetic acid ethyl ester

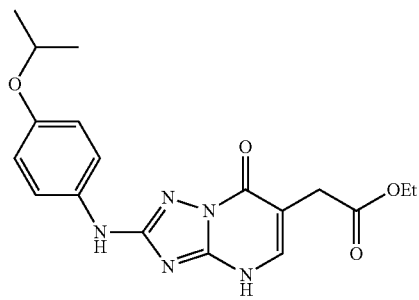 [SMILES: CCOC(=O)Cc1c[nH]c2nc(Nc3ccc(OC(C)C)cc3)nn2c1=O]

The expected compound was obtained according to general procedure B using 4-isopropoxy-phenylamine. The expected compound was isolated as pale yellow powder.

MS: 372.2
Mp: 235° C.-240° C.

General Procedure C

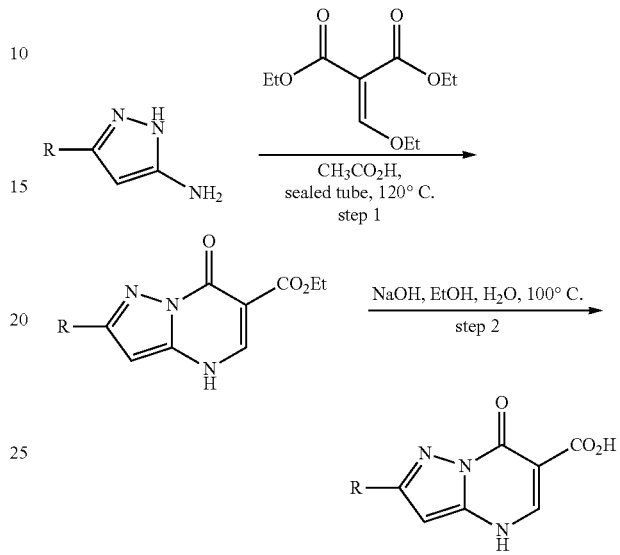

Step 1:

To a solution of 2H-pyrazol-3-ylamine (2.3 mmol, 1 eq) in acetic acid (3 mL) was added 2-ethoxymethylene-malonic acid diethyl ester (500 µL, 2.5 mmol, 1.1 eq). The mixture was heated at 120° C. for 20 h in a sealed tube. After cooling, the precipitate was filtered and washed with ethanol to afford the expected compound (from 30% to 80% yield).

Step 2:

To a solution of the compound from step 1 (1.7 mmol, 1 eq) in ethanol (2 mL) were added sodium hydroxide (170 mg, 4.24 mmol, 2.5 eq) and water (2 mL). The mixture was heated in a sealed tube at 100° C. for 4 h. After cooling, the mixture was evaporated to dryness and water (30 mL) and citric acid (980 mg, 5.1 mmol, 3 eq) were added. The precipitate obtained was filtered, washed with water and dried under vacuum to afford the expected compound (50% to quant. yield).

Example 66

3-Bromo-2-methyl-7-oxo-4,7-dihydro-pyrazolo[1,5-a]pyrimidine-6-carboxylic acid ethyl ester

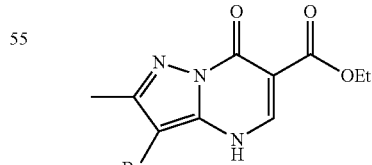

The expected compound was obtained according to general procedure C step 1 using 4-bromo-5-methyl-2H-pyrazol-3-ylamine. The expected compound was isolated as pale yellow powder.

MS: 300.0
Mp: decomposes at 270° C.-275° C.

Example 67

3-Cyano-2-(3-methylamino-propyl)-7-oxo-4,7-dihydro-pyrazolo[1,5-a]pyrimidine-6-carboxylic acid ethyl ester

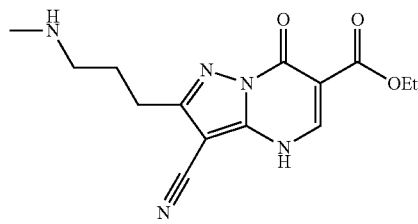 [SMILES: CCOC(=O)c1c[nH]c2c(C#N)c(CCCNC)nn2c1=O]

The expected compound was obtained according to general procedure C step 1 using 5-imino-3-(3-methylamino-propyl)-4,5-dihydro-1H-pyrazole-4-carbonitrile. The expected compound was isolated as white powder.

MS: 304.2
Mp: 285° C.-287° C.

Example 68

7-oxo-2-phenyl-4,7-dihydro-pyrazolo[1,5-a]pyrimidine-6-carboxylic acid

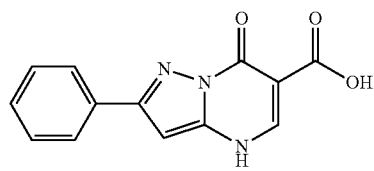 [SMILES: O=C(O)c1c[nH]c2cc(-c3ccccc3)nn2c1=O]

The expected compound was obtained according to general procedure C using 5-phenyl-2H-pyrazol-3-ylamine. The expected compound was isolated as white powder.

MS: 256.0
Mp: decomposes at 325° C.-330° C.

Example 69

2-(4-Ethoxy-phenyl)-7-oxo-4,7-dihydro-pyrazolo[1,5-a]pyrimidine-6-carboxylic acid

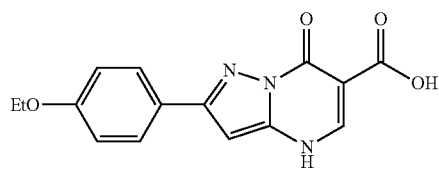 [SMILES: CCOc1ccc(-c2cc3[nH]cc(C(=O)O)c(=O)n3n2)cc1]

The expected compound was obtained according to general procedure C using 5-(4-ethoxy-phenyl)-2H-pyrazol-3-ylamine. The expected compound was isolated as white powder.

MS: 300.1
Mp: decomposes at 310° C.-315° C.

Example 70

2-Cyclopropyl-7-oxo-4,7-dihydro-pyrazolo[1,5-a]pyrimidine-6-carboxylic acid

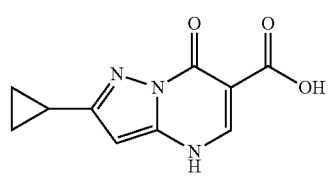 [SMILES: O=C(O)c1c[nH]c2cc(C3CC3)nn2c1=O]

The expected compound was obtained according to general procedure C using 5-cyclopropyl-2H-pyrazol-3-ylamine. The expected compound was isolated as white powder.

MS: 220.0
Mp: 275° C.-278° C.

Example 71

2-Isopropyl-7-oxo-4,7-dihydro-pyrazolo[1,5-a]pyrimidine-6-carboxylic acid

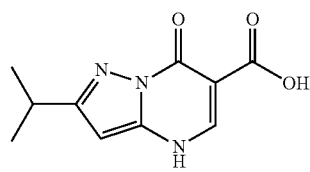 [SMILES: CC(C)c1cc2[nH]cc(C(=O)O)c(=O)n2n1]

The expected compound was obtained according to general procedure C using 5-isopropyl-2H-pyrazol-3-ylamine. The expected compound was isolated as white powder.

MS: 222.0
Mp: decomposes at 280° C.-285° C.

Example 72

2-Cyclopentyl-7-oxo-4,7-dihydro-pyrazolo[1,5-a]pyrimidine-6-carboxylic acid

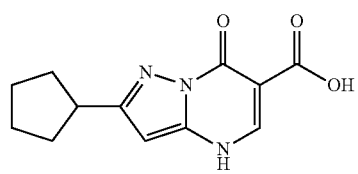 [SMILES: O=C(O)c1c[nH]c2cc(C3CCCC3)nn2c1=O]

The expected compound was obtained according to general procedure C using 5-cyclopentyl-2H-pyrazol-3-ylamine. The expected compound was isolated as white powder.

MS: 248.1
Mp: decomposes at 300° C.

Example 73

7-Oxo-2-trifluoromethyl-4,7-dihydro-pyrazolo[1,5-a]pyrimidine-6-carboxylic acid

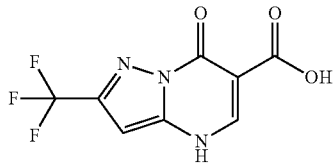 [SMILES: O=C(O)c1c[nH]c2cc(C(F)(F)F)nn2c1=O]

The expected compound was obtained according to general procedure C using 5-trifluoromethyl-2H-pyrazol-3-ylamine. The expected compound was isolated as white powder.
MS: 248.0
Mp>340° C.
General Procedure D

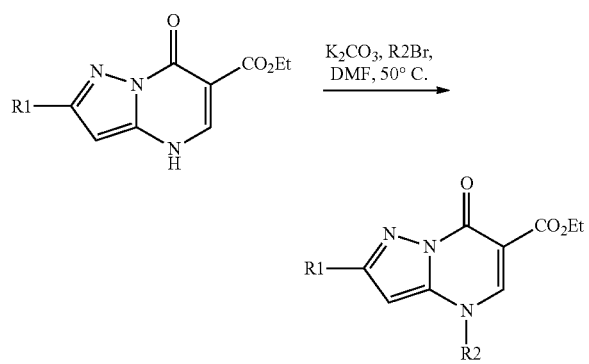

To a solution of 7-oxo-4,7-dihydro-pyrazolo[1,5-a]pyrimidine-6-carboxylic acid ethyl ester (0.81 mmol, 1 eq) in dimethylformamide (5 mL) were added potassium carbonate (560 mg, 4 mmol, 5 eq) and the appropriate bromide (3.2 mmol, 4 eq). The mixture was heated at 50° C. for 4 h. After cooling, the mixture was poured on brine (15 mL) and extracted with ethyl acetate (3×20 mL). The organic layers were dried over magnesium sulfate, filtered and evaporated in vacuo. The crude residue was purified by flash chromatography using dichloromethane and methanol (100/0 to 95/5) to afford the expected compound (13% to 97% yield).

Example 74

4-Benzyl-2-cyclopropyl-7-oxo-4,7-dihydro-pyrazolo[1,5-a]pyrimidine-6-carboxylic acid ethyl ester

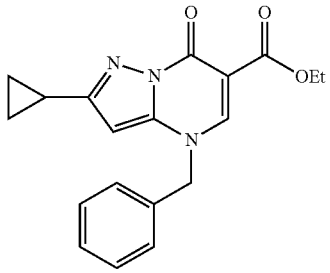 [SMILES: CCOC(=O)c1cn(Cc2ccccc2)c2cc(C3CC3)nn2c1=O]

The expected compound was obtained according to general procedure D using Key Intermediate II and benzyl bromide. The expected compound was isolated as white powder.
MS: 338.2
Mp: 160° C.-165° C.

Example 75

2-Cyclopropyl-7-oxo-4-phenethyl-4,7-dihydro-pyrazolo[1,5-a]pyrimidine-6-carboxylic acid ethyl ester

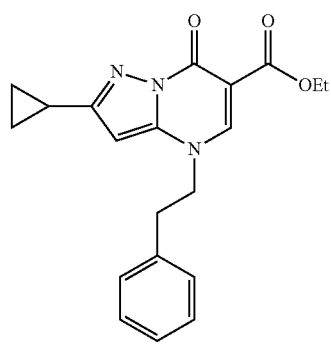 [SMILES: CCOC(=O)c1cn(CCc2ccccc2)c2cc(C3CC3)nn2c1=O]

The expected compound was obtained according to general procedure D using Key Intermediate II and phenethyl bromide. The expected compound was isolated as white powder.
MS: 352.2
Mp: 155° C.-160° C.

Example 76

2-Cyclopropyl-4-[2-(4-hydroxy-phenyl)-ethyl]-7-oxo-4,7-dihydro-pyrazolo[1,5-a]pyrimidine-6-carboxylic acid ethyl ester

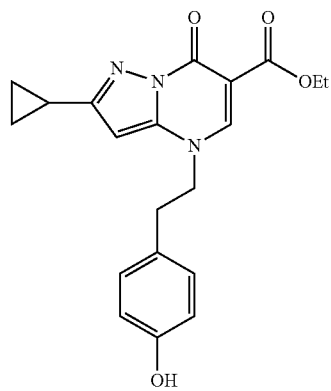 [SMILES: CCOC(=O)c1cn(CCc2ccc(O)cc2)c2cc(C3CC3)nn2c1=O]

The expected compound was obtained according to general procedure D using Key Intermediate II and 4-(2-bromo-ethyl)-phenol. The expected compound was isolated as white powder.

MS: 368.2
Mp: 95° C.-100° C.

Example 77

4-[2-(4-Chloro-phenyl)-ethyl]-2-cyclopropyl-7-oxo-4,7-dihydro-pyrazolo[1,5-a]pyrimidine-6-carboxylic acid ethyl ester

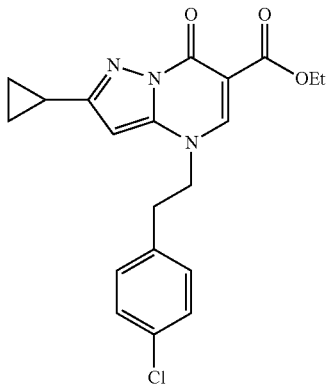 [SMILES: CCOC(=O)c1cn(CCc2ccc(Cl)cc2)c2cc(C3CC3)nn2c1=O]

The expected compound was obtained according to general procedure D using Key Intermediate II and 1-(2-bromo-ethyl)-4-chloro-benzene. The expected compound was isolated as white powder.

MS: 386.2
Mp: 190° C.-195° C.

Example 78

2-Cyclopropyl-4-[2-(4-methoxy-phenyl)-ethyl]-7-oxo-4,7-dihydro-pyrazolo[1,5-a]pyrimidine-6-carboxylic acid ethyl ester

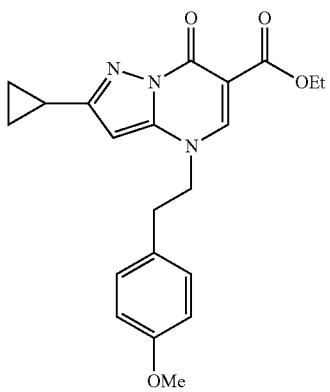 [SMILES: CCOC(=O)c1cn(CCc2ccc(OC)cc2)c2cc(C3CC3)nn2c1=O]

The expected compound was obtained according to general procedure D using Key Intermediate II and 1-(2-bromo-ethyl)-4-methoxy-benzene. The expected compound was isolated as white powder.

MS: 382.2
Mp: 160° C.-165° C.

Example 79

4-[2-(3-Chloro-phenyl)-ethyl]-2-cyclopropyl-7-oxo-4,7-dihydro-pyrazolo[1,5-a]pyrimidine-6-carboxylic acid ethyl ester

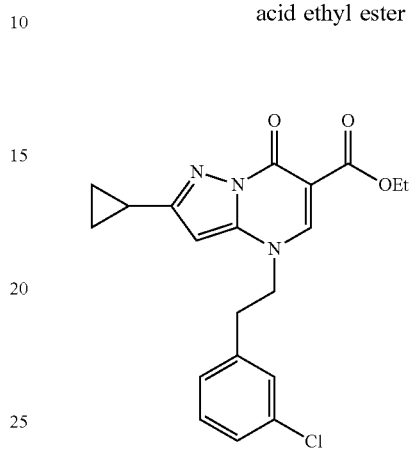

The expected compound was obtained according to general procedure D using Key Intermediate II and 1-(2-bromo-ethyl)-3-chloro-benzene. The expected compound was isolated as white powder.

MS: 386.2
Mp: 160° C.-165° C.

Example 80

2-Cyclopropyl-4-[2-(3-fluoro-phenyl)-ethyl]-7-oxo-4,7-dihydro-pyrazolo[1,5-a]pyrimidine-6-carboxylic acid ethyl ester

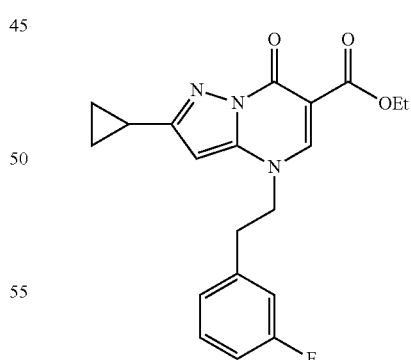

The expected compound was obtained according to general procedure D using Key Intermediate II and 1-(2-bromo-ethyl)-3-fluoro-benzene. The expected compound was isolated as white powder.

MS: 370.2
Mp: 160° C.-165° C.

Example 81

2-Cyclopropyl-7-oxo-4-[2-(3-trifluoromethyl-phenyl)-ethyl]-4,7-dihydro-pyrazolo[1,5-a]pyrimidine-6-carboxylic acid ethyl ester

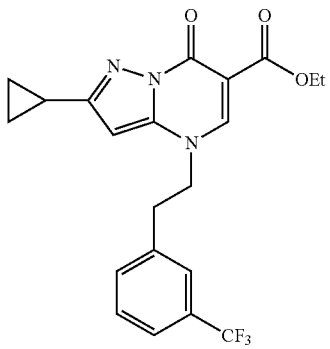 [SMILES: CCOC(=O)c1cn(CCc2cccc(C(F)(F)F)c2)c2cc(C3CC3)nn2c1=O]

The expected compound was obtained according to general procedure D using Key Intermediate II and 1-(2-bromoethyl)-3-trifluoromethyl-benzene. The expected compound was isolated as white powder.
MS: 420.2
Mp: 140° C.-145° C.

Example 82

2-Cyclopropyl-7-oxo-4-(3-phenyl-propyl)-4,7-dihydro-pyrazolo[1,5-a]pyrimidine-6-carboxylic acid ethyl ester

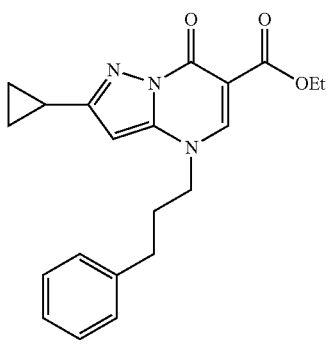 [SMILES: CCOC(=O)c1cn(CCCc2ccccc2)c2cc(C3CC3)nn2c1=O]

The expected compound was obtained according to general procedure E using Key Intermediate II and (3-bromopropyl)-benzene. The expected compound was isolated as white powder.
MS: 366.2
Mp: 150° C.-155° C.

Example 83

4-Benzyl-2-isopropyl-7-oxo-4,7-dihydro-pyrazolo[1,5-a]pyrimidine-6-carboxylic acid ethyl ester

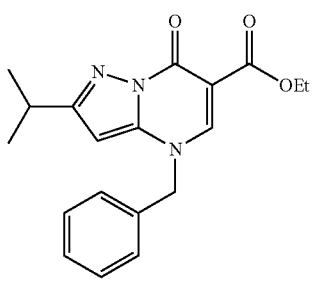 [SMILES: CCOC(=O)c1cn(Cc2ccccc2)c2cc(C(C)C)nn2c1=O]

The expected compound was obtained according to general procedure D using Key Intermediate III and benzyl bromide. The expected compound was isolated as white powder.
MS: 340.2
Mp: 135° C.-140° C.

Example 84

2-Isopropyl-7-oxo-4-phenethyl-4,7-dihydro-pyrazolo[1,5-a]pyrimidine-6-carboxylic acid ethyl ester

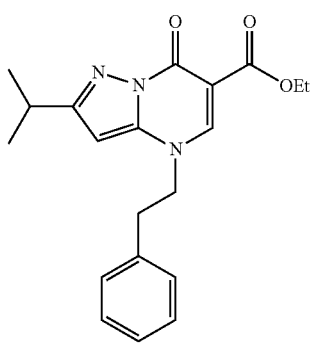 [SMILES: CCOC(=O)c1cn(CCc2ccccc2)c2cc(C(C)C)nn2c1=O]

The expected compound was obtained according to general procedure D using Key Intermediate III and phenethyl bromide. The expected compound was isolated as white powder.
MS: 354.2
Mp: 130° C.-135° C.

Example 85

2-Isopropyl-7-oxo-4-(3-phenyl-propyl)-4,7-dihydro-pyrazolo[1,5-a]pyrimidine-6-carboxylic acid ethyl ester

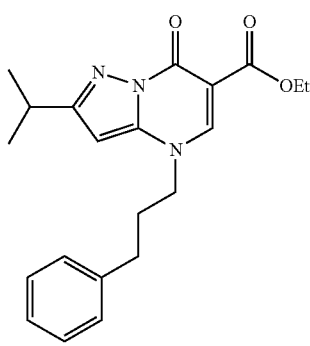 [SMILES: CCOC(=O)c1cn(CCCc2ccccc2)c2cc(C(C)C)nn2c1=O]

The expected compound was obtained according to general procedure D using Key Intermediate III and (3-bromopropyl)-benzene. The expected compound was isolated as colorless oil.
MS: 368.3

Example 86

4-Benzyl-2-cyclopentyl-7-oxo-4,7-dihydro-pyrazolo[1,5-a]pyrimidine-6-carboxylic acid ethyl ester

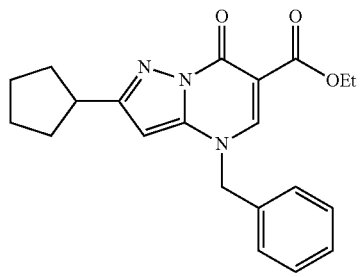 [SMILES: CCOC(=O)c1cn(Cc2ccccc2)c2cc(C3CCCC3)nn2c1=O]

The expected compound was obtained according to general procedure D using Key Intermediate IV and benzyl bromide. The expected compound was isolated as white powder.
MS: 366.2
Mp: 148° C.-150° C.

Example 87

2-Cyclopentyl-7-oxo-4-phenethyl-4,7-dihydro-pyrazolo[1,5-a]pyrimidine-6-carboxylic acid ethyl ester

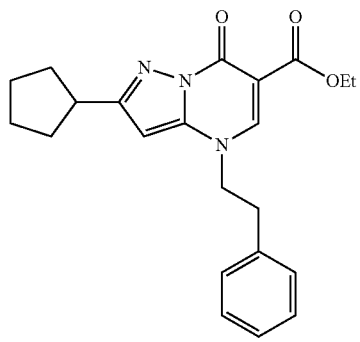 [SMILES: CCOC(=O)c1cn(CCc2ccccc2)c2cc(C3CCCC3)nn2c1=O]

The expected compound was obtained according to general procedure D using Key Intermediate IV and phenethyl bromide. The expected compound was isolated as white powder.
MS: 380.3
Mp: 162° C.-164° C.

General Procedure E

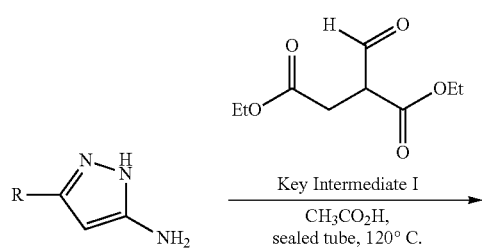

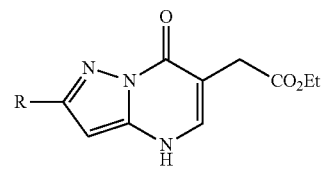

To a solution of 2H-pyrazol-3-ylamine (1.3 mmol, 1 eq) in acetic acid (8 mL) was added 2-formyl-succinic acid diethyl ester (Key Intermediate I) (286 mg, 1.4 mmol, 1.1 eq). The mixture was heated in a sealed tube at 120° C. for 20 h. After cooling, the precipitate was filtered, rinsed with ethanol and dried under vacuum to afford the expected compound (from 18% to 86% yield).

Example 88

(7-Oxo-2-phenyl-4,7-dihydro-pyrazolo[1,5-a]pyrimidin-6-yl)-acetic acid ethyl ester

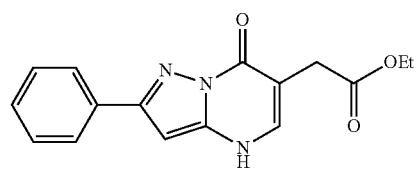 [SMILES: CCOC(=O)Cc1c[nH]c2cc(-c3ccccc3)nn2c1=O]

The expected compound was obtained according to general procedure E using 5-phenyl-2H-pyrazol-3-ylamine. The expected compound was isolated as white powder.
MS: 298.1
Mp: 245° C.-250° C.

Example 89

(7-Oxo-2-trifluoromethyl-4,7-dihydropyrazolo[1,5-a]pyrimidin-6-yl)-acetic acid ethyl ester

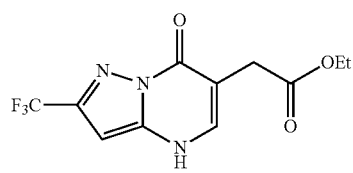 [SMILES: CCOC(=O)Cc1c[nH]c2cc(C(F)(F)F)nn2c1=O]

The expected compound was obtained according to general procedure E using 5-trifluoromethyl-2H-pyrazol-3-ylamine. The expected compound was isolated as white powder.
MS: 290.0
Mp: 290° C.-293° C.

Example 90

(2-Cyclopropyl-7-oxo-4,7-dihydro-pyrazolo[1,5-a]pyrimidin-6-yl)-acetic acid ethyl ester

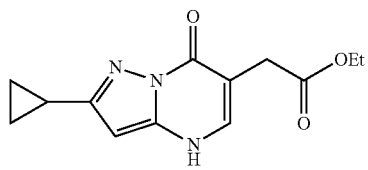 [SMILES: CCOC(=O)Cc1c[nH]c2cc(C3CC3)nn2c1=O]

The expected compound was obtained according to general procedure E using 5-cyclopropyl-2H-pyrazol-3-ylamine. The expected compound was isolated as white powder.
MS: 262.1
Mp: 280° C.-283° C.

Example 91

(2-Cyclopropyl-4-methyl-7-oxo-4,7-dihydro-pyrazolo[1,5-a]pyrimidin-6-yl)-acetic acid ethyl ester

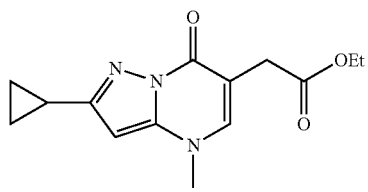 [SMILES: CCOC(=O)Cc1cn(C)c2cc(C3CC3)nn2c1=O]

To a suspension of (2-cyclopropyl-7-oxo-4,7-dihydro-pyrazolo[1,5-a]pyrimidin-6-yl)-acetic acid ethyl ester (80 mg, 0.3 mmol, 1 eq) described in example 90 in tetrahydrofuran (2 mL) was added sodium hydride (16 mg, 3.9 mmol, 1.3 eq). The mixture was stirred during 30 min at room temperature and methyl iodide (30 µL, 0.5 mmol, 1.5 eq) was added. The mixture was stirred at room temperature for 5 h. The mixture was then diluted with ethyl acetate (5 mL) and water (5 mL) was added. The aqueous layer was extracted with ethyl acetate (2×10 mL) and the aqueous phases were dried over magnesium sulfate, filtered and evaporated in vacuo. The crude residue was purified by flash chromatography using cyclohexane and ethyl acetate (100/0 to 0/100) to afford the expected compound as white powder (16 mg, 59% yield).
MS: 276.1
Mp: 147° C.-150° C.

Example 92

(3-Bromo-2-methyl-7-oxo-4,7-dihydro-pyrazolo[1,5-a]pyrimidin-6-yl)-acetic acid ethyl ester

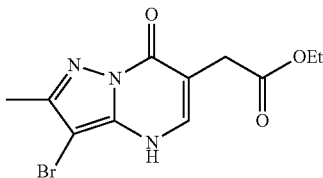 [SMILES: CCOC(=O)Cc1c[nH]c2c(Br)c(C)nn2c1=O]

The expected compound was obtained according to general procedure E using 4-bromo-5-methyl-2H-pyrazol-3-ylamine. The expected compound was isolated as pale pink powder.
MS: 316.0
Mp: decomposes at 245° C.-250° C.

Example 93

2-[2-(4-Chloro-phenyl)-ethylcarbamoyl]-7-oxo-4,7-dihydro-pyrazolo[1,5-a]pyrimidine-6-carboxylic acid ethyl ester

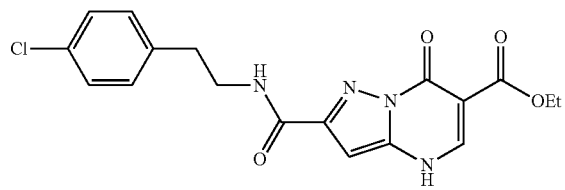 [SMILES: CCOC(=O)c1c[nH]c2cc(C(=O)NCCc3ccc(Cl)cc3)nn2c1=O]

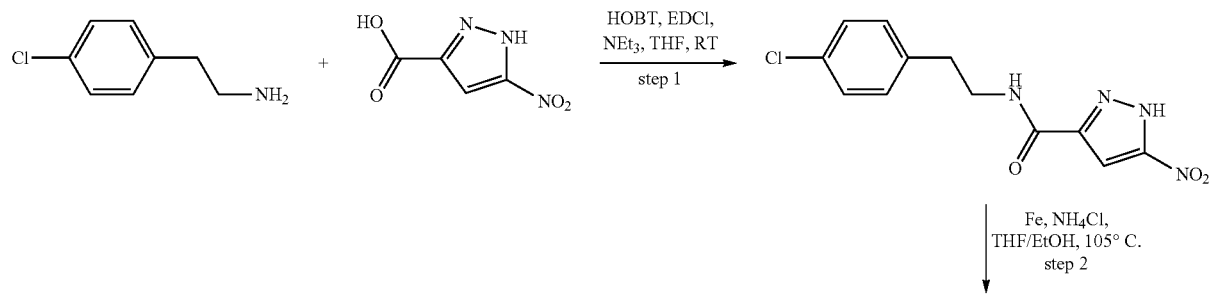

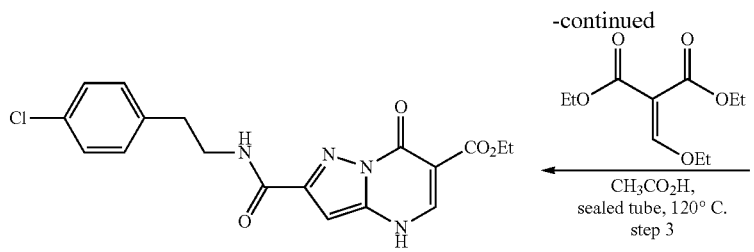 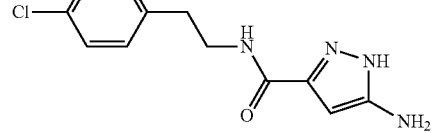

Step 1:

To a solution of 5-nitro-1H-pyrazole-3-carboxylic acid (200 mg, 1.3 mmol, 1 eq) in tetrahydrofuran (5 mL) were added triethylamine (350 μL, 1.9 mmol, 1.5 eq), hydroxybenzotriazole (HOBT) (257 mg, 1.27 mmol, 1 eq), 2-(4-chloro-phenyl)-ethylamine (180 μL, 1.27 mmol, 1 eq) and EDCI (364 mg, 1.9 mmol, 1.5 eq). The mixture was stirred at room temperature during 20 h. Water (10 mL) was then added and the aqueous phase was extracted with ethyl acetate (2×15 mL). The organic layers were dried over magnesium sulfate, filtered and evaporated in vacuo. The crude residue was purified by flash chromatography using cyclohexane and ethyl acetate (100/0) to (50/50) to afford 5-nitro-1H-pyrazole-3-carboxylic acid [2-(4-chloro-phenyl)-ethyl]-amide as white solid (160 mg, 43% yield).

Step 2:

To a solution of 5-nitro-1H-pyrazole-3-carboxylic acid [2-(4-chloro-phenyl)-ethyl]amide (160 mg, 5.42 mmol, 1 eq) in tetrahydrofuran and ethanol (1 mL/3 mL) was added a saturated solution of ammonium chloride (1 mL) and iron (97 mg, 1.73 mmol, 3.2 eq). The mixture was stirred at 105° C. for 16 h. After cooling, the mixture was filtrated on a short pad of celite and washed with ethanol (10 mL), tetrahydrofuran (10 mL) and water (10 mL). The filtrate was evaporated, water (10 mL) was added and the aqueous phase was extracted with dichloromethane (2×15 mL). The organic layers were dried over magnesium sulfate, filtered and evaporated in vacuo to afford 5-amino-1H-pyrazole-3-carboxylic acid [2-(4-chloro-phenyl)-ethyl]-amide as beige powder (100 mg, 70% yield).

Step 3:

To a solution of 5-amino-1H-pyrazole-3-carboxylic acid [2-(4-chloro-phenyl)-ethyl]-amide (100 mg, 0.4 mmol, 1 eq) in acetic acid (2 mL) was added 2-ethoxymethylene-malonic acid diethyl ester (80 μL, 0.44 mmol, 1.1 eq). The mixture was heated at 120° C. for 16 h in a sealed tube. After cooling, the precipitate was filtered and washed with ethanol (2×10 mL) to afford the expected compound as white powder (55 mg, 38% yield).

MS: 389.2

Mp>300° C.

General Procedure F

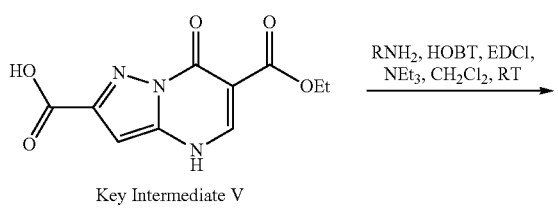

Key Intermediate V

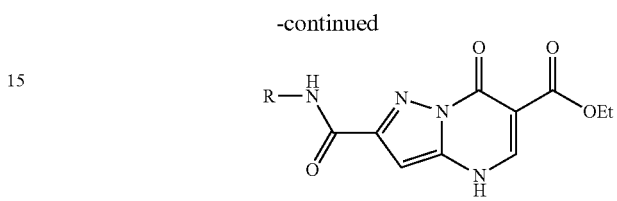

To a solution of 7-oxo-4,7-dihydro-pyrazolo[1,5-a]pyrimidine-2,6-dicarboxylic acid 6-ethyl ester (Key intermediate V) (176 mg, 0.7 mmol, 1 eq) in dichloromethane (5 mL) were added triethylamine (195 μL, 1.4 mmol, 2 eq), HOBT (142 mg, 1.05 mmol, 1.5 eq), the appropriate amine (0.8 mmol, 1.1 eq) and EDCI (201 mg, 1.05 mmol, 1.5 eq). The mixture was stirred at room temperature during 20 h. Water (10 mL) was then added and the aqueous phase was extracted with dichloromethane (2×15 mL). The organic layers were dried over magnesium sulfate, filtered and evaporated in vacuo. The crude residue was purified by flash chromatography using dichloromethane and methanol (100/0) to (80/20). The compound obtained was taken up in methanol and filtered to afford the expected compound as white powder (145 mg, 49% yield).

Example 94

2-(1-Benzylpiperidin-4-ylcarbamoyl)-7-oxo-4,7-dihydropyrazolo[1,5-a]pyrimidine-6-carboxylic acid ethyl ester

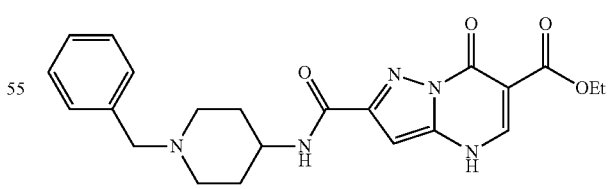

The expected compound was obtained according to general procedure F using Key Intermediate V and 1-benzyl-piperidin-4-ylamine. The expected compound was isolated as white powder.

MS: 424.3

Mp: 264° C.-266° C.

Example 95

2-Benzylcarbamoyl-7-oxo-4,7-dihydropyrazolo[1,5-a]pyrimidine-6-carboxylic acid ethyl ester

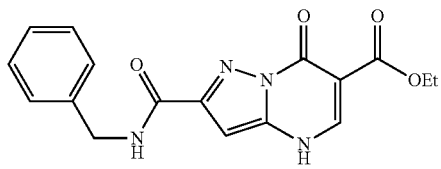 [SMILES: CCOC(=O)c1c[nH]c2cc(C(=O)NCc3ccccc3)nn2c1=O]

The expected compound was obtained according to general procedure F using Key Intermediate V and benzylamine. The expected compound was isolated as pale grey powder.

MS: 341.2
Mp: 290° C.-292° C.

General Procedure G

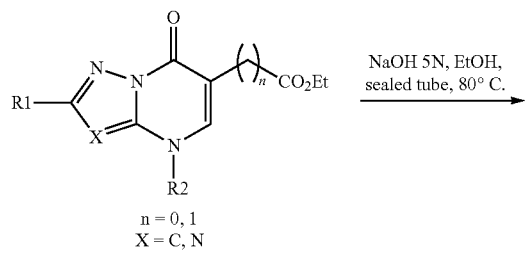

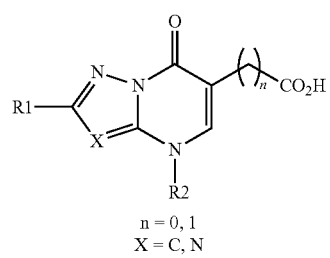

To a solution of the ester (0.32 mmol, 1 eq) in ethanol (6 mL) was added a 5N solution of sodium hydroxide (0.5 mL). The mixture was heated in a sealed tube at 80° C. for 20 h to 48 h. After cooling, the mixture was evaporated to dryness. Then water (5 mL) and citric acid (3 mL) were added. The precipitate obtained was filtered and washed with water to afford the expected compound (65% to quant. yield).

Example 96

2-(4-Isopropoxy-phenylamino)-7-oxo-4,7-dihydro-[1,2,4]triazolo[1,5-a]pyrimidine-6-carboxylic acid

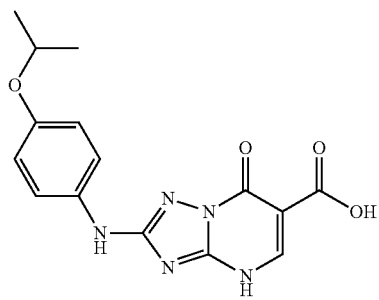 [SMILES: CC(C)Oc1ccc(Nc2nc3[nH]cc(C(=O)O)c(=O)n3n2)cc1]

The expected compound was obtained according to general procedure G using 2-(4-isopropoxy-phenylamino)-7-oxo-4,7-dihydro-[1,2,4]triazolo[1,5-a]pyrimidine-6-carboxylic acid ethyl ester described in example 61. The expected compound was isolated as yellow powder.

MS: 330.1
Mp: decomposes at 260° C.-265° C.

Example 97

2-Benzylamino-7-oxo-4,7-dihydro-[1,2,4]triazolo[1,5-a]pyrimidine-6-carboxylic acid

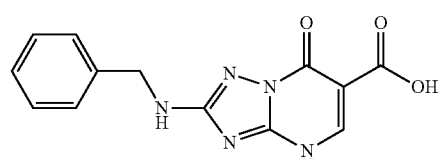

The expected compound was obtained according to general procedure G using 2-benzylamino-7-oxo-4,7-dihydro-[1,2,4]triazolo[1,5-a]pyrimidine-6-carboxylic acid ethyl ester described in example 58. The expected compound was isolated as pale yellow powder.

MS: 286.1
Mp: 240° C.-245° C.

Example 98

2-[(Naphthalen-1-ylmethyl)-amino]-7-oxo-4,7-dihydro-[1,2,4]triazolo[1,5a]pyrimidine-6-carboxylic acid

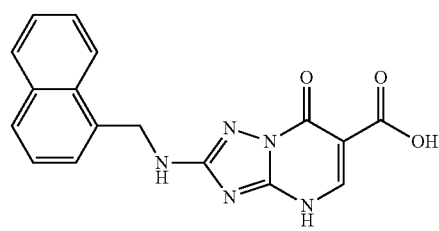 [SMILES: O=C(O)c1c[nH]c2nc(NCc3cccc4ccccc34)nn2c1=O]

The expected compound was obtained according to general procedure G using 2-[(naphthalen-1-ylmethyl)-amino]-7-oxo-4,7-dihydro[1,2,4]triazolo[1,5a]pyrimidine-6-carboxylic acid ethyl ester described in example 60. The expected compound was isolated as pale orange powder.

MS: 336.1
Mp: 245° C.-250° C.

Example 99

2-[(Benzo[1,3]dioxol-5-ylmethyl)-amino]-7-oxo-4,7-dihydro-[1,2,4]triazolo[1,5-a]pyrimidine-6-carboxylic acid sodium salt

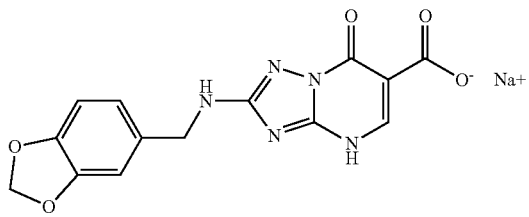 [SMILES: O=C([O-])c1c[nH]c2nc(NCc3ccc4c(c3)OCO4)nn2c1=O ; [Na+]]

The expected compound was obtained according to general procedure G using 2-[(benzo[1,3]dioxol-5-ylmethyl)-amino]-7-oxo-4,7-dihydro-[1,2,4]triazolo[1,5-a]pyrimidine-6-carboxylic acid ethyl ester. This starting material was obtained according to general procedure A using C-benzo[1,3]dioxol-5-yl-methylamine. The expected acid was isolated without treatment as sodium salt and as yellow powder.
MS: 330.1
Mp decomposes at 300° C.

Example 100

(7-Oxo-2-phenylamino-4,7-dihydro-[1,2,4]triazolo[1,5-a]pyrimidin-6-yl)-acetic acid

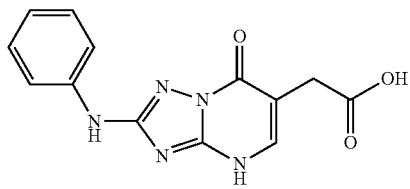 [SMILES: O=C(O)Cc1c[nH]c2nc(Nc3ccccc3)nn2c1=O]

The expected compound was obtained according to general procedure G using (7-oxo-2-phenylamino-4,7-dihydro-[1,2,4]triazolo[1,5-a]pyrimidin-6-ylacetic acid ethyl ester described in example 64. The expected compound was isolated as white powder.
MS: 286.1
Mp: 279° C.-281° C.

Example 101

[2-(4-Isopropoxy-phenylamino)-7-oxo-4,7-dihydro-[1,2,4]triazolo[1,5-a]pyrimidin-6-yl]-acetic acid

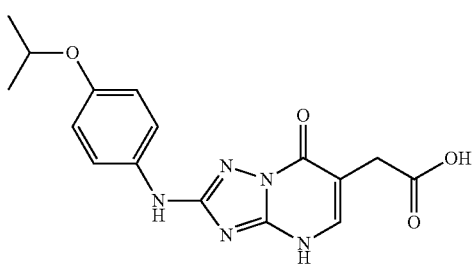 [SMILES: CC(C)Oc1ccc(Nc2nc3[nH]cc(CC(=O)O)c(=O)n3n2)cc1]

The expected compound was obtained according to general procedure G using [2-(4-isopropoxy-phenylamino)-7-oxo-4,7-dihydro-[1,2,4]triazolo[1,5-a]pyrimidin-6-yl]-acetic acid ethyl ester described in example 65.

Example 102

4-Benzyl-2-cyclopropyl-7-oxo-4,7-dihydro-pyrazolo[1,5-a]pyrimidine-6-carboxylic acid

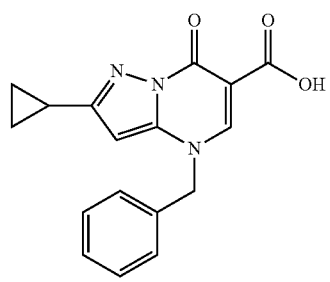 [SMILES: O=C(O)c1cn(Cc2ccccc2)c2cc(C3CC3)nn2c1=O]

The expected compound was obtained according to general procedure G using 4-benzyl-2-cyclopropyl-7-oxo-4,7-dihydro-pyrazolo[1,5-a]pyrimidine-6-carboxylic acid ethyl ester described in example 74. The expected compound was isolated as beige powder.

MS: 310.1
Mp: 210° C.-215° C.

Example 103

2-Cyclopropyl-7-oxo-4-phenethyl-4,7-dihydro-pyrazolo[1,5-a]pyrimidine-6-carboxylic acid

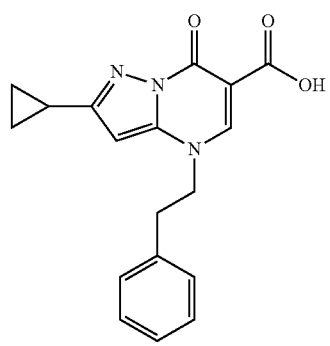 [SMILES: O=C(O)c1cn(CCc2ccccc2)c2cc(C3CC3)nn2c1=O]

The expected compound was obtained according to general procedure G using 2-cyclopropyl-7-oxo-4-phenethyl-4,7-dihydro-pyrazolo[1,5-a]pyrimidine-6-carboxylic acid ethyl ester described in example 75. The expected compound was isolated as beige powder.
MS: 324.1
Mp: 185° C.-190° C.

Example 104

2-Cyclopropyl-4-[2-(4-hydroxy-phenyl)-ethyl]-7-oxo-4,7-dihydro-pyrazolo[1,5-a]-pyrimidine-6-carboxylic acid

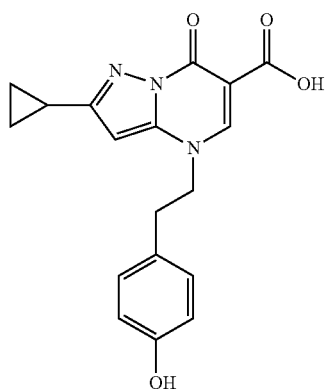 [SMILES: O=C(O)c1cn(CCc2ccc(O)cc2)c2cc(C3CC3)nn2c1=O]

The expected compound was obtained according to general procedure G using 2-cyclopropyl-4-[2-(4-hydroxy-phenyl)-ethyl]-7-oxo-4,7-dihydro-pyrazolo[1,5-a]pyrimidine-6-carboxylic acid ethyl ester described in example 76. The expected compound was isolated as white powder.

MS: 340.1
Mp: 265° C.-270° C.

Example 105

4-[2-(4-Chloro-phenyl)-ethyl]-2-cyclopropyl-7-oxo-4,7-dihydro-pyrazolo[1,5-a]pyrimidine-6-carboxylic acid

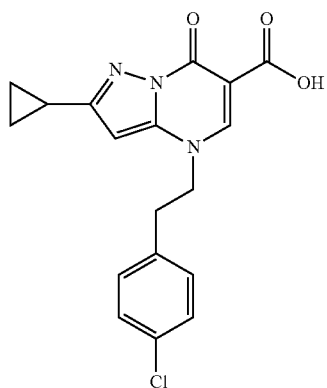 [SMILES: O=C(O)c1cn(CCc2ccc(Cl)cc2)c2cc(C3CC3)nn2c1=O]

The expected compound was obtained according to general procedure G using 4-[2-(4-chloro-phenyl)-ethyl]-2-cyclopropyl-7-oxo-4,7-dihydro-pyrazolo[1,5-a]pyrimidine-6-carboxylic acid ethyl ester described in example 77. The expected compound was isolated as white powder.

MS: 358.1
Mp: 220° C.-225° C.

Example 106

2-Cyclopropyl-4-[2-(4-methoxy-phenyl)-ethyl]-7-oxo-4,7-dihydro-pyrazolo[1,5-a]-pyrimidine-6-carboxylic acid

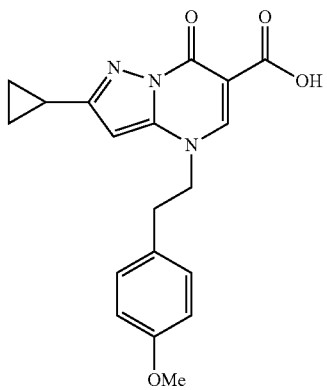 [SMILES: COc1ccc(CCn2cc(C(=O)O)c(=O)n3nc(C4CC4)cc23)cc1]

The expected compound was obtained according to general procedure G using 2-cyclopropyl-4-[2-(4-methoxy-phenyl)-ethyl]-7-oxo-4,7-dihydro-pyrazolo[1,5-a]pyrimidine-6-carboxylic acid ethyl ester described in example 78. The expected compound was isolated as white powder.

MS: 354.2
Mp: 145° C.-150° C.

Example 107

2-Cyclopropyl-7-oxo-4-[2-(4-trifluoromethyl-phenyl)-ethyl]-4,7-dihydro-pyrazolo[1,5-a]-pyrimidine-6-carboxylic acid

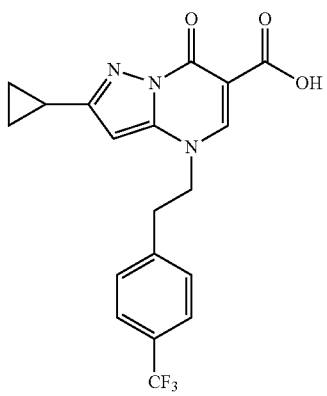 [SMILES: O=C(O)c1cn(CCc2ccc(C(F)(F)F)cc2)c2cc(C3CC3)nn2c1=O]

The expected compound was obtained according to general procedure G using 2-cyclopropyl-7-oxo-4-[2-(4-trifluoromethyl-phenyl)-ethyl]-4,7-dihydro-pyrazolo[1,5-a]pyrimidine-6-carboxylic acid ethyl ester. The starting material was obtained according to general procedure D using Key Intermediate II and 1-(2-bromo-ethyl)-4-trifluoromethyl-benzene. The expected compound was isolated as white powder.

MS: 392.2
Mp: 225° C.-230° C.

Example 108

4-[2-(3-Chloro-phenyl)-ethyl]-2-cyclopropyl-7-oxo-4,7-dihydro-pyrazolo[1,5-a]-pyrimidine-6-carboxylic acid

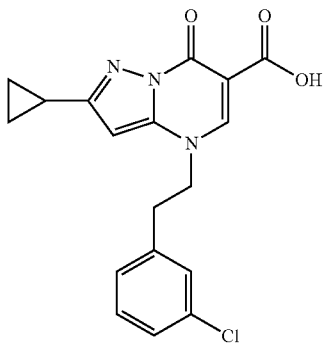 [SMILES: O=C(O)c1cn(CCc2cccc(Cl)c2)c2cc(C3CC3)nn2c1=O]

The expected compound was obtained according to general procedure G using 4-[2-(3-chloro-phenyl)-ethyl]-2-cyclopropyl-7-oxo-4,7-dihydro-pyrazolo[1,5-a]pyrimidine-6-carboxylic acid ethyl ester described in example 79. The expected compound was isolated as white powder.

MS: 358.1
Mp: 230° C.-235° C.

Example 109

2-Cyclopropyl-4-[2-(3-fluoro-phenyl)-ethyl]-7-oxo-4,7-dihydro-pyrazolo[1,5-a]pyrimidine-6-carboxylic acid

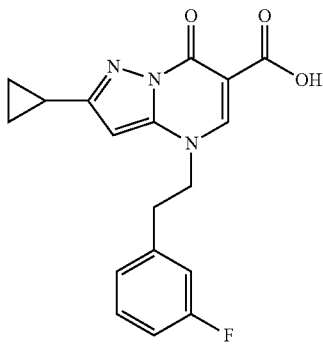

The expected compound was obtained according to general procedure G using 2-cyclopropyl-4-[2-(3-fluoro-phenyl)-ethyl]-7-oxo-4,7-dihydro-pyrazolo[1,5-a]pyrimidine-6-carboxylic acid ethyl ester described in example 80. The expected compound was isolated as white powder.

MS: 342.1
Mp: 220° C.-225° C.

Example 110

2-Cyclopropyl-7-oxo-4-[2-(3-trifluoromethyl-phenyl)-ethyl]-4,7-dihydro-pyrazolo[1,5-a]-pyrimidine-6-carboxylic acid

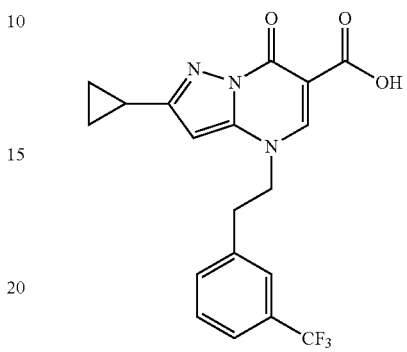

The expected compound was obtained according to general procedure G using 2-cyclopropyl-7-oxo-4-[2-(3-trifluoromethyl-phenyl)-ethyl]-4,7-dihydro-pyrazolo[1,5-a]pyrimidine-6-carboxylic acid ethyl ester described in example 81. The expected compound was isolated as white powder.

MS: 392.2
Mp: 200° C.-205° C.

Example 111

2-Cyclopropyl-7-oxo-4-(3-phenyl-propyl)-4,7-dihydro-pyrazolo[1,5-a]pyrimidine-6-carboxylic acid

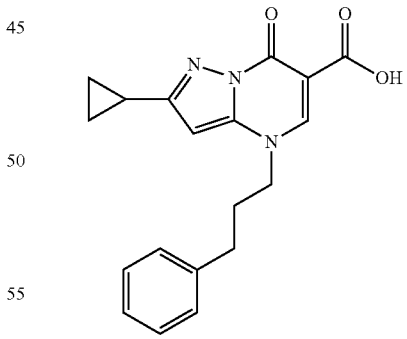

The expected compound was obtained according to general procedure G using 2-cyclopropyl-7-oxo-4-(3-phenyl-propyl)-4,7-dihydro-pyrazolo[1,5-a]pyrimidine-6-carboxylic acid ethyl ester described in example 82. The expected compound was isolated as beige powder.

MS: 338.2
Mp: 95° C.-100° C.

Example 112

4-Benzyl-2-isopropyl-7-oxo-4,7-dihydro-pyrazolo[1,5-a]pyrimidine-6-carboxylic acid

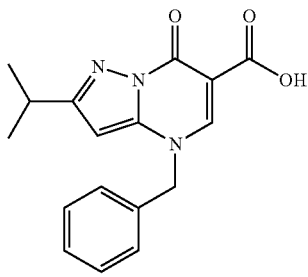 [SMILES: CC(C)c1cc2n(Cc3ccccc3)cc(C(=O)O)c(=O)n2n1]

The expected compound was obtained according to general procedure G using 4-benzyl-2-isopropyl-7-oxo-4,7-dihydro-pyrazolo[1,5-a]pyrimidine-6-carboxylic acid ethyl ester described in example 83. The expected compound was isolated as beige powder.
MS: 312.1
Mp: 180° C.-185° C.

Example 113

2-Isopropyl-7-oxo-4-phenethyl-4,7-dihydro-pyrazolo[1,5-a]pyrimidine-6-carboxylic acid

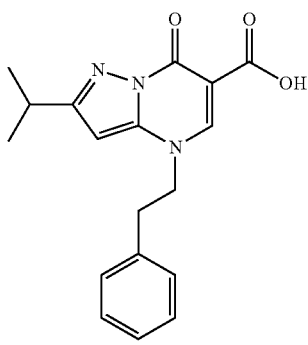 [SMILES: CC(C)c1cc2n(CCc3ccccc3)cc(C(=O)O)c(=O)n2n1]

The expected compound was obtained according to general procedure G using 2-isopropyl-7-oxo-4-phenethyl-4,7-dihydro-pyrazolo[1,5-a]pyrimidine-6-carboxylic acid ethyl ester described in example 84. The expected compound was isolated as white powder.
MS: 326.2
Mp: 220° C.-225° C.

Example 114

2-Isopropyl-7-oxo-4-(3-phenyl-propyl)-4,7-dihydro-pyrazolo[1,5-a]pyrimidine-6-carboxylic acid

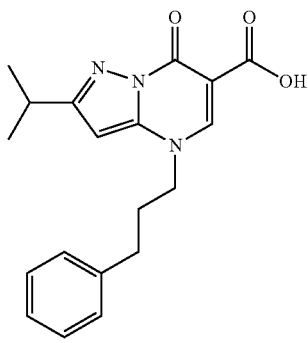 [SMILES: CC(C)c1cc2n(CCCc3ccccc3)cc(C(=O)O)c(=O)n2n1]

The expected compound was obtained according to general procedure G using 2-isopropyl-7-oxo-4-(3-phenyl-propyl)-4,7-dihydro-pyrazolo[1,5-a]pyrimidine-6-carboxylic acid ethyl ester described in example 85. The expected compound was isolated as orange oil.
MS: 340.2

Example 115

4-Benzyl-2-cyclopentyl-7-oxo-4,7-dihydro-pyrazolo[1,5-a]pyrimidine-6-carboxylic acid

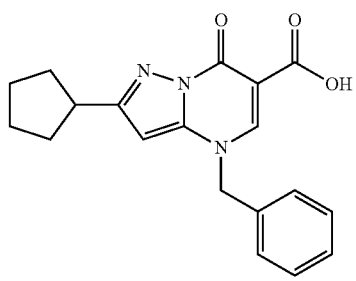 [SMILES: O=C(O)c1cn(Cc2ccccc2)c2cc(C3CCCC3)nn2c1=O]

The expected compound was obtained according to general procedure G using 4-benzyl-2-cyclopentyl-7-oxo-4,7-dihydro-pyrazolo[1,5-a]pyrimidine-6-carboxylic acid ethyl ester described in example 86. The expected compound was isolated as white powder.
MS: 338.2
Mp: 213° C.-215° C.

Example 116

2-Cyclopentyl-7-oxo-4-phenethyl-4,7-dihydro-pyrazolo[1,5-a]pyrimidine-6-carboxylic acid

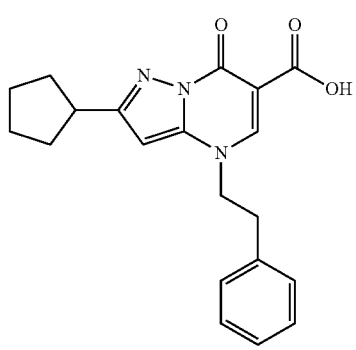 [SMILES: O=C(O)c1cn(CCc2ccccc2)c2cc(C3CCCC3)nn2c1=O]

The expected compound was obtained according to general procedure G using 2-cyclopentyl-7-oxo-4-phenethyl-4,7-dihydro-pyrazolo[1,5-a]pyrimidine-6-carboxylic acid ethyl ester described in example 87. The expected compound was isolated as white powder.
MS: 352.2
Mp: 198° C.-200° C.

Example 117

(7-Oxo-2-phenyl-4,7-dihydro-pyrazolo[1,5-a]pyrimidin-6-yl)-acetic acid

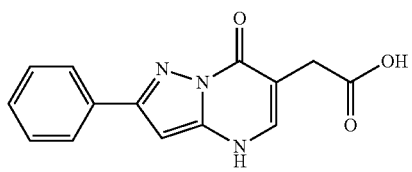 [SMILES: O=C(O)Cc1c[nH]c2cc(-c3ccccc3)nn2c1=O]

The expected compound was obtained according to general procedure G using (2-phenyl-7-oxo-4,7-dihydro-pyrazolo[1,5-a]pyrimidin-6-yl)-acetic acid ethyl ester described in example 88. The expected compound was isolated as beige powder.
MS: 270.1
Mp decomposes at 285° C.-290° C.

Example 118

[2-(4-Ethoxy-phenyl)-7-oxo-4,7-dihydro-pyrazolo[1,5-a]pyrimidin-6-yl]-acetic acid

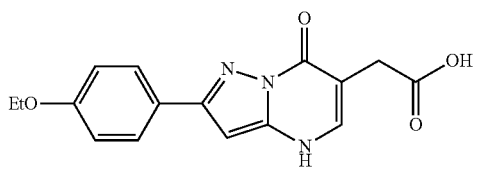 [SMILES: CCOc1ccc(-c2cc3[nH]cc(CC(=O)O)c(=O)n3n2)cc1]

The expected compound was obtained according to general procedure G using [2-(4-ethoxy-phenyl)-7-oxo-4,7-dihydro-pyrazolo[1,5-a]pyrimidin-6-yl]acetic acid ethyl ester. The starting material was obtained according to general procedure E using 5-(4-ethoxy-phenyl)-2H-pyrazol-3-ylamine. The expected compound was isolated as white powder.
MS: 314.1
Mp: decomposes at 295° C.-300° C.

Example 119

(7-Oxo-2-trifluoromethyl-4,7-dihydro-pyrazolo[1,5-a]pyrimidin-6-yl)-acetic acid

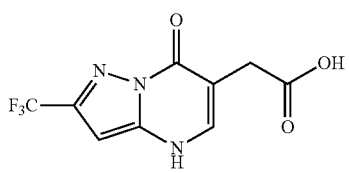 [SMILES: O=C(O)Cc1c[nH]c2cc(C(F)(F)F)nn2c1=O]

The expected compound was obtained according to general procedure G using (7-oxo-2-trifluoromethyl-4,7-dihydropyrazolo[1,5-a]pyrimidin-6-yl)-acetic acid ethyl ester described in example 89. The expected compound was isolated as pale salmon colored powder.

MS: 262.0
Mp: 320° C.-324° C.

Example 120

(2-Cyclopropyl-7-oxo-4,7-dihydro-pyrazolo[1,5-a]pyrimidin-6-yl)-acetic acid

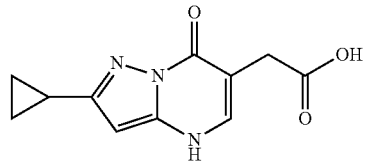 [SMILES: O=C(O)Cc1c[nH]c2cc(C3CC3)nn2c1=O]

The expected compound was obtained according to general procedure G using (2-cyclopropyl-7-oxo-4,7-dihydro-pyrazolo[1,5-a]pyrimidin-6-yl)-acetic acid ethyl ester described in example 90. The expected compound was isolated as white powder.
MS: 234.1
Mp>300° C.

Example 121

2-[2-(4-Chloro-phenyl)-ethylcarbamoyl]-7-oxo-4,7-dihydro-pyrazolo[1,5-a]pyrimidine-6-carboxylic acid

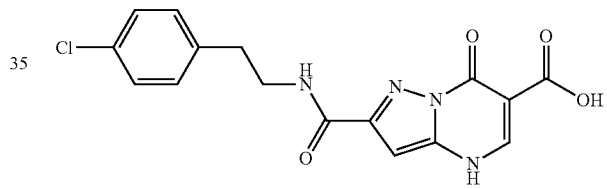

The expected compound was obtained according to general procedure G using [2-[2-(4-chloro-phenyl)-ethylcarbamoyl]-7-oxo-4,7-dihydro-pyrazolo[1,5-a]pyrimidine-6-carboxylic acid ethyl ester described in example 93. The expected compound was isolated as white powder.
MS: 361.1
Mp>300° C.

Example 122

Sodium 2-(1-benzyl-piperidin-4-ylcarbamoyl)-7-oxo-4,7-dihydro-pyrazolo[1,5-a]-pyrimidine-6-carboxylate

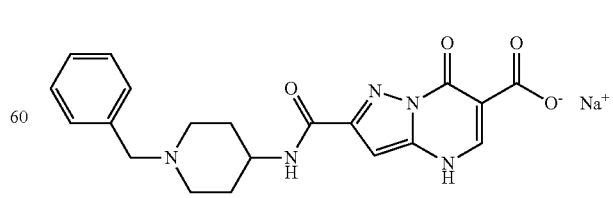

The expected compound was obtained according to general procedure G using 2-(1-benzylpiperidin-4-ylcarbamoyl)-7-oxo-4,7-dihydropyrazolo[1,5-a]pyrimidine-6-carboxylic acid ethyl ester described in example 94. Instead of the described treatment, the precipitate obtained was filtered to isolate the expected compound as the sodium salt and as white powder.

MS: 396.2

Mp: decomposes at 300° C.

General Procedure H:

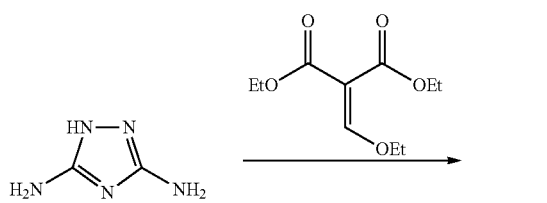

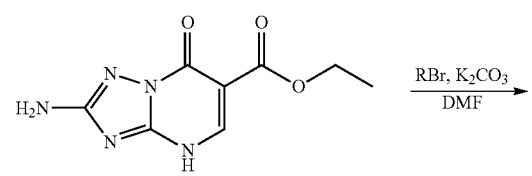

Key Intermediate VI

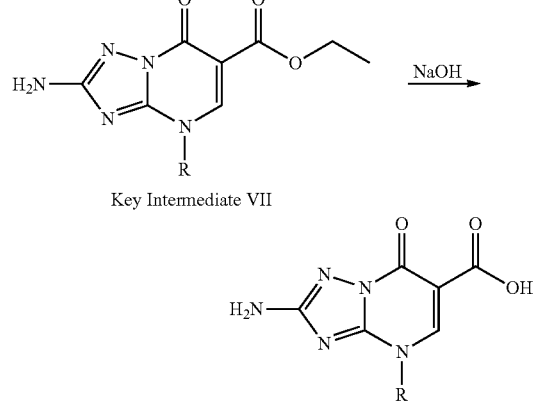

Key Intermediate VII

Step 1:

1H-1,2,4-Triazole-3,5-diamine (12.4 g, 0.125 mol) was dissolved in AcOH (50 ml), and diethyl 2-(ethoxymethylene) malonate (32.5 g, 0.15 mol) was added. The solution was refluxed overnight, then cooled, filtered, and dried to give Key Intermediate VI (22 g, 79%) as a white solid.

Step 2:

To a mixture of VI (500 mg, 2.2 mmol) in N-methylpyrrolidone (20 ml), $K_2CO_3$ (619 mg, 4.5 mmol) and RBr (3.4 mmol) were added. The solution was stirred at 50° C. overnight. The solution was cooled, filtered, and concentrated. The solid was washed with MeOH (20 ml), and dried to give Key Intermediate VII as a white solid.

A mixture of VII and NaOH (2.0 eq. (mmol)) in $CH_3OH/THF/H_2O$ (5/5/1) was stirred at r.t. for 2 h. The solvent was removed in vacuum. The residue was dissolved in water (20 ml), the pH value was adjusted to 6, then filtered, and dried to give desired compounds as a white solid.

Example 123

2-Amino-4-benzyl-7-oxo-4,7-dihydro-[1,2,4]triazolo[1,5-a]pyrimidine-6-carboxylic acid

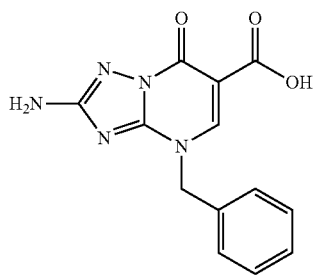

VI was treated with benzylbromide according to the general procedure H to obtain compound 66 as a white solid.

Yield: 10%

MS (ESI): 286 (M+H)$^+$ $^1$H NMR (d$_6$-DMSO, 300 MHz):

δ 12.87 (br, s, 1H), 8.86 (s, 1H), 7.34-7.41 (m, 5H), 6.42 (s, 2H), 5.43 (s, 2H)

Example 124

2-Amino-7-oxo-4-phenethyl-4,7-dihydro-[1,2,4]triazolo[1,5-a]pyrimidine-6-carboxylic acid

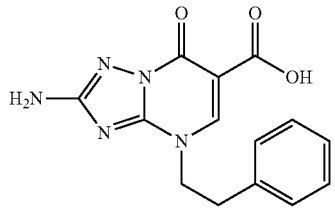 [SMILES: Nc1nc2n(CCc3ccccc3)cc(C(=O)O)c(=O)n2n1]

VI was treated with phenethylbromide according to the general procedure H to obtain compound 67 as a white solid.

Yield: 11%

MS (ESI): 300 (M+H)$^+$

1H NMR (d$_6$-DMSO, 300 MHz):

δ 12.84 (s, 1H), 8.69 (s, 1H), 7.30-7.40 (m, 5H), 6.54 (s, 2H), 4.49 (t, J=7.2 Hz, 2H), 3.19 (t, J=7.2 Hz, 2H)

$^{13}$C NMR (d$_6$-DMSO, 300 MHz):

Example 125

2-Amino-4-(cyclohexyl methyl)-7-oxo-4,7-dihydro-[1,2,4]triazolo[1,5-a]pyrimidine-6-carboxylic acid

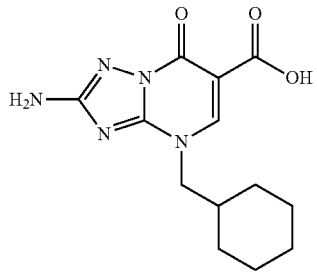 [SMILES: Nc1nc2n(CC3CCCCC3)cc(C(=O)O)c(=O)n2n1]

VI was treated with (bromomethyl)cyclohexane according to the general procedure H to obtain compound 68 as a white solid.

Yield: 10%

MS (ESI): 292 (M+H)+

1H NMR (d6-DMSO, 300 MHz):

δ 12.86 (s, 1H), 8.69 (s, 1H), 6.44 (s, 2H), 4.05 (d, J=7.2 Hz, 2H), 1.89-1.95 (m, 1H), 1.56-1.67 (m, 5H), 0.90-1.15 (m, 5H)

Example 126

2-Amino-4-isopropyl-7-oxo-4,7-dihydro-[1,2,4]triazolo[1,5-a]pyrimidine-6-carboxylic acid

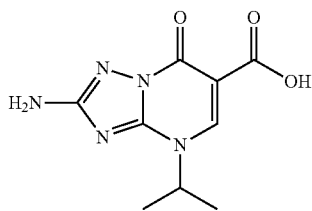 [SMILES: CC(C)n1cc(C(=O)O)c(=O)n2nc(N)nc12]

VI was treated with 2-bromopropane according to the general procedure H to obtain compound 69 as a white solid.

Yield: 11%

MS (ESI): 238 (M+H)+

1H NMR (d6-DMSO, 300 MHz):

δ 12.97 (s, 1H), 8.71 (s, 1H), 6.50 (s, 2H), 4.86-4.95 (m, 1H), 1.58 (d, J=6.6 Hz, 6H)

Example 127

2-Amino-4-(biphenyl-2-ylmethyl)-7-oxo-4,7-dihydro-[1,2,4]triazolo[1,5-a]pyrimidine-6-carboxylic acid

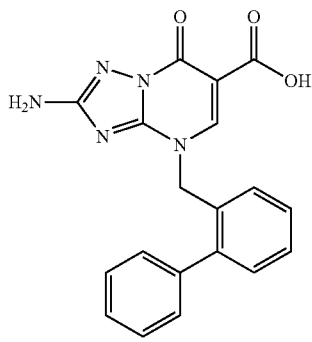

VI was treated with 2-(bromomethyl)biphenyl according to the general procedure H to obtain compound 70 as a white solid.

Yield: 13%

MS (ESI): 362 (M+H)+

1H NMR (d6-DMSO, 300 MHz):

δ 12.76 (br, s, 1H), 8.47 (s, 1H), 7.34-7.47 (m, 7H), 7.20-7.29 (m, 2H), 6.32 (s, 2H), 5.39 (s, 2H)

Examples 128 and 129

2-Amino-4-[1-adamantyl]-7-oxo-4,7-dihydro-[1,2,4]triazolo[1,5-a]pyrimidine-6-carboxylic acid and 2-amino-4-[1-adamantyl]-[1,2,4]triazolo[1,5-a]pyrimidin-7(4H)-one

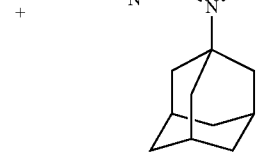

VI was treated with 1-bromoadamantane according to the general procedure to obtain compounds 128 and 129 as a brown solid.

Yield: 5%

MS (ESI): 330 (M+H)+, 286

A19, 1H NMR (CDCl3, 300 MHz):

δ 8.46 (s, 1H), 2.00-2.22 (m, 9H), 1.58-1.70 (m, 3H)

A19-0, 1H NMR (CDCl3, 300 MHz):

δ 7.69 (d, J=6.6 Hz, 1H), 5.73 (d, J=6.6 Hz, 1H) 2.00-2.22 (m, 9H), 1.58-1.70 (m, 3H)

Activity Data for Compounds Having General Formula (C)

| Structure | FRET | CPE |
|---|---|---|
| (pyrazolo[1,5-a]pyrimidine carboxylic acid) | IC50 = 58 µM | inactive |
| (triazolopyrimidine with CH3 and acetic acid) | inactive | 28% @ 50 µM |
| (triazolo[1,5-a]pyrimidine-6-carboxylic acid) | 26% @ 5 µM | inactive |

-continued

| Structure | FRET | CPE |
|---|---|---|
| (2-isopropyl-7-oxo-4-(3-phenylpropyl)pyrazolo[1,5-a]pyrimidine-6-carboxylic acid) | 23% @ 5 μM | inactive |
| (2-(benzylamino)-7-oxo-4H-[1,2,4]triazolo[1,5-a]pyrimidine-6-carboxylic acid) | IC$_{50}$ = 50 μM | inactive |
| (2-isopropyl-7-oxo-4H-pyrazolo[1,5-a]pyrimidine-6-carboxylic acid) | IC$_{50}$ = 35 μM | inactive |
| (2-cyclopentyl-7-oxo-4H-pyrazolo[1,5-a]pyrimidine-6-carboxylic acid) | 41% @ 25 μM | inactive |
| (2-cyclopentyl-7-oxo-4-phenethylpyrazolo[1,5-a]pyrimidine-6-carboxylic acid) | 42% @ 25 μM | inactive |
| (2-amino-7-oxo-4-(1-phenylcyclopentanecarbonyl)pyrazolo[1,5-a]pyrimidine-6-carboxylic acid) | 20% @ 25 μM | inactive |

-continued

| Structure | FRET | CPE |
|---|---|---|
| (2-cyclopentyl-7-oxo-4-phenethylpyrazolo[1,5-a]pyrimidine-6-carboxylic acid) | 26% @ 25 μM | inactive |
| (2-isopropyl-7-oxo-4-(3-phenylpropyl)pyrazolo[1,5-a]pyrimidine-6-carboxylic acid) | 22% @ 25 μM | inactive |
| (ethyl 2-cyclopropyl-4-(4-hydroxyphenethyl)-7-oxopyrazolo[1,5-a]pyrimidine-6-carboxylate) | 22% @ 25 μM | inactive |
| (4-(3-chlorophenethyl)-2-cyclopropyl-7-oxopyrazolo[1,5-a]pyrimidine-6-carboxylic acid) | 30% @ 25 μM | inactive |

| Structure | FRET | CPE |
|---|---|---|
| 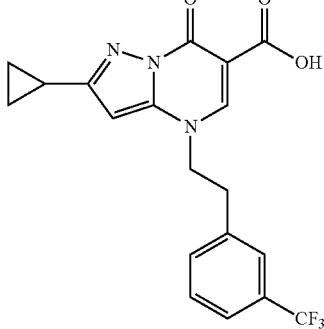 | 32% @ 25 μM | inactive |
| 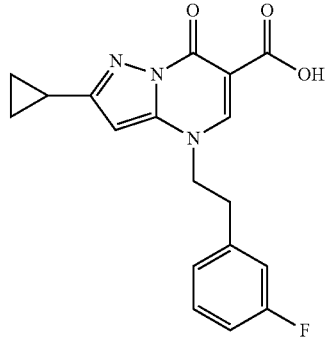 [SMILES: O=C(O)c1cn(CCc2cccc(F)c2)c2cc(C3CC3)nn2c1=O] | IC$_{50}$ = 62 μM | inactive |
| 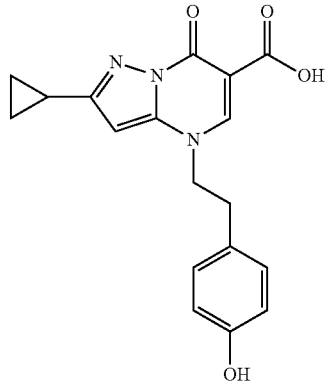 [SMILES: O=C(O)c1cn(CCc2ccc(O)cc2)c2cc(C3CC3)nn2c1=O] | 27% @ 25 μM | inactive |
| 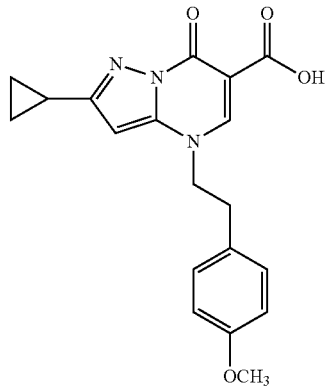 [SMILES: COc1ccc(CCn2cc(C(=O)O)c(=O)n3nc(C4CC4)cc23)cc1] | IC$_{50}$ = 69 μM | inactive |
| Structure | FRET | CPE |
|---|---|---|
| 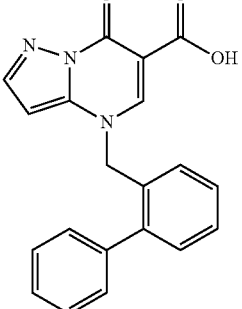 | 29% @ 50 μM | inactive |
| 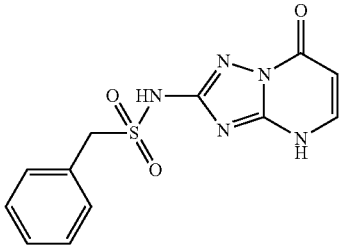 [SMILES: O=c1cc[nH]c2nc(NS(=O)(=O)Cc3ccccc3)nn12] | IC$_{50}$ = 34 μM | n.d. |
| 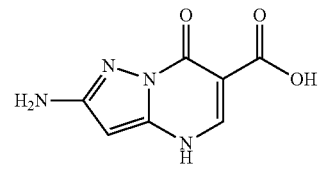 [SMILES: Nc1cc2[nH]cc(C(=O)O)c(=O)n2n1] | IC$_{50}$ = 10 μM | n.d. |
| 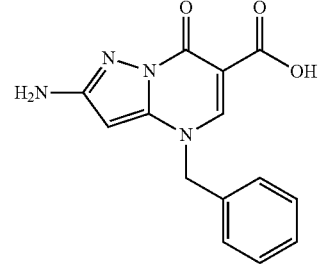 [SMILES: Nc1cc2n(Cc3ccccc3)cc(C(=O)O)c(=O)n2n1] | 35% @ 50 μM | n.d. |
| 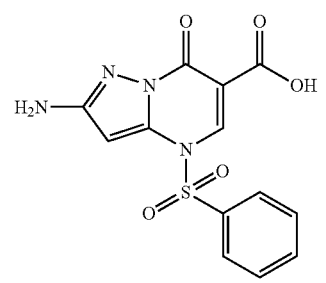 [SMILES: Nc1cc2n(S(=O)(=O)c3ccccc3)cc(C(=O)O)c(=O)n2n1] | IC$_{50}$ = 71 μM | inactive |
| 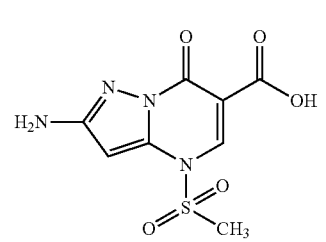 [SMILES: CS(=O)(=O)n1cc(C(=O)O)c(=O)n2nc(N)cc12] | 31% @ 25 μM | inactive |

-continued

| Structure | FRET | CPE |
|---|---|---|
| (structure) | 50% @ 25 µM | inactive |
| (structure) | 38% @ 10 µM | inactive |
| (structure) | inactive | 18% @ 50 µM |

The invention claimed is:

1. A compound having the general formula (A)

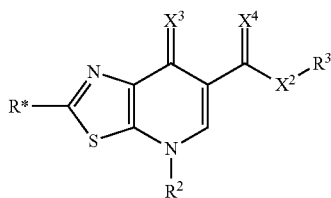

(A)

wherein
R* is —H, —Hal, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), —$C_{1-4}$ alkyl-(optionally substituted aryl) or —$X^1$—$R^1$;
$X^1$ is O, C(O), C(O)O, OC(O); S, SO, $SO_2$, $NR^4$, $N(R^5)$ C(O), C(O)$NR^5$;
$X^2$ is O, S, $NR^4$;
$X^3$ is O or S;
$X^4$ is O or S;
$R^1$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), —$C_{1-4}$ alkyl-(optionally substituted aryl);

$R^3$ is —H, -(optionally substituted $C_{1-6}$ alkyl), -(optionally substituted $C_{3-7}$ cycloalkyl), -(optionally substituted aryl), or —$C_{1-4}$ alkyl-(optionally substituted aryl) if $X^2$ is $NR^4$ then $R^3$ can also be —OH;

$R^4$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^1$ is $NR^4$, then $R^4$ and $R^1$ can be joined together to form a 5- to 7-membered ring, which can optionally contain O, S or further N or if $X^2$ is $NR^4$, then $R^4$ and $R^3$ can be joined together to form a 5- to 7-membered ring, which can optionally contain O, S or further N; and $R^5$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl); and $R^6$ is —H, or —$C_{1-6}$ alkyl;

wherein the optional substituent of the alkyl group is selected from the group consisting of halogen, —CN, —$NR^6R^6$, —OH, and —O—$C_{1-6}$ alkyl;

wherein the optional substituent of the cycloalkyl group, the aryl group or the hydrocarbon group is selected from the group consisting of —$C_{1-6}$ alkyl, halogen, —$CF_3$, —CN, —$X^1$—$R^5$ and —$C_{1-4}$ alkyl-aryl;

wherein $R^2$ is selected from the group consisting of

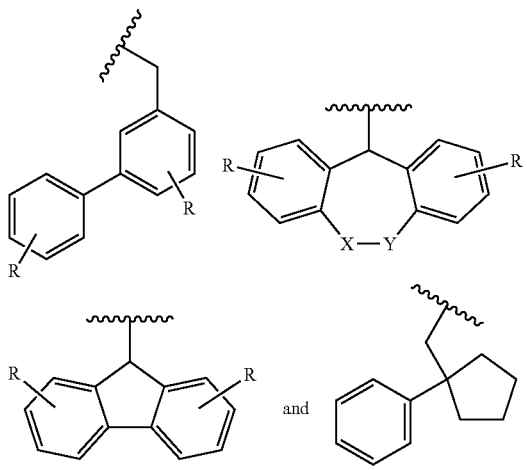

and wherein
X is absent, $CH_2$, NH, C(O)NH, S or O;
Y is $CH_2$; or
X and Y can be joined together to form an annulated, carbo- or heterocylic 3- to 8-membered ring which can be saturated or unsaturated; and
R is independently selected from H, —$C_{1-6}$ alkyl, halogen, —CN, —OH, and —O—$C_{1-6}$ alkyl;
or a pharmaceutically acceptable salt, solvate, polymorph, cocrystal, prodrug, tautomer, racemate, enantiomer, or diastereomer or mixture thereof,
wherein, the prodrug is a compound where $X^2$ is O or S, and $R^3$ is one of the following groups:

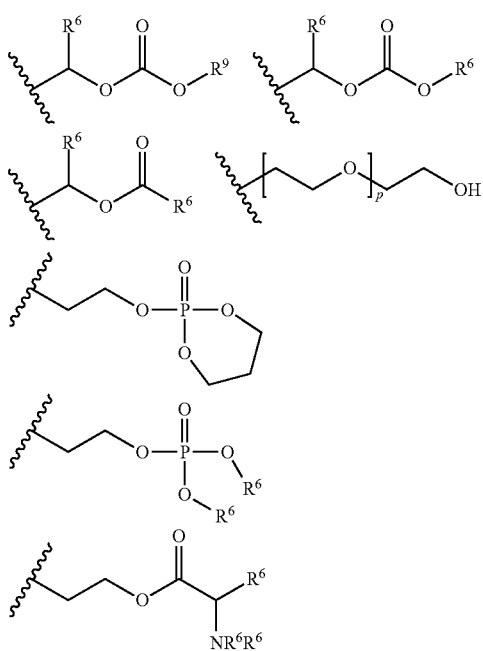

wherein $R^6$ is the same or different,
wherein $R^9$ is aryl or $C_{3-7}$ cycloalkyl,
p is 2-8.

2. A pharmaceutical composition comprising (i) a compound having the general formula (A)

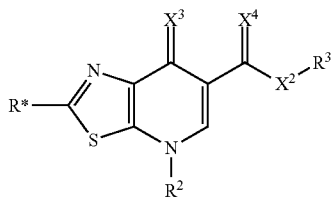
(A)

wherein
R* is —H, —Hal, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), —$C_{1-4}$ alkyl-(optionally substituted aryl) or —$X^1$—$R^1$;
$X^1$ is O, C(O), C(O)O, OC(O); S, SO, $SO_2$, $NR^4$, $N(R^5)$ C(O), C(O)$NR^5$;
$X^2$ is O, S, $NR^4$;
$X^3$ is O or S;
$X^4$ is O or S;
$R^1$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), —$C_{1-4}$ alkyl-(optionally substituted aryl);
$R^3$ is —H, -(optionally substituted $C_{1-6}$ alkyl), -(optionally substituted $C_{3-7}$ cycloalkyl), -(optionally substituted aryl), or —$C_{1-4}$ alkyl-(optionally substituted aryl) or if $X^2$ is $NR^4$, then $R^3$ can also be —OH;
$R^4$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^1$ is $NR^4$, then $R^4$ and $R^1$ can be joined together to form a 5- to 7-membered ring, which can optionally contain O, S or further N or if $X^2$ is $NR^4$, then $R^4$ and $R^3$ can be joined together to form a 5- to 7-membered ring, which can optionally contain O, S or further N; and
$R^5$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl); and
$R^6$ is —H, or —$C_{1-6}$ alkyl;
wherein the optional substituent of the alkyl group is selected from the group consisting of halogen, —CN, —$NR^6R^6$, —OH, and —O—$C_{1-6}$ alkyl;
wherein the optional substituent of the cycloalkyl group, the aryl group or the hydrocarbon group is selected from the group consisting of —$C_{1-6}$ alkyl, halogen, —$CF_3$, —CN, —$X^1$—$R^5$ and —$C_{1-4}$ alkyl-aryl;
wherein $R^2$ is selected from the group consisting of

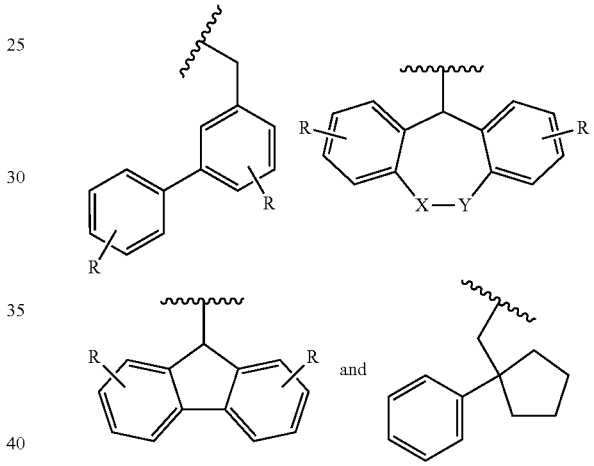

wherein
X is absent, $CH_2$, NH, C(O)NH, S or O;
Y is $CH_2$; or
X and Y can be joined together to form an annulated, carbo- or heterocylic 3- to 8-membered ring which can be saturated or unsaturated; and
R is independently selected from H, —$C_{1-6}$ alkyl, halogen, —CN, —OH, and —O—$C_{1-6}$ alkyl;
or a pharmaceutically acceptable salt, solvate, polymorph, cocrystal, prodrug, tautomer, racemate, enantiomer, or diastereomer or mixture thereof,
wherein, the prodrug is a compound where $X^2$ is O or S, and $R^3$ is one of the following groups:

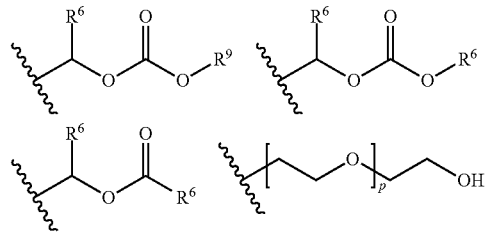

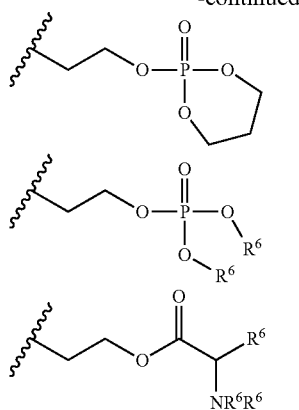

wherein R⁶ is the same or different,
wherein R⁹ is aryl or C₃₋₇ cycloalkyl,
p is 2-8;
and (ii) a pharmaceutically acceptable excipient.

3. A compound having the general formula (A)

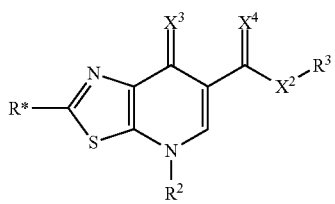
(A)

wherein
R* is —H, —Hal, -(optionally substituted C₁₋₆ alkyl), -(optionally substituted C₃₋₇ cycloalkyl), -(optionally substituted aryl), —C₁₋₄ alkyl-(optionally substituted C₃₋₇ cycloalkyl), —C₁₋₄ alkyl-(optionally substituted aryl) or —X¹—R¹;
X¹ is O, C(O), C(O)O, OC(O); S, SO, SO₂, NR⁴, N(R⁵)C(O), C(O)NR⁵;
X² is O, S, NR⁴;
X³ is O or S;
X⁴ is O or S;
R¹ is —H, -(optionally substituted C₁₋₆ alkyl), -(optionally substituted C₃₋₇ cycloalkyl), -(optionally substituted aryl), —C₁₋₄ alkyl-(optionally substituted C₃₋₇ cycloalkyl), —C₁₋₄ alkyl-(optionally substituted aryl);
R³ is —H, -(optionally substituted C₁₋₆ alkyl), -(optionally substituted C₃₋₇ cycloalkyl), -(optionally substituted aryl), or —C₁₋₄ alkyl-(optionally substituted aryl) or if X² is NR⁴, then R³ can also be —OH;
R⁴ is —H, -(optionally substituted C₁₋₆ alkyl), -(optionally substituted C₃₋₇ cycloalkyl), -(optionally substituted aryl), —C₁₋₄ alkyl-(optionally substituted C₃₋₇ cycloalkyl), or —C₁₋₄ alkyl-(optionally substituted aryl) or if X¹ is NR⁴, then R⁴ and R¹ can be joined together to form a 5- to 7-membered ring, which can optionally contain O, S or further N or if X² is NR⁴, then R⁴ and R³ can be joined together to form a 5- to 7-membered ring, which can optionally contain O, S or further N; and
R⁵ is —H, -(optionally substituted C₁₋₆ alkyl), -(optionally substituted C₃₋₇ cycloalkyl), -(optionally substituted aryl), —C₁₋₄ alkyl-(optionally substituted C₃₋₇ cycloalkyl), or —C₁₋₄ alkyl-(optionally substituted aryl); and R⁶ is —H, or —C₁₋₆ alkyl;
wherein the optional substituent of the alkyl group is selected from the group consisting of halogen, —CN, —NR⁶R⁶, —OH, and —O—C₁₋₆ alkyl;
wherein the optional substituent of the cycloalkyl group, the aryl group or the hydrocarbon group is selected from the group consisting of —C₁₋₆ alkyl, halogen, —CF₃, —CN, —X¹—R⁵ and —C₁₋₄ alkyl-aryl;
wherein R² is selected from the group consisting of

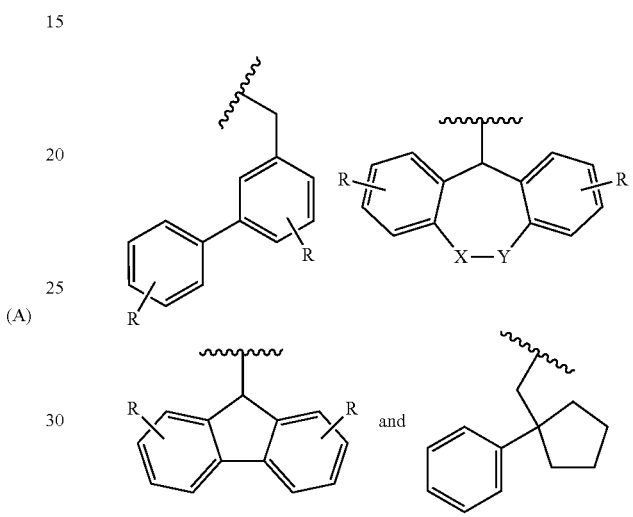

wherein
X is absent, CH₂, NH, C(O)NH, S or O;
Y is CH₂; or
X and Y can be joined together to form an annulated, carbo- or heterocyclic 3- to 8-membered ring which can be saturated or unsaturated; and
R is independently selected from H, —C₁₋₆ alkyl, halogen, —CN, —OH, and —O—C₁₋₆ alkyl;
or a pharmaceutically acceptable salt, solvate, polymorph, cocrystal, prodrug, tautomer, racemate, enantiomer, or diastereomer or mixture thereof,
wherein, the prodrug is a compound where X² is O or S, and R³ is one of the following groups:

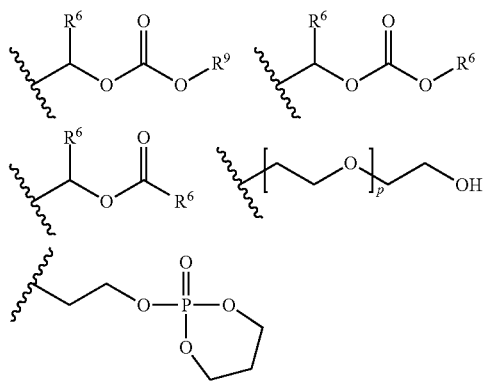

-continued

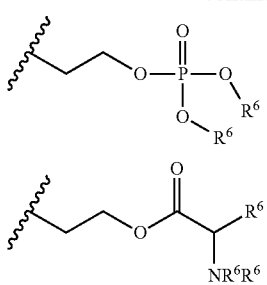

wherein R⁶ is the same or different, wherein R⁹ is aryl or $C_{3-7}$ cycloalkyl, p is 2-8;

wherein the compound is for use in the treatment or amelioration of a viral disease, wherein the viral disease is influenza.

4. A method of treating or ameliorating a viral disease, the method comprising administering to a patient in need thereof an effective amount of a compound according to claim 3, wherein the viral disease is influenza.

5. The compound according to claim 1, wherein $X^1$ is $NR^4$.

6. The compound according to claim 1, wherein $X^1$ is $NR^4$ and wherein $R^1$ and $R^4$ are joined together to form a 5- to 7-membered ring, which can optionally contain O, S or further N.

7. The compound according to claim 1, wherein $R^3$ is —H, —$C_{1-6}$ alkyl or Bz.

8. A pharmaceutical composition comprising:
(i) a compound having the general formula (A) as defined in claim 3, and
(ii) at least one polymerase inhibitor which is different from the compound having the general formula (A).

9. A pharmaceutical composition comprising:
(i) a compound having the general formula (A) as defined in claim 3, and
(ii) at least one neuramidase inhibitor.

10. A pharmaceutical composition comprising:
(i) a compound having the general formula (A) as defined in claim 3, and
(ii) at least one M2 channel inhibitor.

11. A pharmaceutical composition comprising:
(i) a compound having the general formula (A) as defined in claim 3, and
(ii) at least one alpha glucosidase inhibitor.

12. A pharmaceutical composition comprising:
(i) a compound having the general formula (A) as defined in claim 3, and
(ii) at least one ligand of another influenza target.

13. A pharmaceutical composition comprising:
(i) a compound having the general formula (A) as defined in claim 3, and
(ii) at least one medicament selected from antibiotics, anti-inflammatory agents, lipoxygenase inhibitors, EP ligands, bradykinin ligands, and cannabinoid ligands.

14. A method of treating or ameliorating a viral disease, the method comprising administering to a patient in need thereof an effective amount of a pharmaceutical composition according to any of claims 8 to 13, wherein the viral disease is influenza.

* * * * *